(12) United States Patent
El-Sayed et al.

(10) Patent No.: US 9,415,123 B2
(45) Date of Patent: Aug. 16, 2016

(54) POLYMERIC NANOPARTICLES FOR ULTRASOUND IMAGING AND THERAPY

(71) Applicant: THE REGENTS OF THE UNIVERSITY OF MICHIGAN, Ann Arbor, MI (US)

(72) Inventors: Mohamed El-Sayed, Dexter, MI (US); Yasemin Yuksel Durmaz, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 22 days.

(21) Appl. No.: 14/349,304

(22) PCT Filed: Oct. 10, 2012

(86) PCT No.: PCT/US2012/059556
§ 371 (c)(1),
(2) Date: Apr. 2, 2014

(87) PCT Pub. No.: WO2013/055791
PCT Pub. Date: Apr. 18, 2013

(65) Prior Publication Data
US 2014/0243664 A1 Aug. 28, 2014

Related U.S. Application Data

(60) Provisional application No. 61/545,418, filed on Oct. 10, 2011, provisional application No. 61/545,898, filed on Oct. 11, 2011.

(51) Int. Cl.
| | | |
|---|---|---|
| *A61K 49/22* | (2006.01) | |
| *A61M 37/00* | (2006.01) | |
| *A61K 47/32* | (2006.01) | |
| *A61B 8/08* | (2006.01) | |
| *A61K 47/48* | (2006.01) | |
| *G01N 33/574* | (2006.01) | |
| *G01N 33/58* | (2006.01) | |
| *A61K 9/00* | (2006.01) | |
| *C08F 293/00* | (2006.01) | |
| *B82Y 5/00* | (2011.01) | |
| *A61K 9/50* | (2006.01) | |
| *A61K 9/51* | (2006.01) | |
| *A61B 8/00* | (2006.01) | |

(52) U.S. Cl.
CPC ............. *A61K 49/22* (2013.01); *A61B 8/085* (2013.01); *A61B 8/481* (2013.01); *A61K 9/0009* (2013.01); *A61K 9/5026* (2013.01); *A61K 9/5031* (2013.01); *A61K 9/5089* (2013.01); *A61K 9/5138* (2013.01); *A61K 9/5146* (2013.01); *A61K 9/5192* (2013.01); *A61K 47/32* (2013.01); *A61K 47/48869* (2013.01); *A61K 47/48969* (2013.01); *A61M 37/0092* (2013.01); *B82Y 5/00* (2013.01); *C08F 293/005* (2013.01); *G01N 33/57415* (2013.01); *G01N 33/57434* (2013.01); *G01N 33/57438* (2013.01); *G01N 33/587* (2013.01); *A61B 8/4281* (2013.01); *C08F 2438/01* (2013.01); *Y10T 428/2982* (2015.01)

(58) Field of Classification Search
CPC ...... A61B 8/4281; A61B 8/481; A61K 47/32; A61K 47/48953; A61K 49/22; A61K 9/0009; A61K 9/5026; A61K 9/5031; A61K 9/5089; A61K 9/5138; A61K 9/5146; A61K 9/5192; A61M 37/0092; B82Y 5/00
See application file for complete search history.

(56) References Cited

U.S. PATENT DOCUMENTS

| | | | |
|---|---|---|---|
| 4,450,150 A | 5/1984 | Sidman | |
| 5,487,390 A * | 1/1996 | Cohen | A61K 9/1271 424/501 |
| 6,649,702 B1 * | 11/2003 | Rapoport | A61K 9/0009 424/486 |
| 6,699,843 B2 | 3/2004 | Pietras et al. | |
| 2003/0118722 A1 * | 6/2003 | Lee et al. | 427/212 |
| 2005/0282233 A1 | 12/2005 | Eriksson et al. | |

(Continued)

FOREIGN PATENT DOCUMENTS

| | | |
|---|---|---|
| KR | 20100013014 | 2/2010 |
| RU | 2413506 | 3/2011 |
| WO | 99/040942 | 8/1999 |

(Continued)

OTHER PUBLICATIONS

Jiang (Journal of Applied Polymer Science (2009) 3472-3478).*

(Continued)

*Primary Examiner* — Anna Falkowitz
(74) *Attorney, Agent, or Firm* — Marshall, Gerstein & Borun LLP

(57) ABSTRACT

Provided herein are nanobubbles designed for use in ultrasound-mediated ablation of cancer cells. The nanobubbles undergo ultrasound-mediated cavitation at an ablation threshold which is significantly decreased, relative to standard ultrasound-mediated treatment of cancer cells. In exemplary embodiments, the nanobubbles comprise an amphiphilic ABC triblock copolymer, wherein block A comprises a hydrophilic polymer, block B comprises a crosslinking polymer, and block C comprises a hydrophobic copolymer comprising (i) methyl methacrylate (MMA) and (ii) a fluorinated monomer, wherein the fluorinated monomer is present in the hydrophobic copolymer of block C at 25 mole percent or less. Related treatment and diagnostic methods, as well as materials relating to the nanobubbles are provided herein. Methods of making a random copolymer are furthermore provided herein.

16 Claims, 36 Drawing Sheets

(56) References Cited

U.S. PATENT DOCUMENTS

2006/0269479 A1 11/2006 Colton et al.
2008/0181853 A1 7/2008 Ottoboni et al.

FOREIGN PATENT DOCUMENTS

| WO | 00/032218   | 6/2000  |
|----|-------------|---------|
| WO | 2004/033036 | 4/2004  |
| WO | 2005/087812 | 9/2005  |
| WO | 2007/133747 | 11/2007 |
| WO | 2007/141411 | 12/2007 |
| WO | 2008/130158 | 10/2008 |

OTHER PUBLICATIONS

Imae et al. ( Colloids and Surfaces A: Physicochemical and Engineering Aspects 167 (2000) 73-81).*
Riess (Prog. Polym Sci 28 (2003) 1107-1170).*
Abuchowski et al., Cancer therapy with chemically modified enzymes. I. Antitumor properties of polyethylene glycol-asparaginase conjugates, Cancer Biochem. Biophys., 7(2):175-86 (1984).
Adjei et al., Pulmonary delivery of peptide drugs: effect of particle size on bioavailability of leuprolide acetate in healthy male volunteers, Pharm. Res., 7(6):565-9 (1990).
Akhtar et al., Prostate-specific membrane antigen-based therapeutics, Adv. Urol., 2012:973820 (2012).
Balogh et al., Significant effect of size on the in vivo biodistribution of gold composite nanodevices in mouse tumor models, Nanomedicine, 3(4):281-96 (2007).
Bander et al., Targeted systemic therapy of prostate cancer With a monoclonal antibody to prostate-specific membrane antigen, Seminars in Oncology, 30:667-77 (2003).
Bartczak et al., Preparation of peptide-functionalized gold nanoparticles using one pot EDC/sulfo-NHS coupling, Langmuir, 27(16):10119-23 (2011).
Bill-Axelson et al., Radical Prostatectomy versus Watchful Waiting in Early Prostate Cancer, N. Engl. J. Med., 352:1977-84 (2005).
Bolla et al., Postoperative radiotherapy after radical prostatectomy: a randomised controlled trial (EORTC trial 22911), Lancet, 366(9485):572-8 (2005).
Borcard et al., Covalent cell surface functionalization of human fetal osteoblasts for tissue engineering, Bioconjug. Chem., 22(7):1422-32 (2011).
Casciani et al., Endorectal and dynamic contrast-enhanced MRI for detection of local recurrence after radical prostatectomy, AJR Am. J. Roentgenol., 190(5):1187-92 (2008).
Chen et al., Bioorthogonal chemistry for site-specific labeling and surface immobilization of proteins, Acc. Chem. Res., 44(9):762-73 (2011).
Chen et al., Synthesis and characterization of silica nanoparticles with well-defined thermoresponsive PNIPAM via a combination of RAFT and click chemistry, ACS Appl. Mater. Interfaces, 3(8):3215-23 (2011).
Cole et al., "The EBV-Hybridoma Technique and Its Application to Human Lunch Cancer" pp. 77-96 IN: Monoclonal Antibodies and Cancer Therapy, New York, NY: Alan R. Liss Inc., (1985).
Comstock et al., A bioluminescent orthotopic mouse model of human osteosarcoma that allows sensitive and rapid evaluation of new therapeutic agents in vivo, In Vivo, 23(5):661-8 (2009).
Cookson et al., Variation in the definition of biochemical recurrence in patients treated for localized prostate cancer: the American Urological Association Prostate Guidelines for Localized Prostate Cancer Update Panel report and recommendations for a standard in the reporting of surgical outcomes, J. Urol., 177(2):540-5 (2007).
Cooperberg et al., The contemporary management of prostate cancer in the United States: Lessons from the Cancer of the Prostate Strategic Urologic Research Endeavor (CaPSURE), a national disease registry, J. Urol., 171(4):1393-401 (2004).

Cote et al., Generation of human monoclonal antibodies reactive with cellular antigens, Proc. Natl. Acad. Sci. USA, 80(7):2026-30 (1983).
Dahl et al., Pathologic outcome of laparoscopic and open radical prostatectomy, Urology, 68(6):1253-6 (2006).
Danquah et al., Micellar delivery of bicalutamide and embelin for treating prostate cancer, Pharm. Res., 26(9):2081-92 (2009).
DeNardo et al., Rationales, evidence, and design considerations for fractionated radioimmunotherapy, Cancer, 94(4 Suppl):1332-48 (2002).
Deshpande et al., Molecular ultrasound imaging: current status and future directions, Clin. Radiol., 65(7):567-81 (2010).
Dhar et al., Targeted delivery of a cisplatin prodrug for safer and more effective prostate cancer therapy in vivo, Proc. Natl. Acad. Sci. USA, 108(5):1850-5 (2011).
Diaz-Lopez et al., Phospholipid decoration of microcapsules containing perfluorooctyl bromide used as ultrasound contrast agents, Biomaterials, 30(8):1462-72 (2009).
Diaz-Lopez et al., The performance of PEGylated nanocapsules of perfluorooctyl bromide as an ultrasound contrast agent, Biomaterials, 31(7):1723-31 (2010).
Dindyal et al., Ultrasound microbubble contrast and current clinical applications, Recent Pat. Cardiovasc. Drug Discov., 6(1):27-41 (2011).
Du et al., Ultrasound-triggered drug release and enhanced anticancer effect of doxorubicin-loaded poly(D,L-lactide-co-glycolide)-methoxy-poly(ethylene glycol) nanodroplets, Ultrasound Med. Biol., 37(8):1252-8 (2011).
Durmaz et al., One-Pot Synthesis of ABC Type Triblock Copolymers via in situ Click [3+2] and Diels?Alder [4+2] Reactions, Macromolecules, 40(2):191-8 (2007).
Eisenbrey et al., Development and optimization of a doxorubicin loaded poly(lactic acid) contrast agent for ultrasound directed drug delivery, J. Control Release, 143(1):38-44 (2010).
Fang et al., Factors and mechanism of "EPR" effect and the enhanced antitumor effects of macromolecular drugs including SMANCS, Adv. Exp. Med. Biol., 419:29-49 (2003).
Ferrara et al., Lipid-shelled vehicles: engineering for ultrasound molecular imaging and drug delivery, Acc. Chem. Res., 42(7):881-92 (2009).
Forsberg et al., Clinical applications of ultrasound contrast agents, Ultrasonics, 36(1-4):695-701 (1998).
Franc et al., Diels-Alder "click" chemistry in designing dendritic macromolecules, Chemistry, 15(23):5630-9 (2009).
Freedland et al., Risk of prostate cancer-specific mortality following biochemical recurrence after radical prostatectomy, JAMA, 294(4):433-9 (2005).
Fu et al., Metastasis suppressor gene Raf kinase inhibitor protein (RKIP) is a novel prognostic marker in prostate cancer, Prostate, 66(3):248-56 (2006).
Gao et al., Drug-loaded nano/microbubbles for combining ultrasonography and targeted chemotherapy, Ultrasonics, 48(4):260-70 (2008).
Gao et al., In vivo cancer targeting and imaging with semiconductor quantum dots, Nat. Biotechnol., 22(8):969-76 (2004).
Gebhart et al., Design and formulation of polyplexes based on pluronic-polyethyleneimine conjugates for gene transfer, Bioconjug. Chem., 13(5):937-44 (2002).
Gold et al., Apatamers as therapeutic and diagnostic agents, J. Biotechnol., 74:5-13 (2000).
Grabski et al., Computerized transrectal ultrasound of the prostate in a multicenter setup (C-TRUS-MS): detection of cancer after multiple negative systematic random and in primary biopsies, World J. Urol., 29(5):573-9 (2011).
Grainger et al., Pulsed ultrasound enhances nanoparticle penetration into breast cancer spheroids, Mol. Pharm., 7(6):2006-19 (2010).
Gref et al., "Stealth" corona-core nanoparticles surface modified by polyethylene glycol (PEG): influences of the corona (PEG chain length and surface density) and of the core composition on phagocytic uptake and plasma protein adsorption, Colloids and Surfaces B: Biointerfaces, 18:301-13 (2000).
Greish et al., Macromolecular therapeutics: advantages and prospects with special emphasis on solid tumour targeting, Clin. Pharmacokinet., 42(13):1089-105 (2003).

(56) References Cited

OTHER PUBLICATIONS

Grishenkov et al., Characterization of acoustic properties of PVA-shelled ultrasound contrast agents: linear properties (part I), Ultrasound Med. Biol., 35(7):1127-38 (2009).
Grishenkov et al., Characterization of acoustic properties of PVA-shelled ultrasound contrast agents: ultrasound-induced fracture (part II), Ultrasound Med. Biol., 35(7):1139-47 (2009).
Grishenkov et al., In vitro contrast-enhanced ultrasound measurements of capillary microcirculation: comparison between polymer- and phospholipid-shelled microbubbles, Ultrasonics, 51(1):40-8 (2011).
Guo et al., Aptamer-functionalized PEG-PLGA nanoparticles for enhanced anti-glioma drug delivery, Biomaterials, 32(31):8010-20 (2011).
Haddleton et al., Atom Transfer Polymerization of Methyl Methacrylate Mediated by Alkylpyridylmethanimine Type Ligands, Copper(I) Bromide, and Alkyl Halides in Hydrocarbon Solution, Macromolecules, 32(7):2110-9 (1999).
Hadinoto et al., Hollow spherical nanoparticulate aggregates as potential ultrasound contrast agent: shell thickness characterization, Drug Dev. Ind. Pharm., 35(10):1167-79 (2009).
Hadinoto, Mechanical stability of hollow spherical nano-aggregates as ultrasound contrast agent, Int. J. Pharm., 374(1-2):153-61 (2009).
Haider et al., Dynamic contrast-enhanced magnetic resonance imaging for localization of recurrent prostate cancer after external beam radiotherapy, Int. J. Radiat. Oncol. Biol. Phys., 70(2):425-30 (2008).
Hall et al., Histotripsy of the prostate: dose effects in a chronic canine model, Urology, 74(4):932-7 (2009).
Hempel et al., Histotripsy fractionation of prostate tissue: local effects and systemic response in a canine model, J. Urol., 185(4):1484-9 (2011).
Heneweer et al., Magnitude of enhanced permeability and retention effect in tumors with different phenotypes: 89Zr-albumin as a model system, J. Nucl. Med., 52(4):625-33 (2011).
Hsiao et al., Microfluidic system for formation of PC-3 prostate cancer co-culture spheroids, Biomaterials, 30(16):3020-7 (2009).
Hu et al., The effect of postprostatectomy external beam radiotherapy on quality of life: results from the Cancer of the Prostate Strategic Urologic Research Endeavor, Cancer, 107(2):281-8 (2006).
Hugosson et al., Radical retropubic prostatectomy: a review of outcomes and side-effects, Acta Oncol., 50 Suppl 1:92-7 (2011).
International Search Report and Written Opinion, International Application No. PCT/US2012/059556, mailed Feb. 7, 2013.
International Preliminary Report on Patentability, International Application No. PCT/US2012/059556, dated Apr. 15, 2014.
Iyer et al., Exploiting the enhanced permeability and retention effect for tumor targeting, Drug Discov. Today, 11(17-18):812-8 (2006).
Jiang, Preparation of liquid-filled micelles based on an amphiphilic triblock copolymer, J. Appl. Polymer Sci., 114(6):3472-8 (2009).
Kandadai et al., Comparison of surfactants used to prepare aqueous perfluoropentane emulsions for pharmaceutical applications, Langmuir, 26(7):4655-60 (2010).
Katz et al., Predictors of biochemical outcome with salvage conformal radiotherapy after radical prostatectomy for prostate cancer, J. Clin. Oncol., 21(3):483-9 (2003).
Kawashima et al., Pulmonary delivery of insulin with nebulized DL-lactide/glycolide copolymer (PLGA) nanospheres to prolong hypoglycemic effect, J. Control. Release, 62(1-2):279-87 (1999).
Kieran et al., Refining histotripsy: defining the parameter space for the creation of nonthermal lesions with high intensity, pulsed focused ultrasound of the in vitro kidney, J. Urol., 178(2):672-6 (2007).
Klein et al., Surgeon experience is strongly associated with biochemical recurrence after radical prostatectomy for all preoperative risk categories, J. Urol., 179(6):2212-6 (2008).
Kortt et al., Dimeric and trimeric antibodies: high avidity scFvs for cancer targeting, Biomol. Eng., 18(3):95-108 (2001).
Kozbor et al., The production of monoclonal antibodies from human lymphocytes, Immunol. Today, 4(3):72-9 (1983).
Kripfgans et al., Acoustic droplet vaporization for therapeutic and diagnostic applications, Ultrasound Med. Biol., 26(7):1177-89 (2000).
Krupka et al., Formulation and characterization of echogenic lipid-Pluronic nanobubbles, Mol. Pharm., 7(1):49-59 (2010).
Lake et al., Histotripsy: minimally invasive technology for prostatic tissue ablation in an in vivo canine model, Urology, 72(3):682-6 (2008).
Li et al., In vitro and preclinical targeted alpha therapy of human prostate cancer with Bi-213 labeled J591 antibody against the prostate specific membrane antigen, Prostate Cancer Prostatic Dis., 5(1):36-46 (2002).
Li et al., Synthesis and characterization of amphiphilic lipopolymers for micellar drug delivery, Biomacromolecules, 11(10):2610-20 (2010).
Lin et al., Degradable, pH-sensitive, membrane-destabilizing, comb-like polymers for intracellular delivery of nucleic acids, Biomaterials, 31(27):7150-66 (2010).
Lindner, Evolving applications for contrast ultrasound, Am. J. Cardiol., 90(10A):72J-80J (2002).
Liu et al., Encapsulated ultrasound microbubbles: therapeutic application in drug/gene delivery, J. Control Release, 114(1):89-99 (2006).
Liu et al., Pulmonary delivery of free and liposomal insulin, Pharm. Res., 10(2):228-32 (1993).
Maeda et al., Enhanced vascular permeability in solid tumor is mediated by nitric oxide and inhibited by both new nitric oxide scavenger and nitric oxide synthase inhibitor, Jpn. J. Cancer Res., 85(4):331-4 (1994).
Maeda et al., Tumoritropic and lymphotropic principles of macromolecular drugs, Crit. Rev. Ther. Drug Carrier Syst., 6(3):193-210 (1989).
Mandarano et al., Biomed. Imaging Interv. J., 6:e13 (2010).
Mannucci, Hemostatic drugs, N. Engl. J. Med., 339(4):245-53 (1998).
Mantovani et al., Design and Synthesis of N-Maleimido-Functionalized Hydrophilic Polymers via Copper-Mediated Living Radical Polymerization: A Suitable Alternative to PEGylation Chemistry, J. Am. Chem. Soc., 127(9):2966-73 (2005).
Marmottant et al., Buckling resistance of solid shell bubbles under ultrasound, J. Acoust. Soc. Am., 129(3):1231-9 (2011).
Matyjaszewski, Atom Transfer Radical Polymerization (ATRP): Current Status and Future Perspectives, Macromolecules 45(10):4015-39 (2012).
Maxwell et al., A tissue phantom for visualization and measurement of ultrasound-induced cavitation damage, Ultrasound Med. Biol., 36(12):2132-43 (2010).
Michalski et al., Development of RTOG consensus guidelines for the definition of the clinical target volume for postoperative conformal radiation therapy for prostate cancer, Int. J. Radiat. Oncol. Biol. Phys., 76(2):361-8 (2010).
Miller et al., Long-term outcomes among localized prostate cancer survivors: health-related quality-of-life changes after radical prostatectomy, external radiation, and brachytherapy, J. Clin. Oncol., 23(12):2772-80 (2005).
Min et al., Dual-aptamer-based delivery vehicle of doxorubicin to both PSMA (+) and PSMA (−) prostate cancers, Biomaterials, 32(8):2124-32 (2011).
Moinpour et al., Health-related quality of life results in pathologic stage C prostate cancer from a Southwest Oncology Group trial comparing radical prostatectomy alone with radical prostatectomy plus radiation therapy, J. Clin. Oncol., 26(1):112-20 (2008).
Moman et al., Focal salvage guided by T2-weighted and dynamic contrast-enhanced magnetic resonance imaging for prostate cancer recurrences, Int. J. Radiat. Oncol. Biol. Phys., 76(3):741-6 (2010).
Nakajima et al., Targeted, activatable, in vivo fluorescence imaging of prostate-specific membrane antigen (PSMA) positive tumors using the quenched humanized J591 antibody-indocyanine green (ICG) conjugate, Bioconjug. Chem., 22(8):1700-5 (2011).
Nam et al., Controlling coupling reaction of EDC and NHS for preparation of collagen gels using ethanol/water co-solvents, Macromol. Biosci., 8(1):32-7 (2008).

(56) References Cited

OTHER PUBLICATIONS

Nestor et al., Preparation and in vitro evaluation of poly(D,L-lactide-co-glycolide) air-filled nanocapsules as a contrast agent for ultrasound imaging, Ultrasonics, 51(7):839-45 (2011).
Nimmo et al., Diels-Alder Click cross-linked hyaluronic acid hydrogels for tissue engineering, Biomacromolecules, 12(3):824-30 (2011).
O'Donoghue et al., Relationships between tumor size and curability for uniformly targeted therapy with beta-emitting radionuclides, J. Nucl. Med., 36(10):1902-9 (1995).
Oeffinger et al., Development and characterization of a nano-scale contrast agent, Ultrasonics, 42(1-9):343-7 (2004).
Okuda et al., PEGylated lysine dendrimers for tumor-selective targeting after intravenous injection in tumor-bearing mice, J. Control Release, 116(3):330-6 (2006).
Parsons et al., Pulsed cavitational ultrasound therapy for controlled tissue homogenization, Ultrasound Med. Biol., 32(1):115-29 (2006).
Phillips et al., Acoustic backscatter properties of the particle/bubble ultrasound contrast agent, Ultrasonics, 36(8):883-92 (1998).
Pisani et al., Surfactant dependent morphology of polymeric capsules of perfluorooctyl bromide: influence of polymer adsorption at the dichloromethane-water interface, J. Colloid Interface Sci., 326(1):66-71 (2008).
Platts et al., Contrast echocardiography in critical care: echoes of the future? A review of the role of microsphere contrast echocardiography, Crit. Care Resusc., 13(1):44-55 (2011).
Poortmans et al., Guidelines for target volume definition in post-operative radiotherapy for prostate cancer, on behalf of the EORTC Radiation Oncology Group, Radiother. Oncol., 84(2):121-7 (2007).
Pound et al., Natural history of progression after PSA elevation following radical prostatectomy, JAMA, 281(17):1591-7 (1999).
Qi et al., Developing visible fluorogenic 'click-on' dyes for cellular imaging, Bioconjug. Chem., 22(9):1758-62 (2011).
Qian et al., Pulmonary delivery of a GLP-1 receptor agonist, BMS-686117, Int. J. Pharm., 366(1-2):218-20 (2009).
Qian et al., Sustained release subcutaneous delivery of BMS-686117, a GLP-1 receptor peptide agonist, via a zinc adduct, Int. J. Pharm., 374(1-2):46-52 (2009).
Rajender Reddy et al., Use of peginterferon alfa-2a (40 KD) (Pegasys) for the treatment of hepatitis C, Adv. Drug Deliv. Rev., 54(4):571-86 (2002).
Raldow et al., Salvage external beam radiotherapy for prostate cancer after radical prostatectomy: current status and controversy, Oncology (Williston Park), 24(8):692-700 (2010).
Rapoport et al., Microbubble generation in phase-shift nanoemulsions used as anticancer drug carriers, Bubble Sci. Eng. Technol., 1(1-2):31-9 (2009).
Rapoport et al., Multifunctional nanoparticles for combining ultrasonic tumor imaging and targeted chemotherapy, J. Natl. Cancer Inst., 99(14):1095-106 (2007).
Reiss et al., Micellization of block copolymers, Prog. Polym. Sci., 28:1107-70 (2003).
Reiter et al., Engineering interchain disulfide bonds into conserved framework regions of Fv fragments: improved biochemical characteristics of recombinant immunotoxins containing disulfide-stabilized Fv, Protein Engineering Design & Selection, 7(5):697-704 (1994).
Roberts et al., Pulsed cavitational ultrasound: a noninvasive technology for controlled tissue ablation (histotripsy) in the rabbit kidney, J. Urol., 175(2):734-8 (2006).
Roehl et al., Cancer progression and survival rates following anatomical radical retropubic prostatectomy in 3,478 consecutive patients: long-term results, J. Urol., 172(3):910-4 (2004).
Rouviere et al., Recurrent prostate cancer after external beam radiotherapy: value of contrast-enhanced dynamic MRI in localizing intraprostatic tumor—correlation with biopsy findings, Urology, 63(5):922-7 (2004).
Saar et al., Experimental orthotopic prostate tumor in nude mice: Techniques for local cell inoculation and three-dimensional ultrasound monitoring, Urol. Oncol., 30(3):330-8 (2012).
Sletten et al., From mechanism to mouse: a tale of two bioorthogonal reactions, Acc. Chem. Res., 44(9):666-76 (2011).
Soman et al., Synthesis and characterization of stable fluorocarbon nanostructures as drug delivery vehicles for cytolytic peptides, Nano Lett., 8(4):1131-6 (2008).
Stephenson et al., Predicting the outcome of salvage radiation therapy for recurrent prostate cancer after radical prostatectomy, J. Clin. Oncol., 25(15):2035-41 (2007).
Swanson et al., Pathologic findings at radical prostatectomy: risk factors for failure and death, Urol. Oncol., 25(2):110-4 (2007).
Tagawa et al., Genomic DNA with transformation-related activity and melanoma antigen expression, J. Invest. Dermatol., 92(5 Suppl):284S-8S (1989).
Tagawa, Phase I trial of fractionated-dose 177lutetium radiolabeled anti-prostatespecific membrane antigen (PSMA) monoclonal antibody J591 (177Lu-J591) in patients (pts) with metastatic castrationresistant prostate cancer (metCRPC), J. Clin. Oncol., 28, Abstract No. 4667 (2010).
Teesalu et al., C-end rule peptides mediate neuropilin-1-dependent cell, vascular, and tissue penetration, Proc. Natl. Acad. Sci. USA, 106(38):16157-62 (2009).
Thompson et al., Adjuvant radiotherapy for pathological T3N0M0 prostate cancer significantly reduces risk of metastases and improves survival: long-term followup of a randomized clinical trial, J. Urol., 181(3):956-62 (2009).
Todorovska et al., Design and application of diabodies, triabodies and tetrabodies for cancer targeting, J. Immunol. Methods, 248(1-2):47-66 (2001).
Trevena, Cavitation and the generation of tension in liquids, J. Physics D (Applied Physics), 17:2139-64 (1984).
Trock et al., Prostate cancer-specific survival following salvage radiotherapy vs observation in men with biochemical recurrence after radical prostatectomy, JAMA, 299(23):2760-9 (2008).
Uesugi et al., An ultrasound-responsive nano delivery system of tissue-type plasminogen activator for thrombolytic therapy, J. Control Release, 147(2):269-77 (2010).
Underwood et al., Racial treatment trends in localized/regional prostate carcinoma: 1992-1999, Cancer, 103(3):538-45 (2005).
van der Wielen et al., Erectile dysfunction after radiotherapy for prostate cancer and radiation dose to the penile structures: a critical review, Radiother. Oncol., 84(2):107-13 (2007).
Vis et al., The actual value of the surgical margin status as a predictor of disease progression in men with early prostate cancer, Eur. Urol., 50(2):258-65 (2006).
Wang et al., Active focal zone sharpening for high-precision treatment using histotripsy, IEEE Trans. Ultrason. Ferroelectr. Freq. Control., 58(2):305-15 (2011).
Wheatley et al., Nano-sized ultrasound contrast agent: salting-out method, Mol. Imaging, 9(2):96-107 (2010).
Wiegel et al., Phase III postoperative adjuvant radiotherapy after radical prostatectomy compared with radical prostatectomy alone in pT3 prostate cancer with postoperative undetectable prostate-specific antigen: ARO 96-02/AUO AP 09/95, J. Clin. Oncol., 27(18):2924-30 (2009).
Wildling et al., Linking of sensor molecules with amino groups to amino-functionalized AFM tips, Bioconjug. Chem., 22(6):1239-48 (2011).
Wiltshire et al., Anatomic boundaries of the clinical target vol. (prostate bed) after radical prostatectomy, Int. J. Radiat. Oncol. Biol. Phys., 69(4):1090-9 (2007).
Xing et al., Novel ultrasound contrast agent based on microbubbles generated from surfactant mixtures of Span 60 and polyoxyethylene 40 stearate, Acta Biomater., 6(9):3542-9 (2010).
Xu et al., A new strategy to enhance cavitational tissue erosion using a high-intensity, Initiating sequence, IEEE Trans. Ultrason. Ferroelectr. Freq. Control., 53(8):1412-24 (2006).
Xu et al., Controlled ultrasound tissue erosion: the role of dynamic interaction between insonation and microbubble activity, J. Acoust. Soc. Am., 177(1):424-35 (2005).
Xu et al., Evolution of bubble clouds induced by pulsed cavitational ultrasound therapy—histotripsy, IEEE Trans. Ultrason. Ferroelectr. Freq. Control., 55(5):1122-32 (2008).

(56) References Cited

OTHER PUBLICATIONS

Xu et al., High speed imaging of bubble clouds generated in pulsed ultrasound cavitational therapy—histotripsy, IEEE Trans. Ultrason. Ferroelectr. Freq. Control., 54(10):2091-101 (2007).

Xu et al., Optical and acoustic monitoring of bubble cloud dynamics at a tissue-fluid interface in ultrasound tissue erosion, J. Acoust. Soc. Am., 121(4):2421-30 (2007).

Yakar et al., Feasibility of 3T dynamic contrast-enhanced magnetic resonance-guided biopsy in localizing local recurrence of prostate cancer after external beam radiation therapy, Invest. Radiol., 45(3):121-5 (2010).

Yu et al., Bio-distribution and anti-tumor efficacy of PEG/PLA nano particles loaded doxorubicin, J. Drug Target., 15(4):279-84 (2007).

Yu et al., Epidermal growth factor-PEG functionalized PAMAM-pentaethylenehexamine dendron for targeted gene delivery produced by click chemistry, Biomacromolecules, 12(6):2039-47 (2011).

Zhang et al., In vivo real-time imaging of TGF-beta-induced transcriptional activation of the RANK ligand gene promoter in intraosseous prostate cancer, Prostate, 59(4):360-9 (2004).

Zheng et al., Chitosan-g-MPEG-modified alginate/chitosan hydrogel microcapsules: a quantitative study of the effect of polymer architecture on the resistance to protein adsorption, Langmuir, 26(22):17156-64 (2010).

\* cited by examiner

POLYMERIC NANOPARTICLES FOR ULTRASOUND IMAGING AND THERAPY

CROSS-REFERENCE TO RELATED APPLICATIONS

This application claims priority to U.S. Provisional Application No. 61/545,418, filed Oct. 10, 2011, and U.S. Provisional Application No. 61/545,898, filed Oct. 11, 2011, each of which is incorporated by reference in its entirety.

BACKGROUND

The American Cancer Society predicted that 240,890 new men will be diagnosed with prostate cancer in 2011 and another 33,720 men will die of this disease, which makes prostate cancer the second leading cause of cancer related death in men in the United States.[1] Surgical removal of the prostate gland and pelvic lymph nodes, which is known as radical prostatectomy (RP) provides excellent control for clinically localized prostate cancer.[2] However, one-third of prostate cancer patients undergoing RP show positive surgical margins, another 9% will have seminal vesicle invasion, and one-third show extracapsular extension,[3-6] which are pathological risk factors for cancer recurrence. Indeed, 40%-50% of high risk patients show biochemical recurrence (i.e. serum concentration of prostate specific antigen (PSA) is ≥0.2 ng/mL)[7] after RP and many of those patients develop metastases.[8-13]

Recent investigations have shown therapeutic benefits in applying radiation therapy locally to the prostate fossa in patients showing biochemical recurrence after RP, which is known as salvage radiotherapy (SRT).[14-16] A retrospective analysis of 635 prostate cancer patients who either received SRT alone (n=160), SRT combined with hormonal therapy (n=78), or no salvage treatment (n=397) showed a 10-year prostate cancer-specific survival rate of 86% in patients treated with SRT compared to a survival rate of 62% in patients who were not treated with SRT indicating a 3-fold increase in prostate cancer-specific survival in repose to local SRT.[16] Another retrospective analysis used a cohort of 1,540 prostate cancer patients to develop a model to predict biochemical control of prostate cancer after SRT,[15] which clearly showed that 60%-70% of patients with recurrent prostate cancer develop metastasis within 6 years if they do not receive SRT.[17] These data evidence that local ablation of recurrent prostate cancer cells using SRT alters the natural course of the disease and prevent its metastatic spread.

Clinical guidelines for SRT advocate the treatment of the vesicourethral anastomosis and the surrounding periurethral tissues but differ as to the volume of the bladder and seminal vesicle beds that should be irradiated.[18-20] Consequently, SRT is routinely applied to large tissue volumes centered around the prostatic fossa,[21-23] which results in multiple acute and delayed toxicities such as diarrhea, proctitis, cystitis, urethral strictures, urinary urgency, and rectal complications.[22,24,25] Furthermore, patients who received SRT after RP experienced worse sexual functioning compared to those who had RP alone, which is probably due to radiation damage of the vascular structure of the penis.[26-28] Collectively, these studies indicate the therapeutic benefit of local ablation of recurrent prostate cancer cells as an effective strategy to suppress the development of the metastatic disease but also demonstrate the need for achieving selective eradication of prostate cancer cells without damaging neighboring healthy tissue.

SUMMARY

The present invention aims to provide new nano-sized particles (e.g., nanobubbles, nanodroplets) for imaging and therapy. The nano-sized particles of the invention "recognize" and bind to cancer cells, e.g., prostate cancer cells, to provide sensitive, real-time, in vivo imaging of local microscopic cancer lesions, as well as selective ablation of the same, when used with non-invasive therapeutic ultrasound (US). In exemplary aspects, the nano-sized particles of the invention are nanobubbles that undergo ultrasound-mediated cavitation at an ablation threshold which is significantly decreased, relative to standard ultrasound-mediated treatment of cancer cells.

The invention provides a nano-sized particle, e.g., a nanobubble, a nanodroplet, comprising an amphiphilic ABC triblock copolymer. In exemplary aspects, the triblock copolymer comprises block A comprises a hydrophilic polymer, block B comprises a crosslinking polymer, and block C comprises a hydrophobic copolymer comprising (i) methyl methacrylate (MMA) and (ii) a fluorinated monomer. In exemplary aspects, the fluorinated monomer of block C is present in the hydrophobic copolymer of block C at 25 mole percent or less.

The invention also provides a nano-sized particle, e.g., a nanobubble, a nanodroplet, which is produced from micellization of an amphiphilic ABC triblock copolymer. In exemplary aspects, the triblock copolymer comprises block A comprises a hydrophilic polymer, block B comprises a crosslinking polymer, and block C comprises a hydrophobic copolymer comprising (i) methyl methacrylate (MMA) and (ii) a fluorinated monomer. In exemplary aspects, the fluorinated monomer of block C is present in the hydrophobic copolymer of block C at 25 mole percent or less.

The invention further provides a method of treating cancer in a subject. In exemplary aspects, the method comprises the steps of administering to the subject (i) a nano-sized particle, e.g., a nanobubble, a nanodroplet, of the invention and (ii) ultrasound, in an amount effective to treat the cancer in the subject.

Furthermore provided is a method of determining the presence of a cancer cell in a subject. In exemplary aspects, the method comprises the steps of administering to the subject (i) a nano-sized particle, e.g., a nanobubble, a nanodroplet, of the invention, wherein the nanobubble comprises (a) a cancer cell-targeting ligand which binds to a marker of the cancer cell and (b) an ultrasound contrast agent, and (ii) ultrasound.

The invention also provides a method of diagnosing, staging, monitoring, or prognosing a cancer in a subject. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound.

The invention further provides a method of determining a subject's need for anti-cancer treatment, a method of determining efficacy of an anti-cancer treatment in a subject, a method of screening a compound for anti-cancer therapeutic activity. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound.

The invention furthermore provides a method of determining a subject's risk for cancer and a method of monitoring a subject's risk for cancer. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound.

The invention moreover provides a random copolymer comprising monomers of methyl methacrylate (MMA) and monomers of hexadecafluorodecylmethacrylate (HDFMA), wherein the mole ratio of the monomers of MMA to the monomers of HDFMA is between about 80 and 95.

A method of making a random copolymer comprising monomers of methyl methacrylate (MMA) and monomers of hexadecafluorodecylmethacrylate (HDFMA) is also provided herein. In exemplary aspects, the method comprises introducing into a Schlenk tube under argon CuBr, N-(n-Pentyl)-2-pyridylmethanimine, a protected maleimide functional initiator, MMA, HDFMA and toluene. Random copolymers made by this method are also provided herein.

Block copolymers comprising a block of the random copolymer of the invention, as well as amphiphilic block copolymers, are moreover provided herein. Related nanoparticles, e.g., nanobubbles, nanodroplets, kits comprising the same, and pharmaceutical compositions, are further provided by the invention.

Figure 4A:
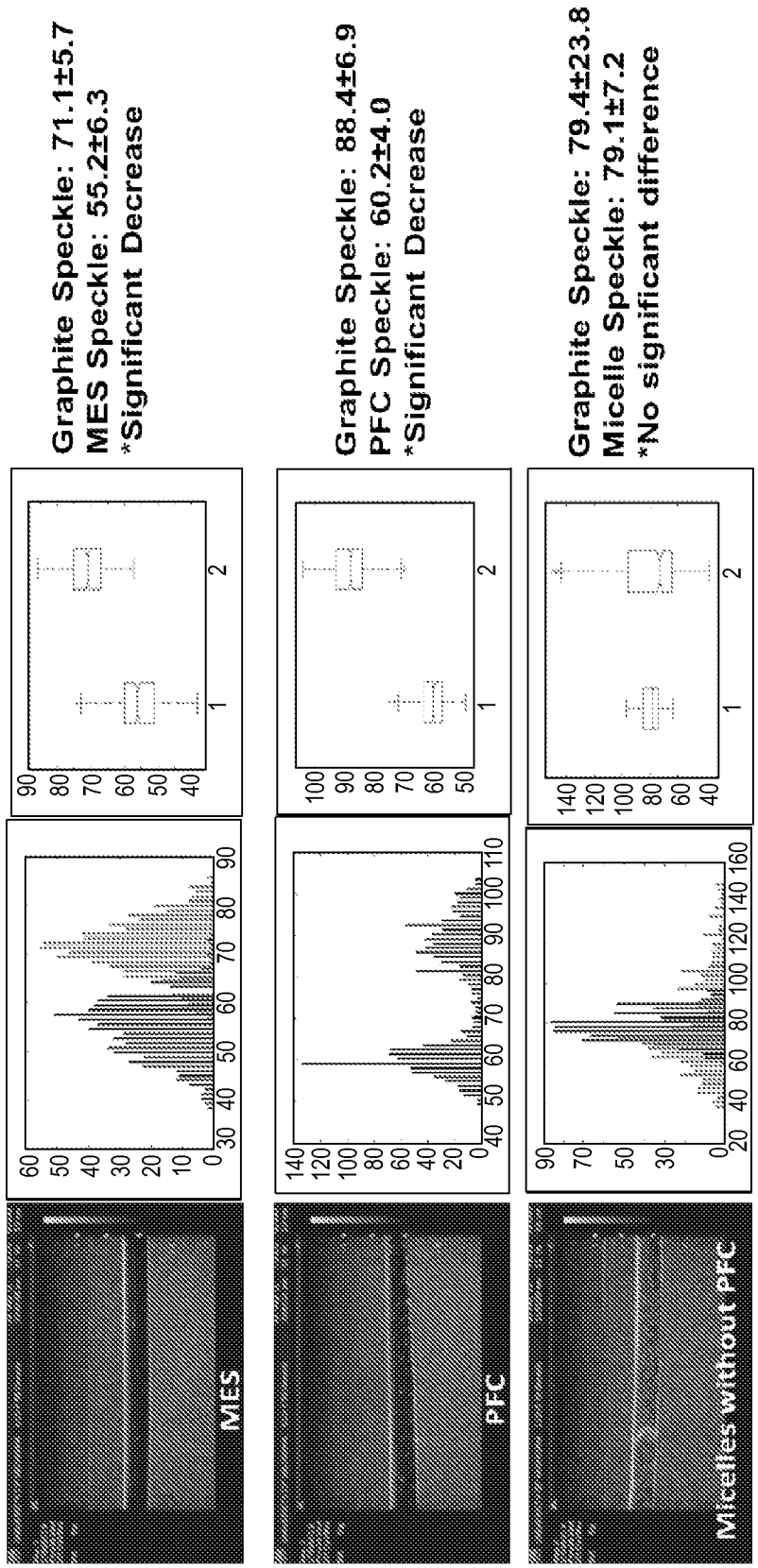
Figure 4B:
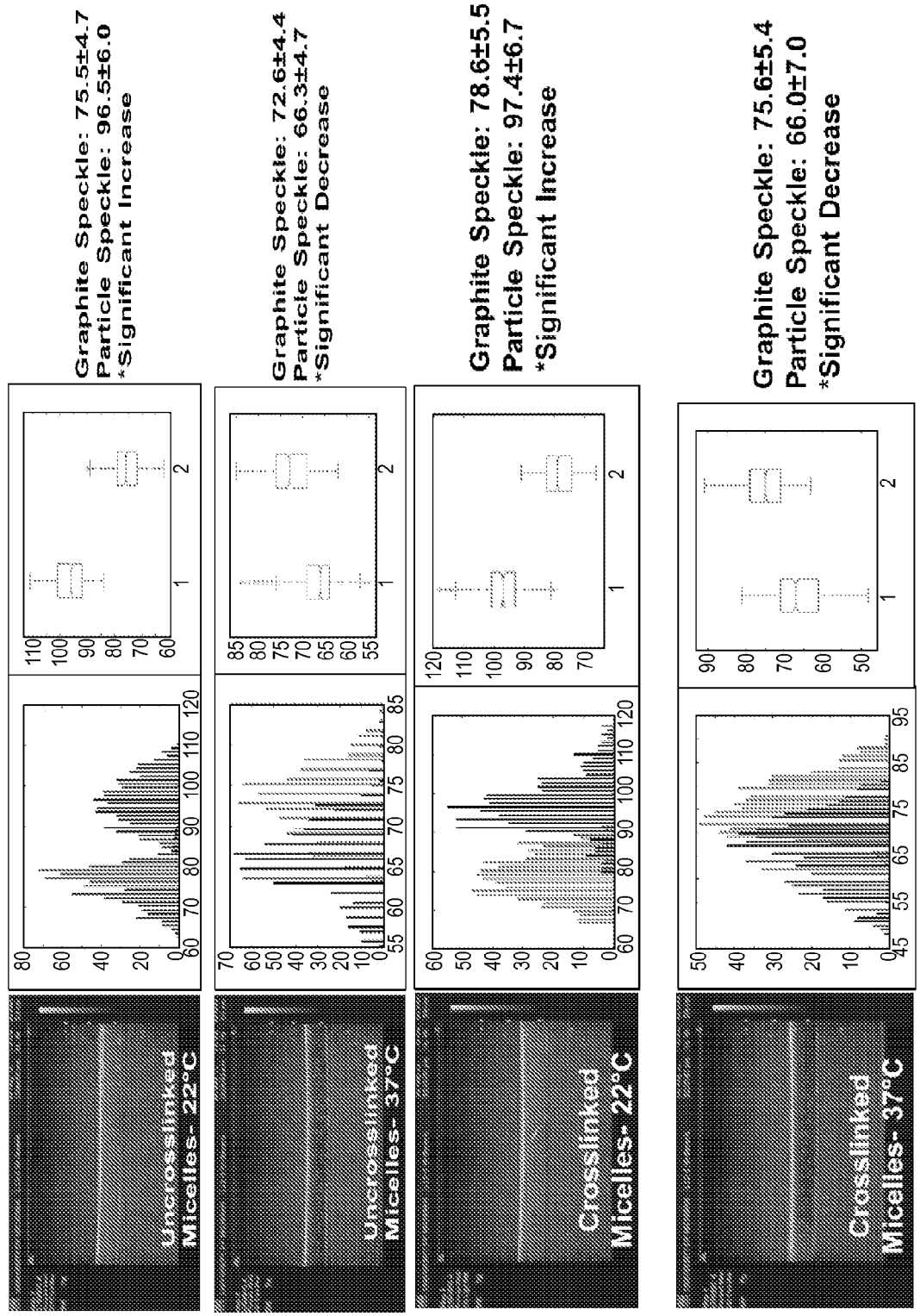

Each of FIGS. 4A and 4B is a set of sample ultrasound images of vessel phantoms filled with MES, PFC, miclelles solution without PFC, and nano-bubbles solution and the corresponding histogram for the ROI.

Figure 4C:
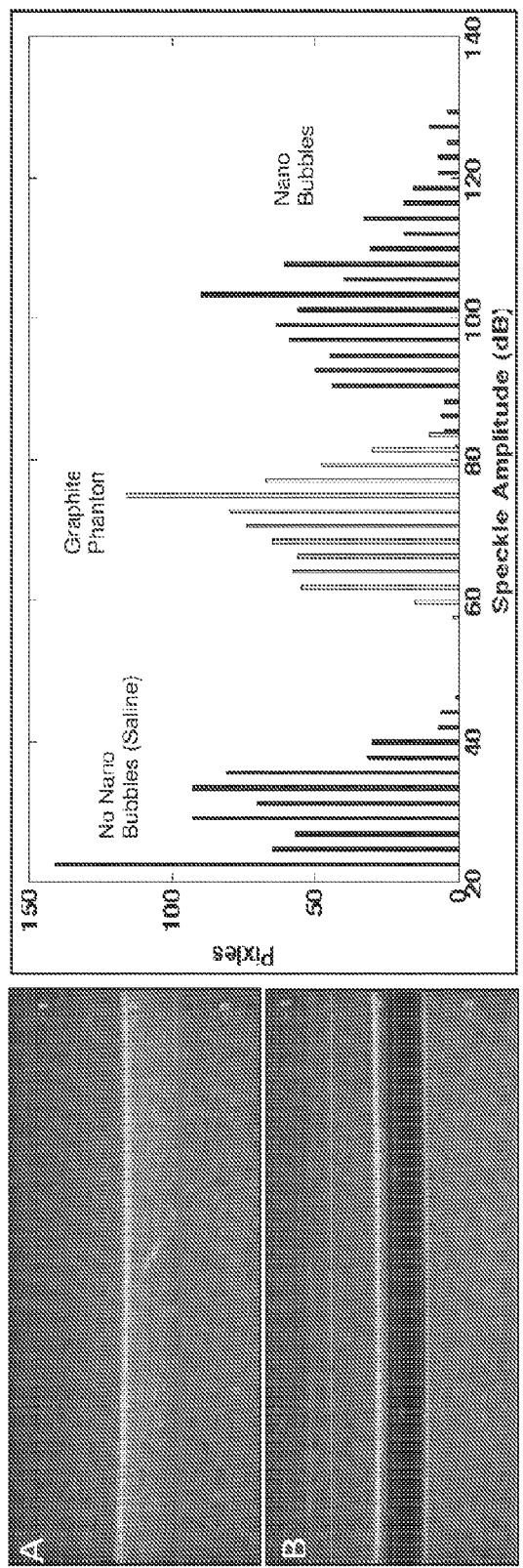

FIG. 4C is a set of images representing sample ultrasound images of vessel phantoms filled with (A) nano-bubbles solution and (B) blank PBS and the corresponding histogram for the ROI. B-scan images are displayed on a 170 dB dynamic range scale showing a significant increase in the backscatter amplitude of the nano-bubbles compared to PBS.

Figure 5:
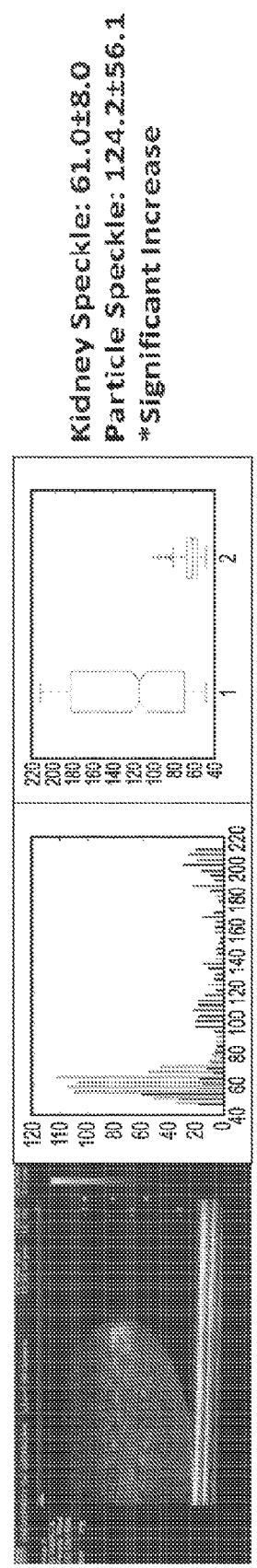

FIG. 5 is a collection of images representing ultrasound imaging of porcine kidney injected nanobubbles and corresponding histogram for the ROI.

Figure 6:
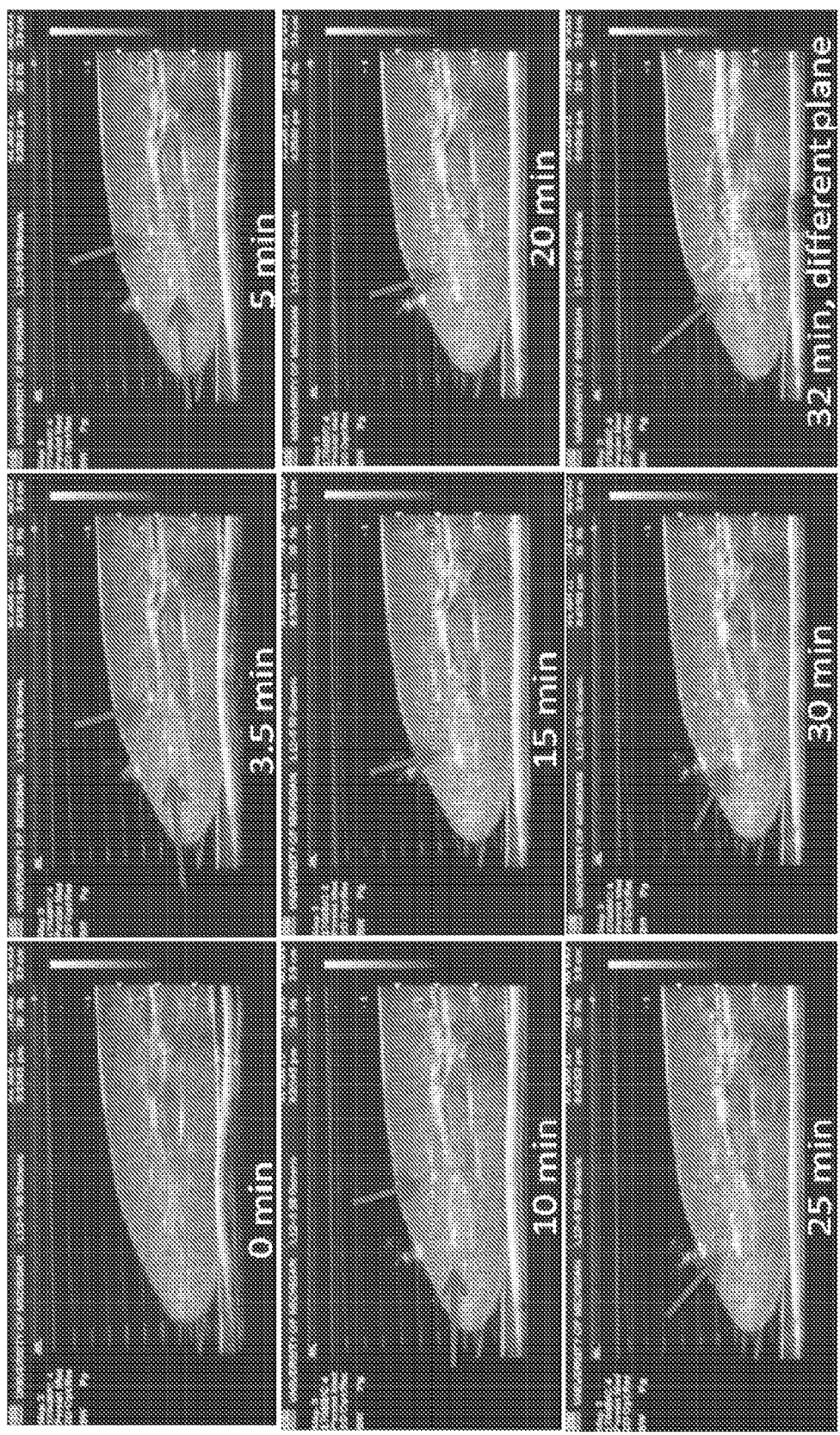

FIG. 6 is a collection of US images of porcine kidney infected nano-bubbles at 37° C. for 30 min to test stability of nano-bubbles.

Figure 7A:
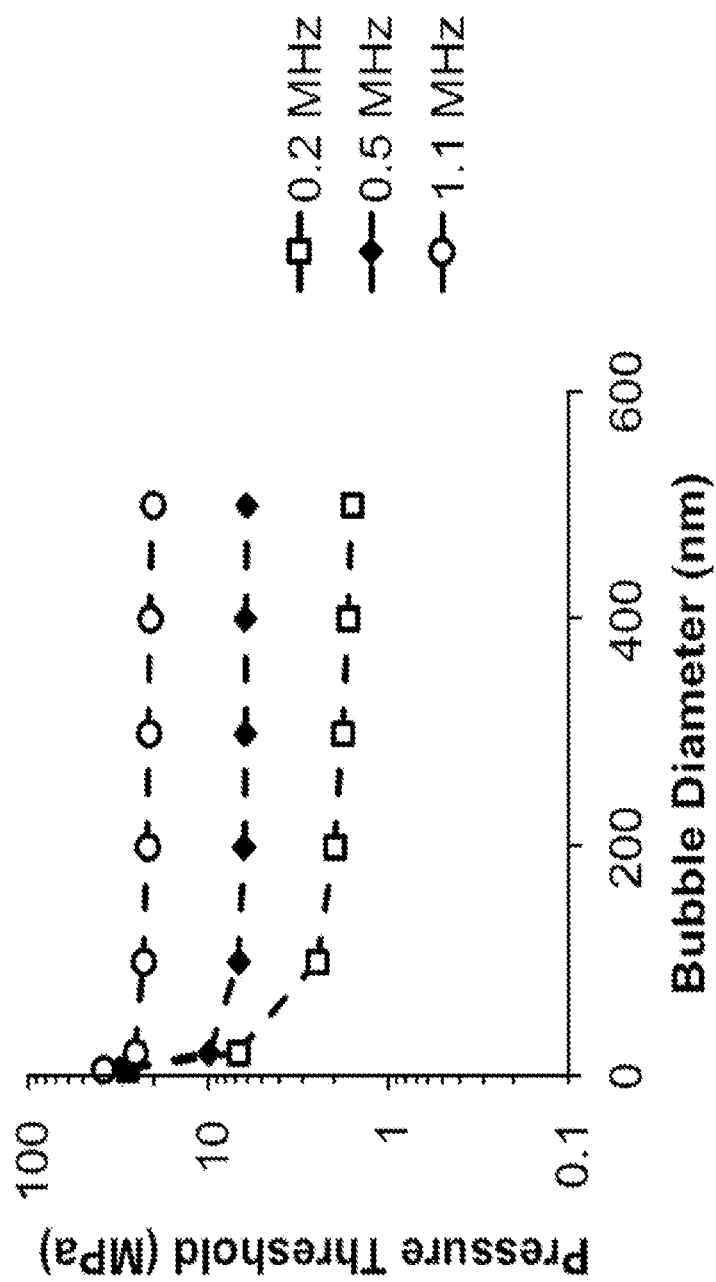

FIG. 7A is a graph of the nanobubble diameter vs. simulated pressure threshold. Simulated pressure threshold to expand a nano-bubble (size=100-500 nm) to reach 50 μm at 0.2, 0.5 and 1.1 MHz. A 0.050 Pa-s viscosity coefficient is used, which is within the viscosity range of soft tissues.

Figure 7B:
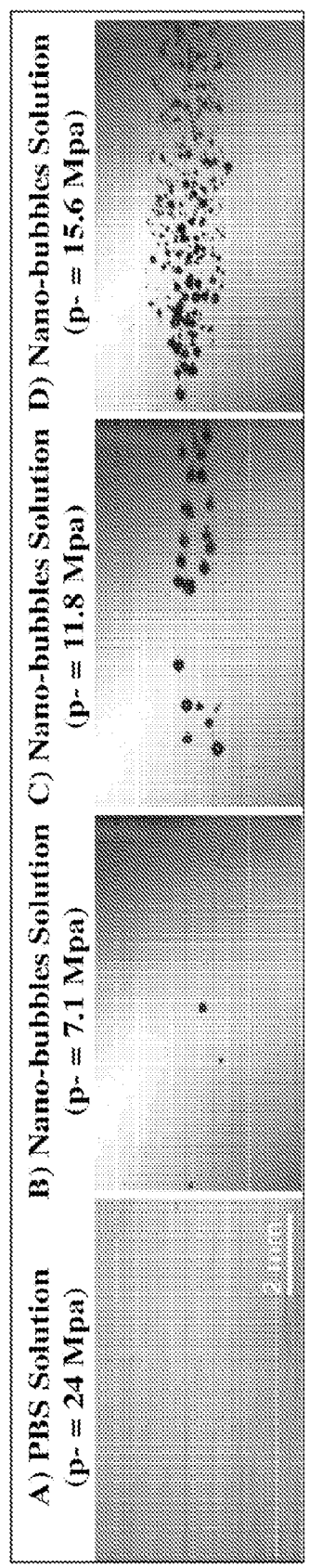

FIG. 7B is a set of images of degassed PBS (A) and nanobubble (B-D) solutions exposed to a 1-cycle histotripsy pulse at 500 kHz. Bubbles appear dark on backlit images taken by high speed camera.

Figure 7C:
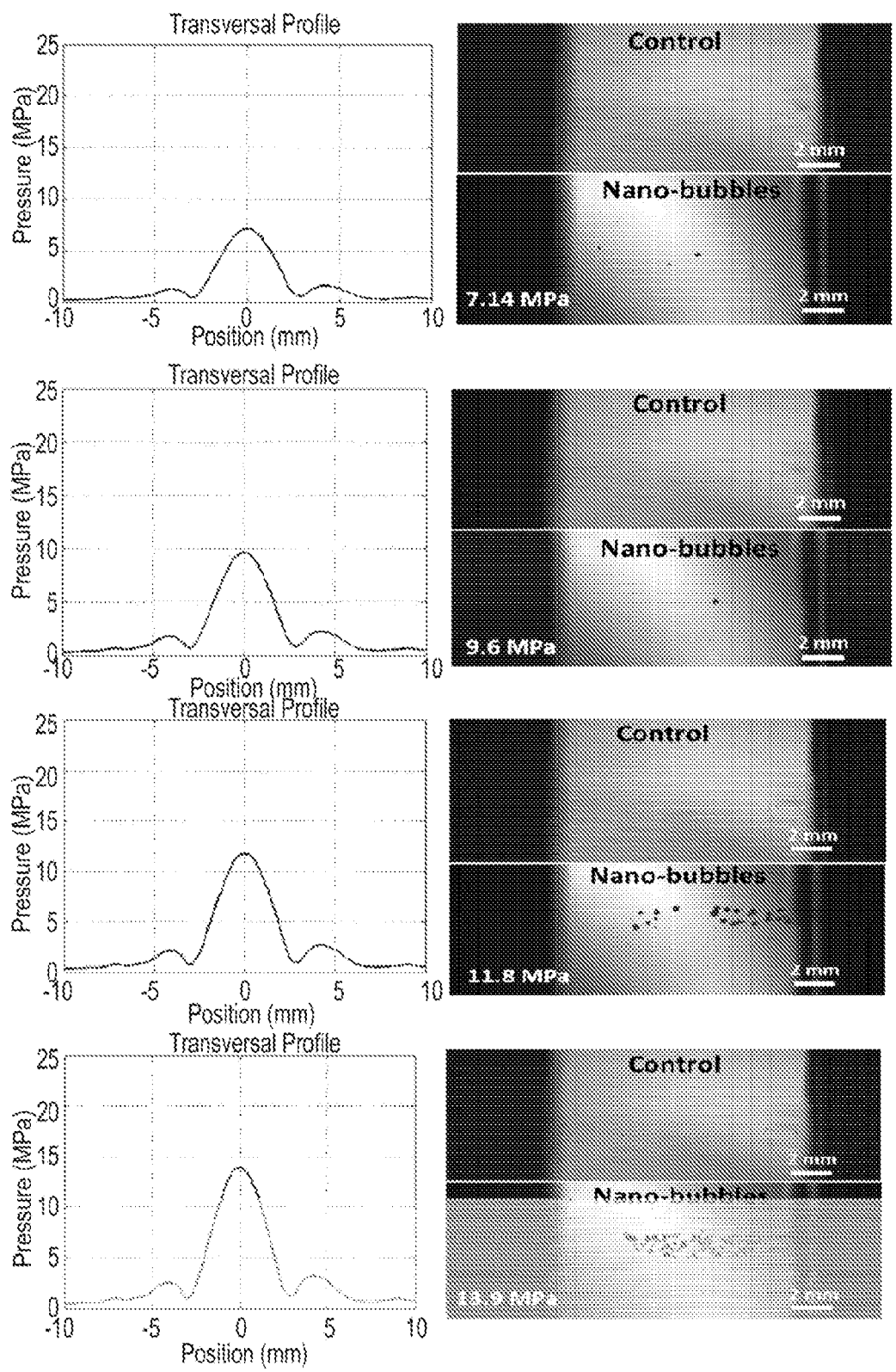
Figure 7D:
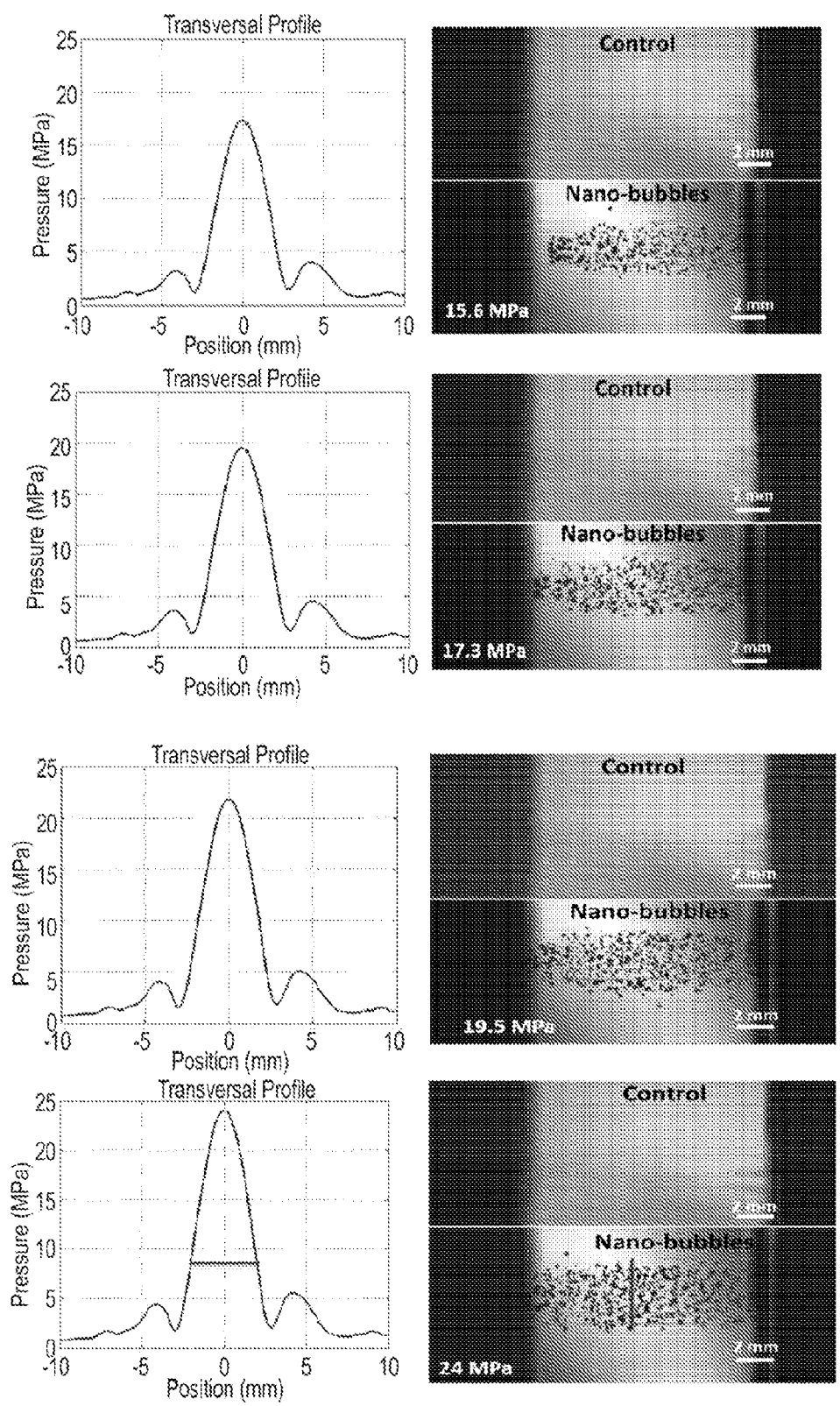

Each of FIGS. 7C and 7D is a collection of images of degassed PBS (A) and nano-bubble (B-D) solutions exposed to a 1-cycle histotripsy pulse at 500 kHz. Bubbles appear dark on backlit images taken by high speed camera.

Figure 8:
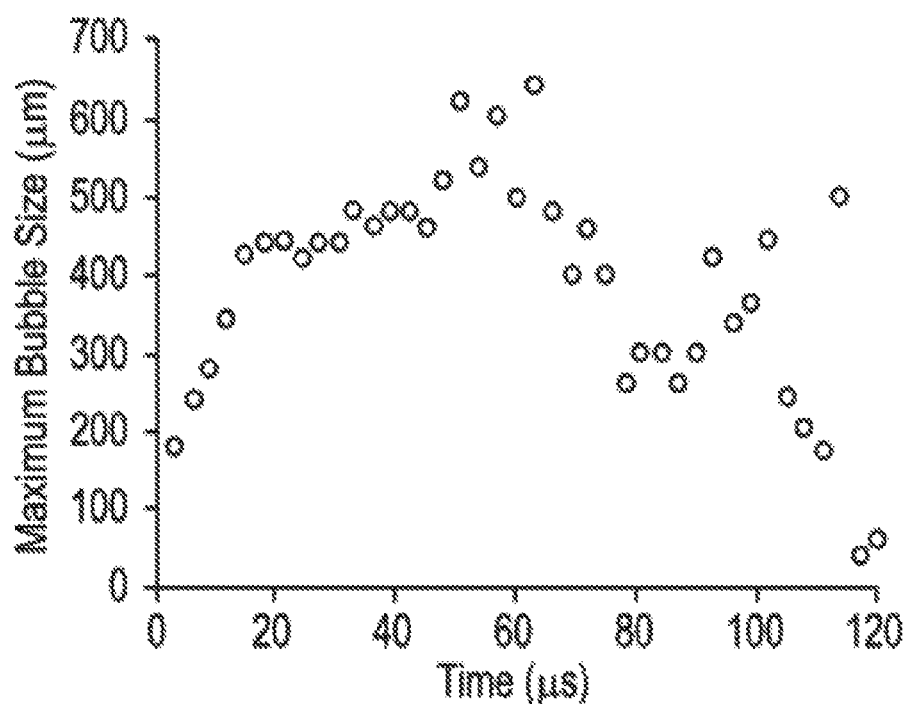

FIG. 8 is a graph of maximum bubble size plotted as a function of time.

Figure 9:
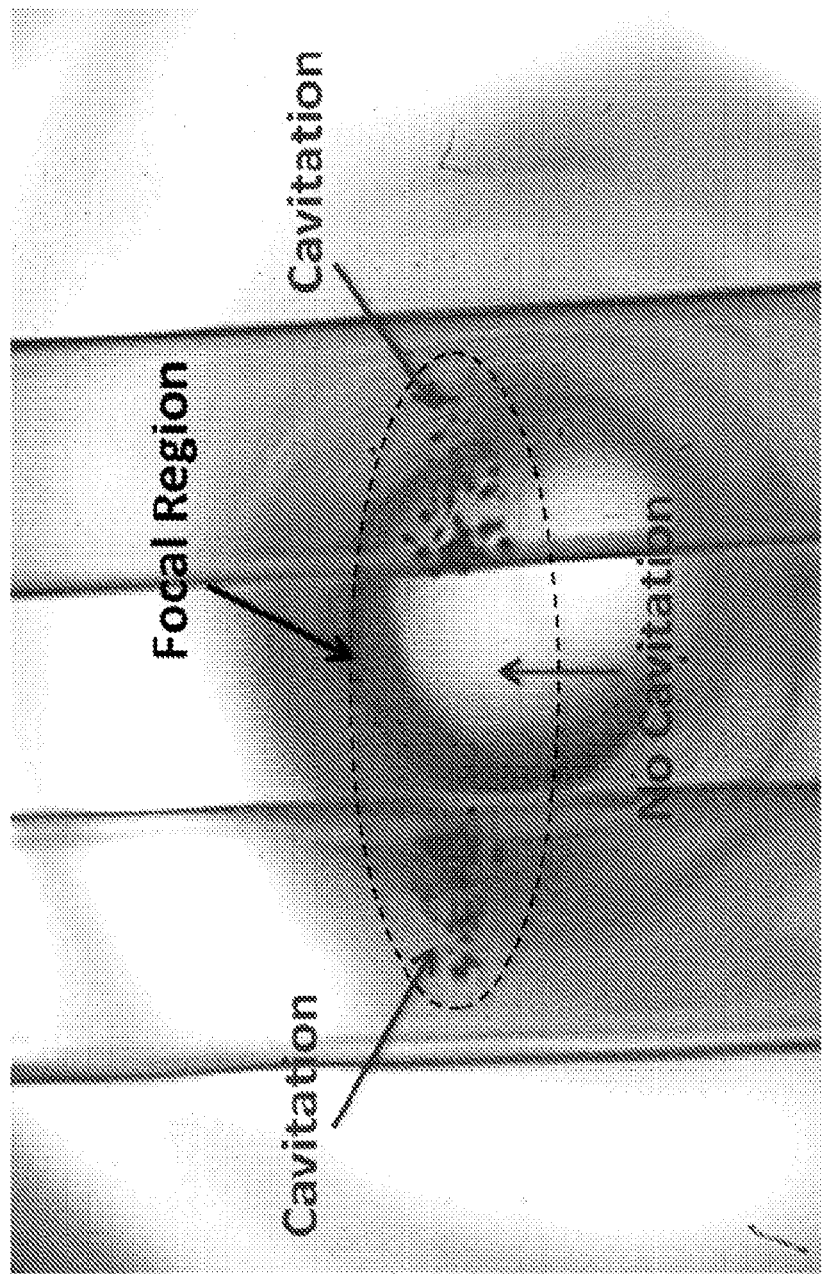
Figure 10:
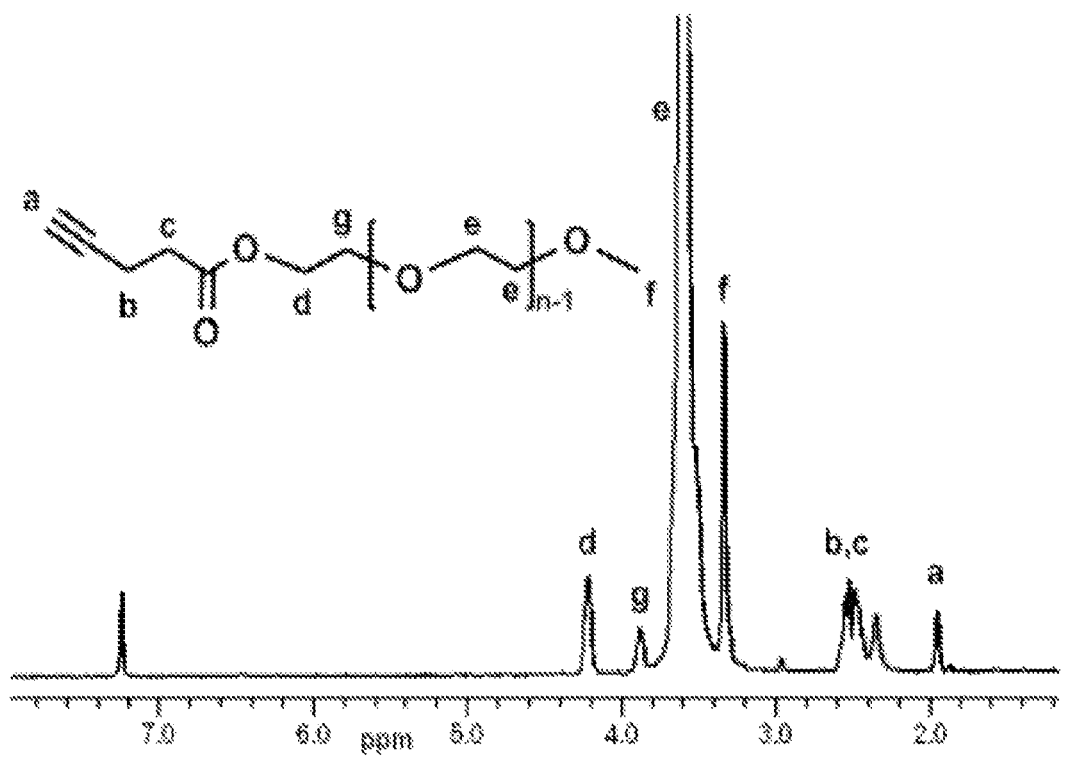

FIG. 9 is an image demonstrating multi-focal ablation of nano-bubbles at 17.3 MPa FIG. 10 is a $^1$H NMR spectrum of alkyne-PEG in $CDCl_3$.

Figure 11:
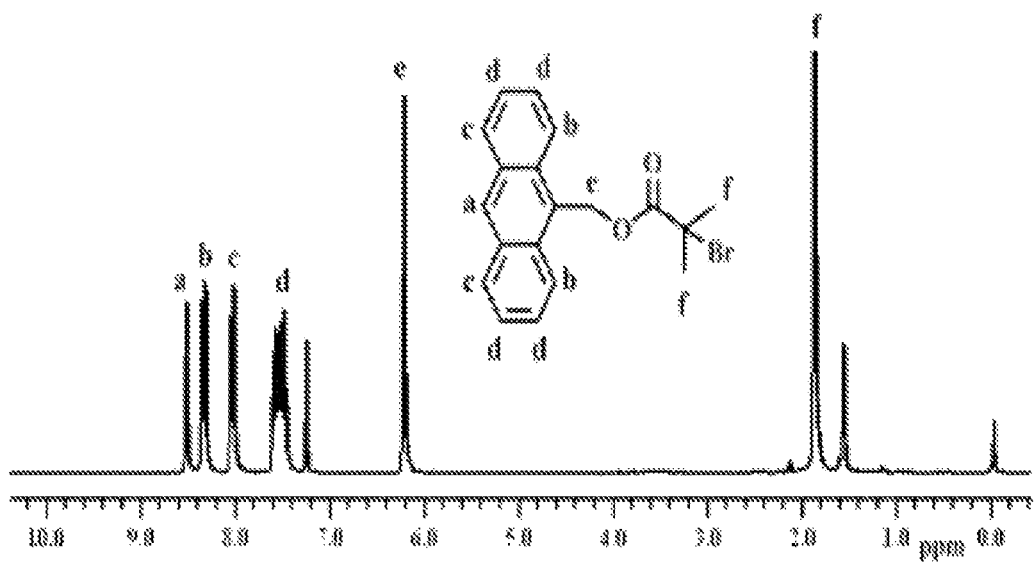

FIG. 11 is a $^1$H NMR spectrum of anthracene functional ATRP initiator in $CDCl_3$.

Figure 12:
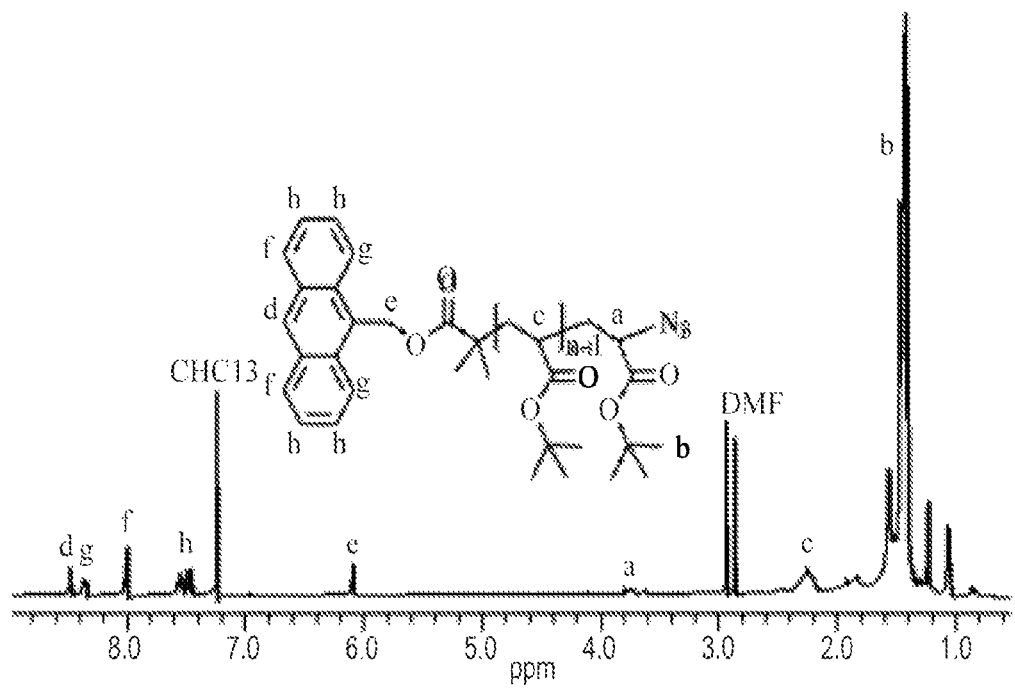

FIG. 12 is a $^1$H NMR spectrum of anthracene-PtBA-azide in $CDCl_3$.

Figure 13:
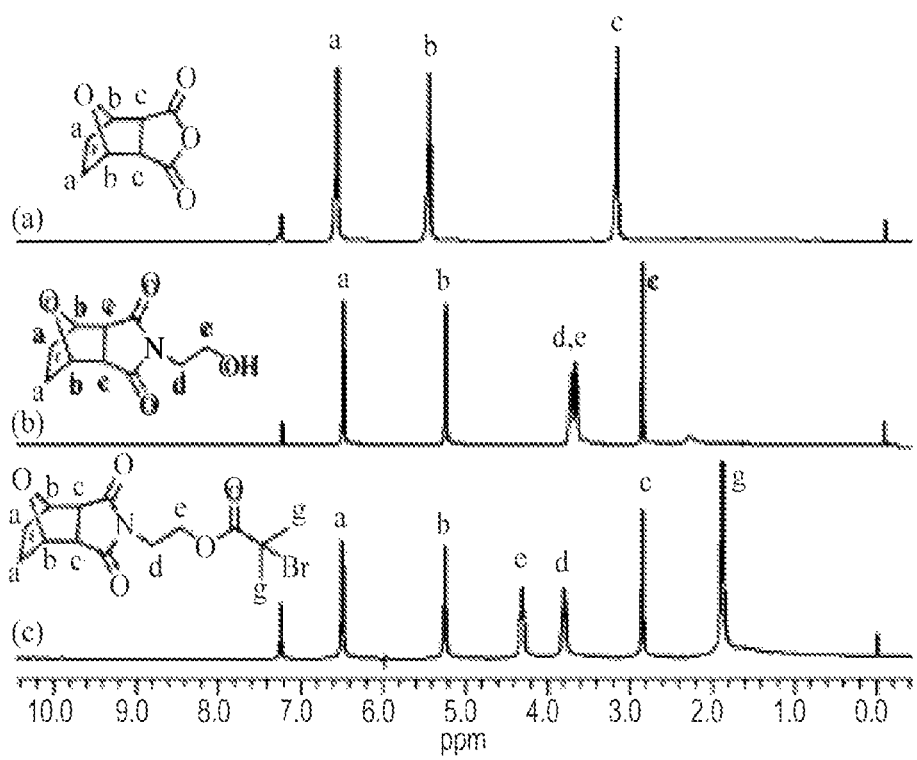

FIG. 13 is a $^1$H NMR spectrum of protected-maleimide functional ATRP initiator in $CDCl_3$.

Figure 14:
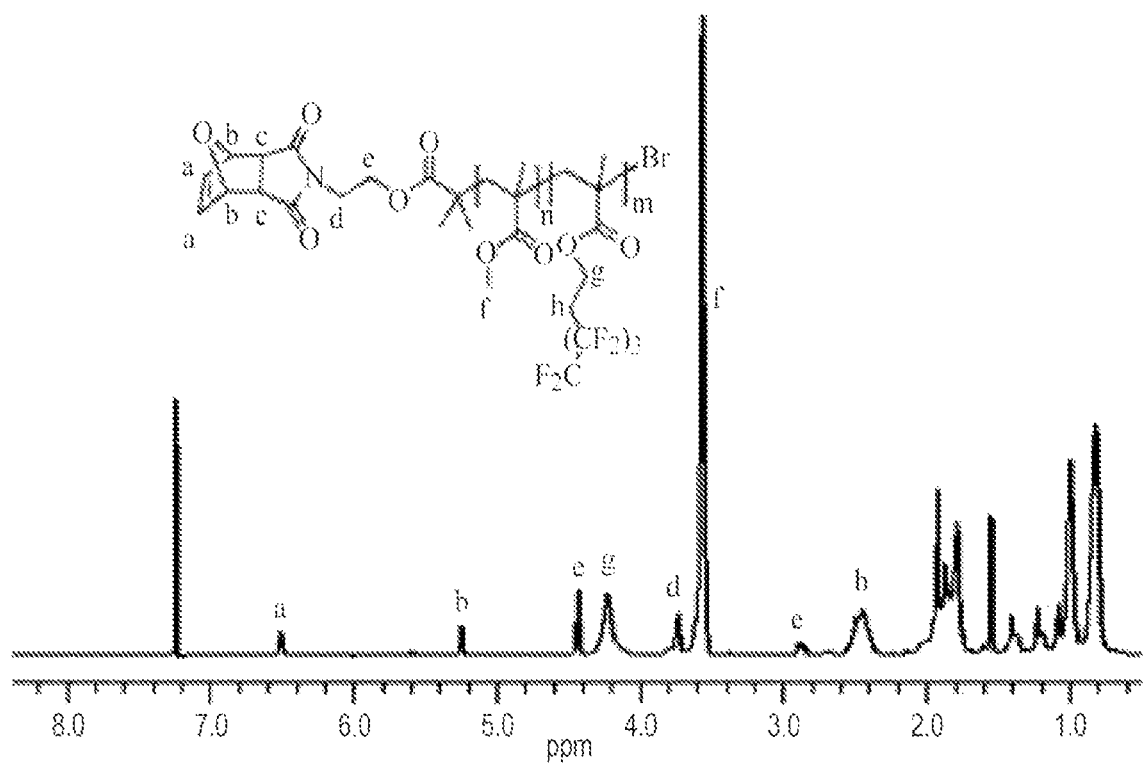

FIG. 14 is a $^1$H NMR spectrum of protected-maleimide-P (HDFMA-co-MMA) in $CDCl_3$.

Figure 15:
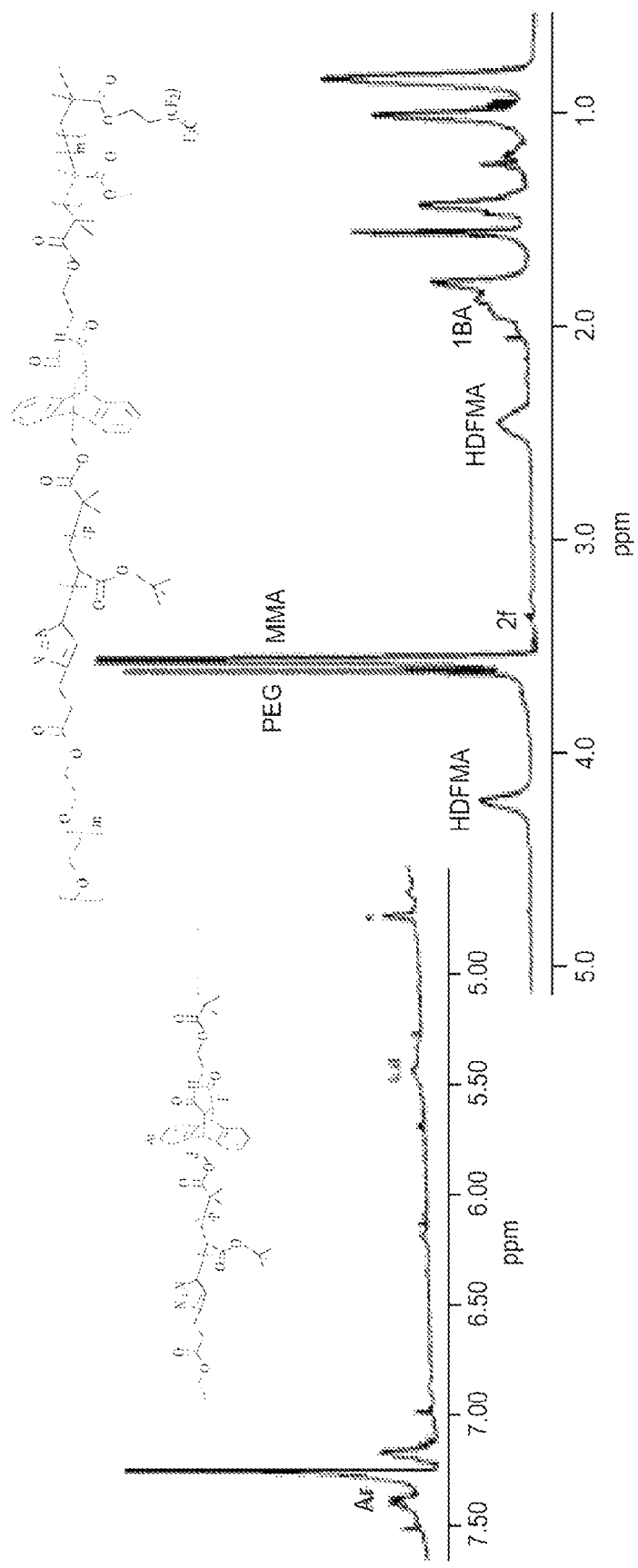

FIG. 15 is a $^1$H NMR spectrum of ABC block copolymer in $CDCl_3$.

Figure 16:
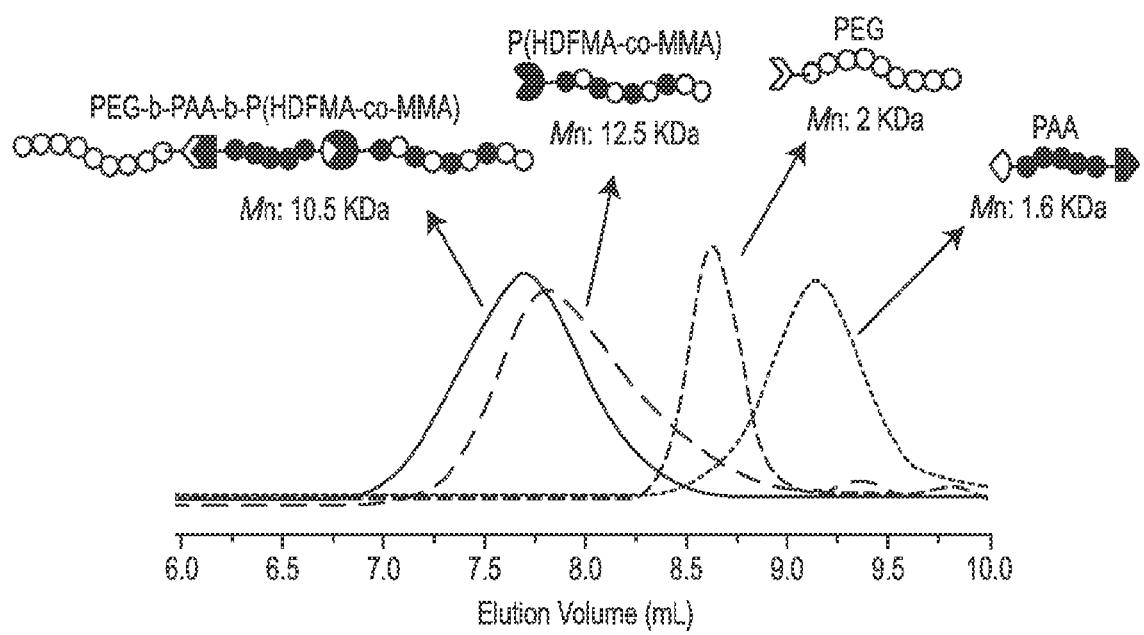

FIG. 16 is a graph of GPC traces of $PEG_{45}$-b-$PAA_{10}$-b-P($MMA_{43}$-co-$HDFMA_{15}$) block copolymer.

Figure 17:
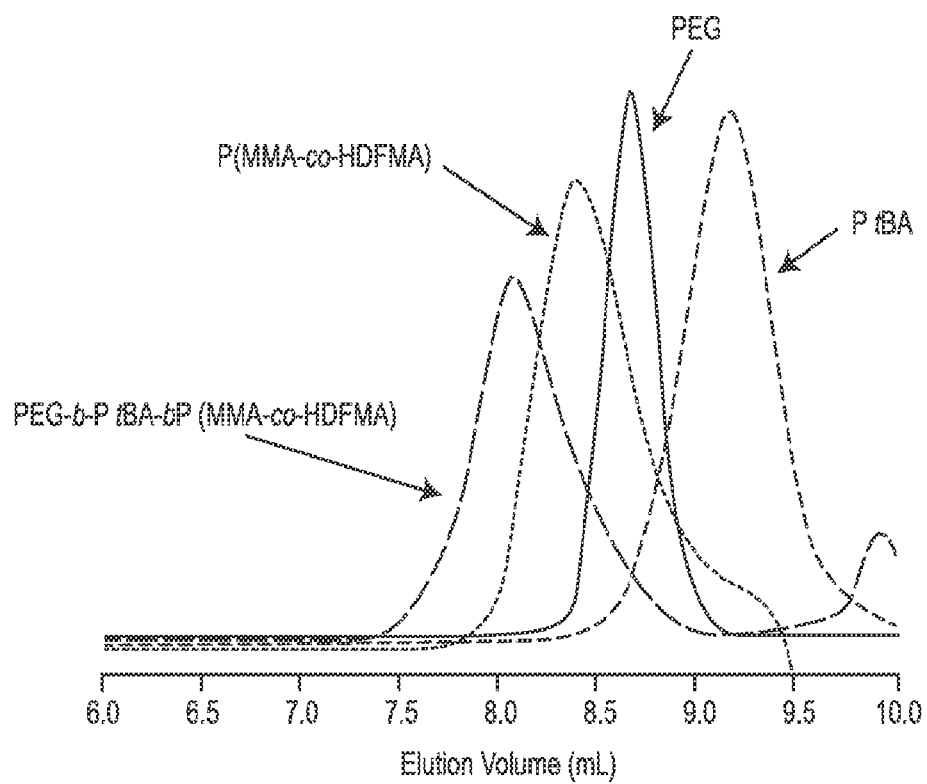

FIG. 17 is a graph of GPC traces of $PEG_{45}$-b-$PAA_{10}$-b-P($MMA_{20}$-co-$HDFMA_8$) block copolymer.

Figure 18:
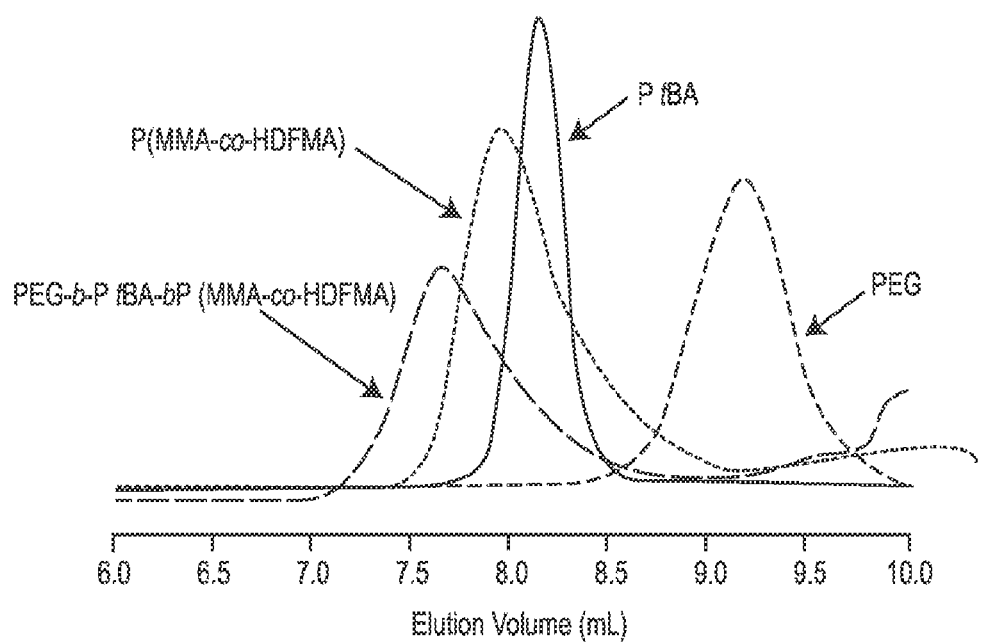

FIG. 18 is a graph of GPC traces of $PEG_{113}$-b-$PAA_{10}$-b-P($MMA_{30}$-co-$HDFMA_{10}$) block copolymer.

Figure 19A:
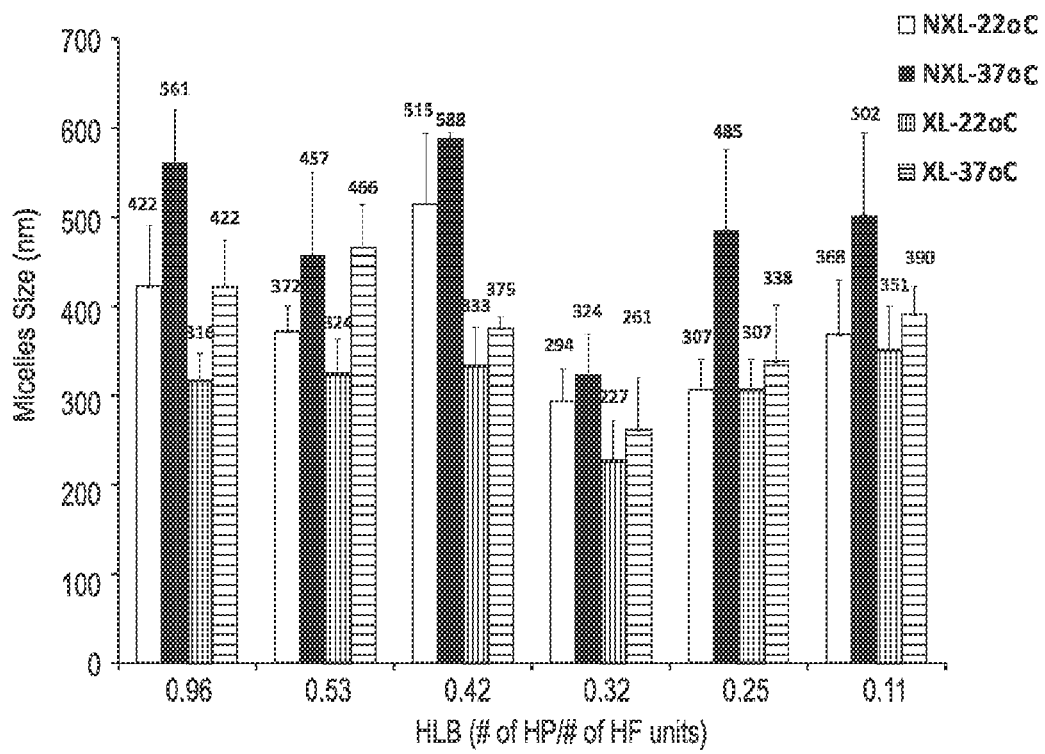
Figure 19B:
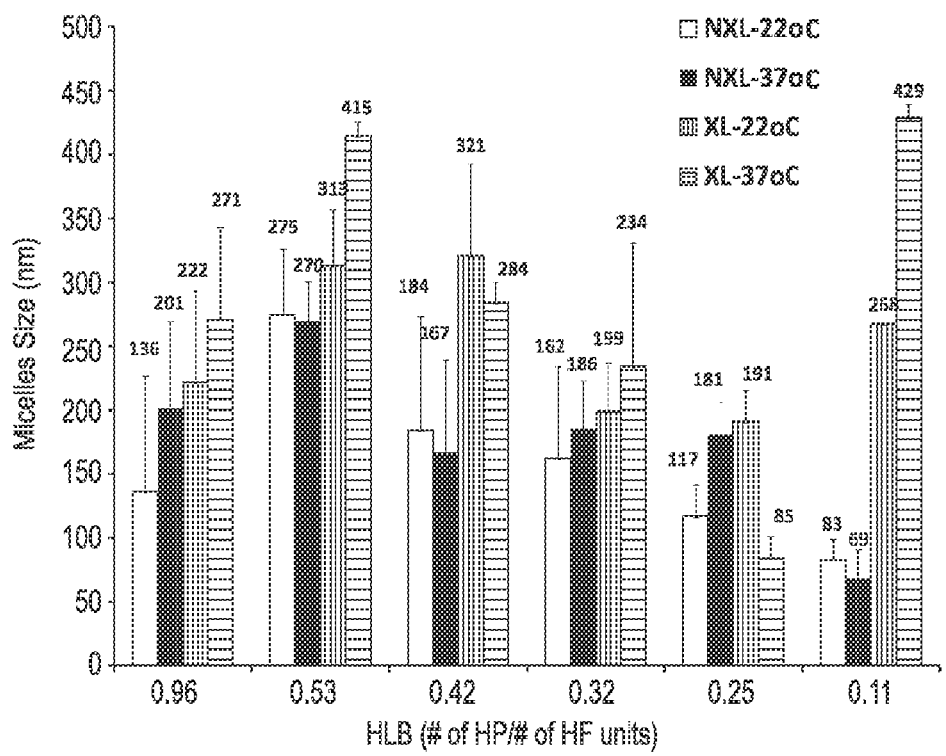

FIGS. 19A and 19B represents a pair of graphs of micelle size plotted by HLB for nonfiltered (A) and filtered (with 0.8 um filter) micelles (B).

Figure 20:
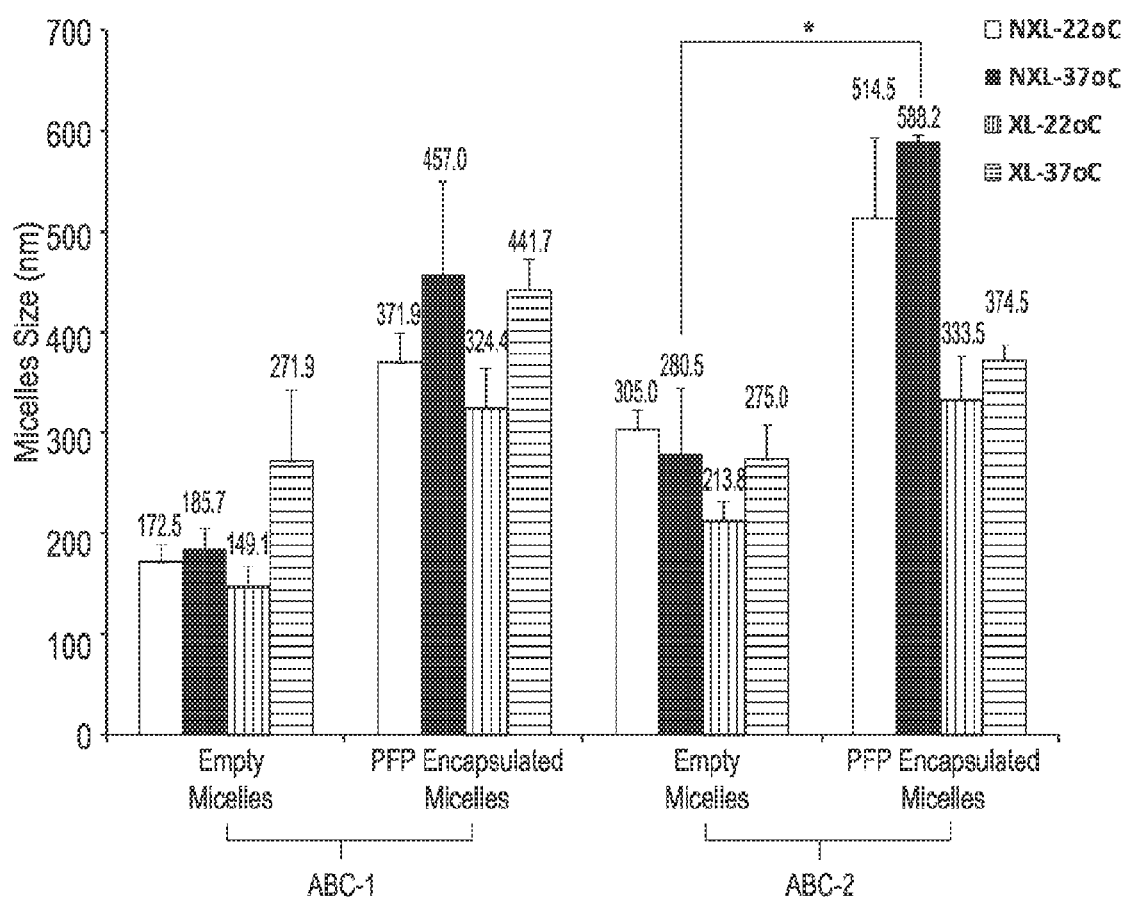

FIG. 20 is a graph of micelle size of empty and PFP encapsulated micelles that are cross-linked (XL) or not cross-linked (NXL).

Figure 21A:
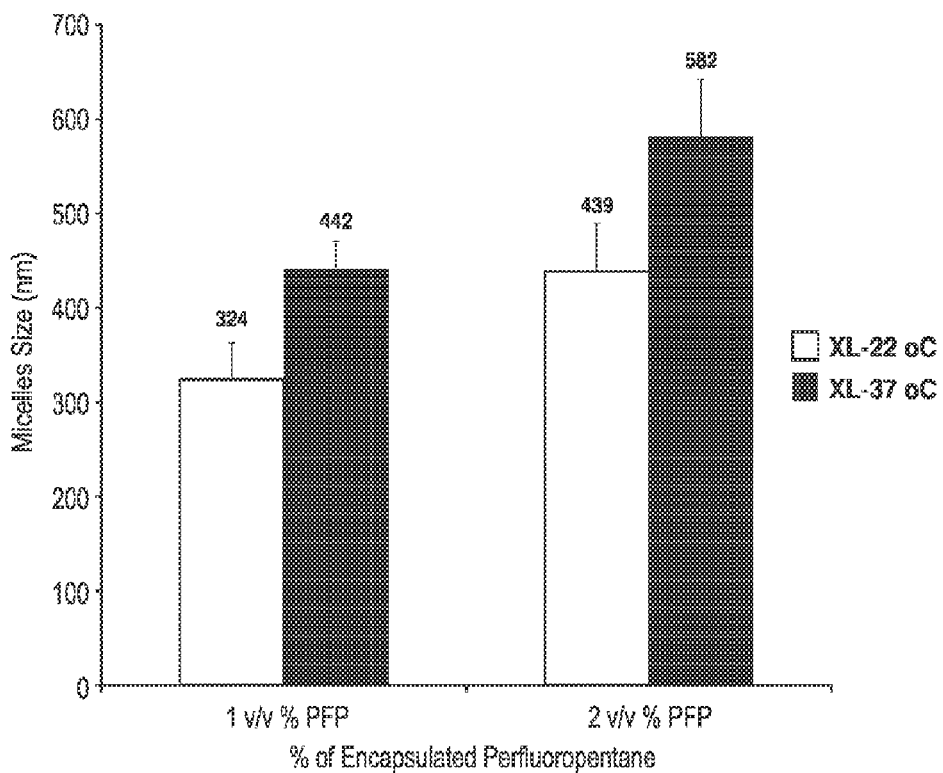
Figure 21B:
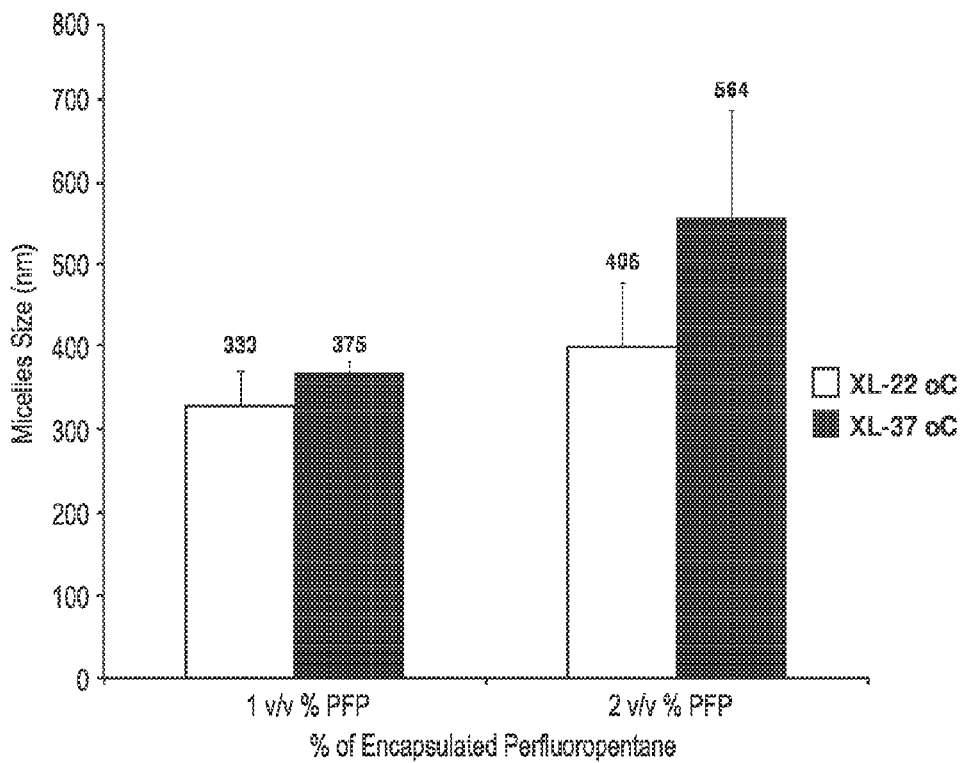
Figure 21C:
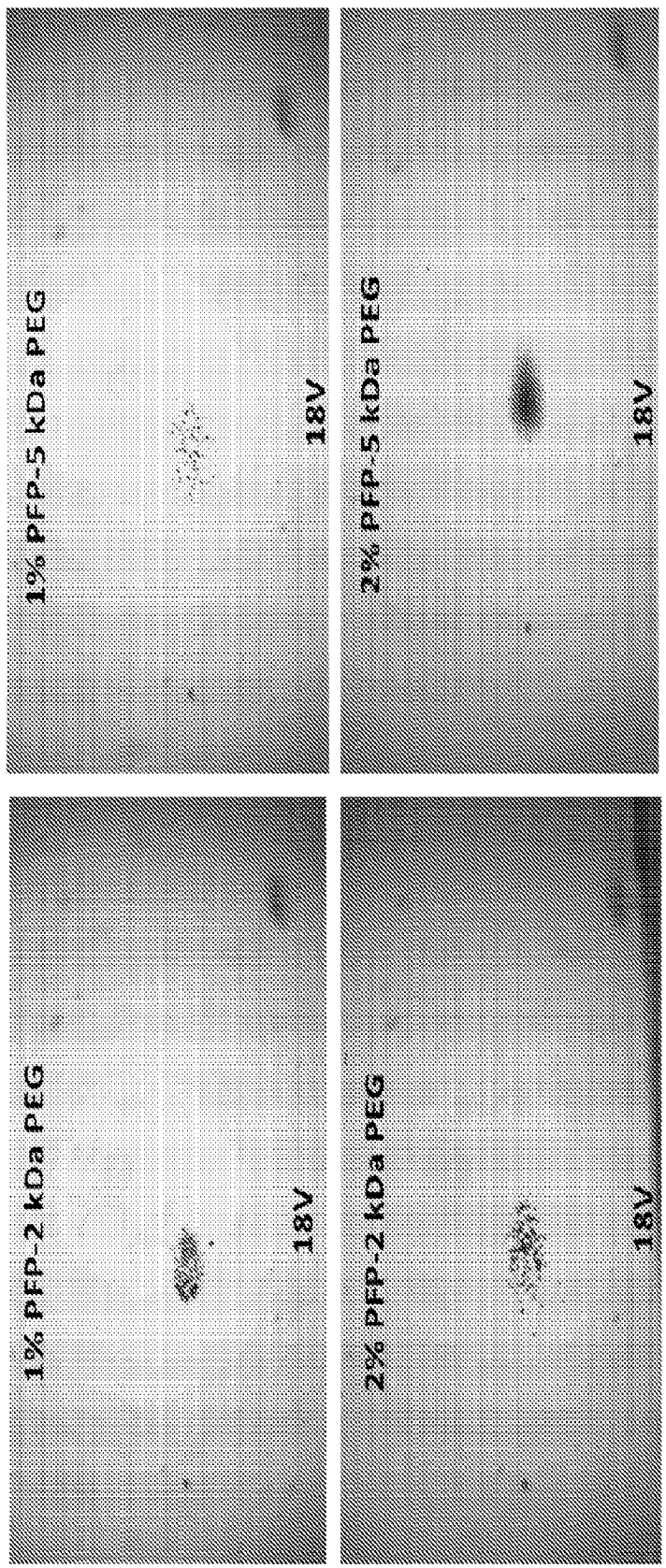

FIGS. 21A to 21C demonstrates the effect of encapsulated % perfluoropentane (PFP) on micelles size ABC-1 (A) and ABC-2 (B). Cavitation results showing nanobubbles generated at low pressure (C).

Figure 22:
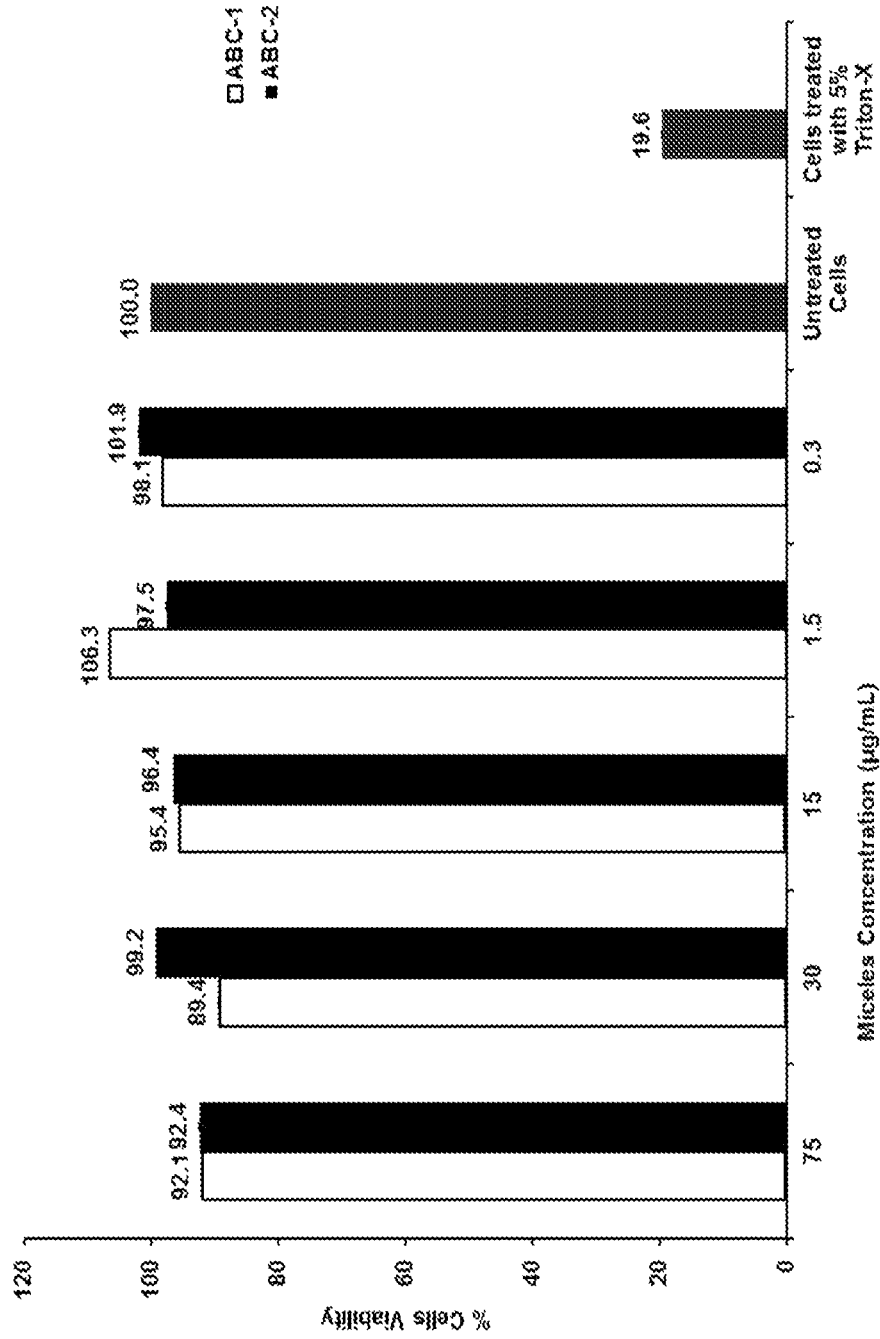

FIG. 22 is a graph of % viability of cells upon exposure to differing micelle concentrations. PC-3 prostate cancer cells were incubated with different concentration of micelles for 24 h.

Figure 23:
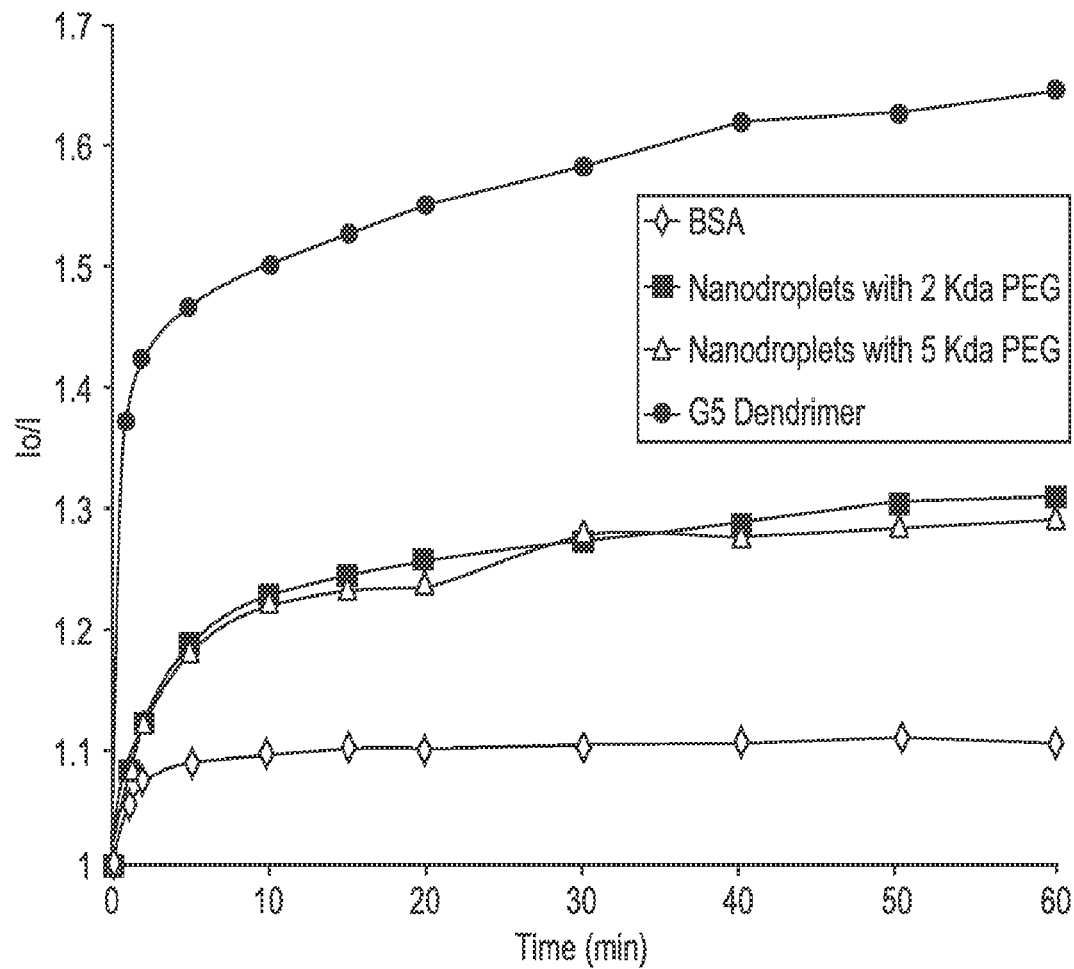

FIG. 23 is a graph of quenched fluorescence for different micelle solutions mixed with BSA.

Figure 24:
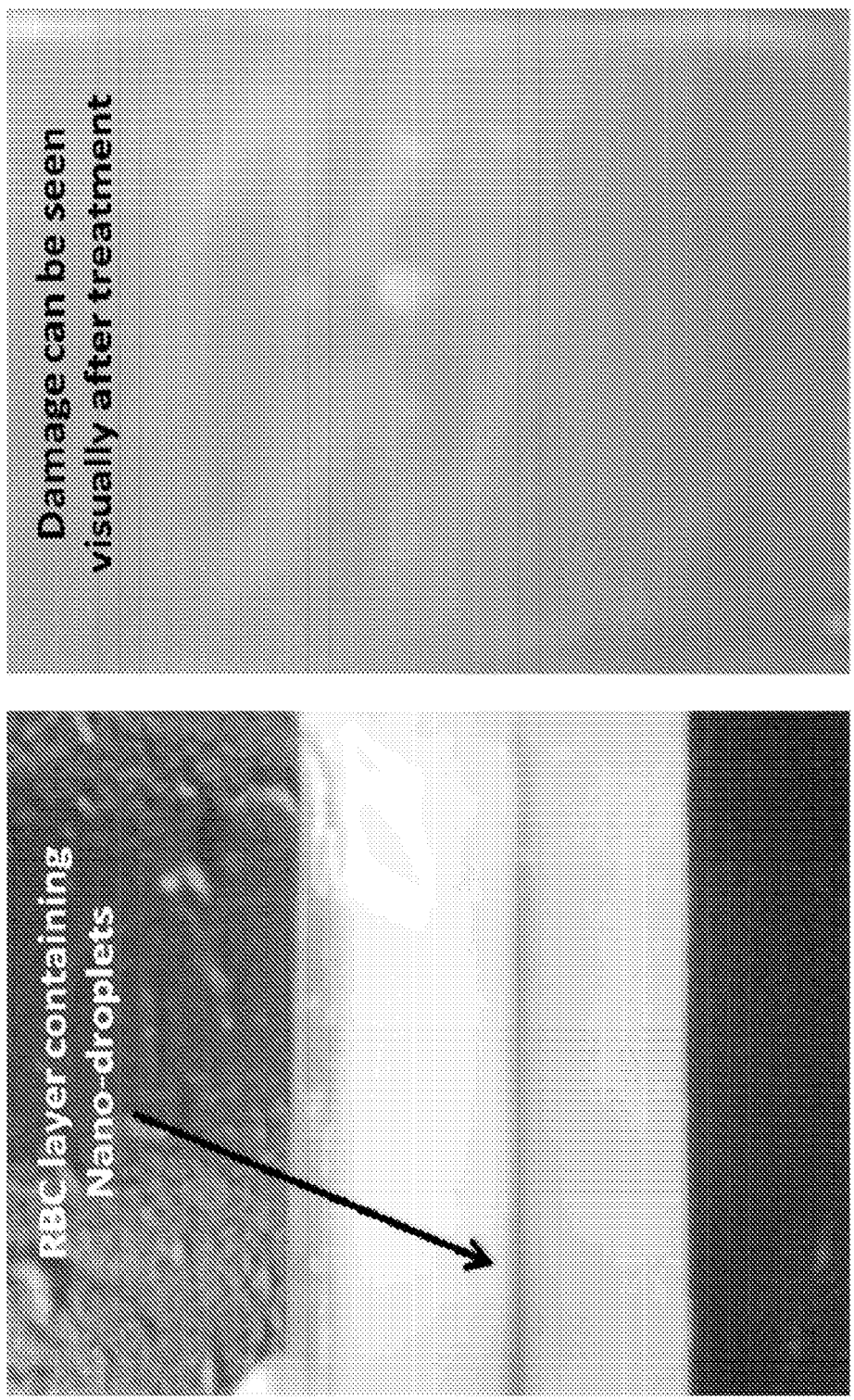

FIG. 24 is an image of an agarose gel with an embedded red blood cell layer, and the damage to the red blood cells after treatment.

Figure 25:
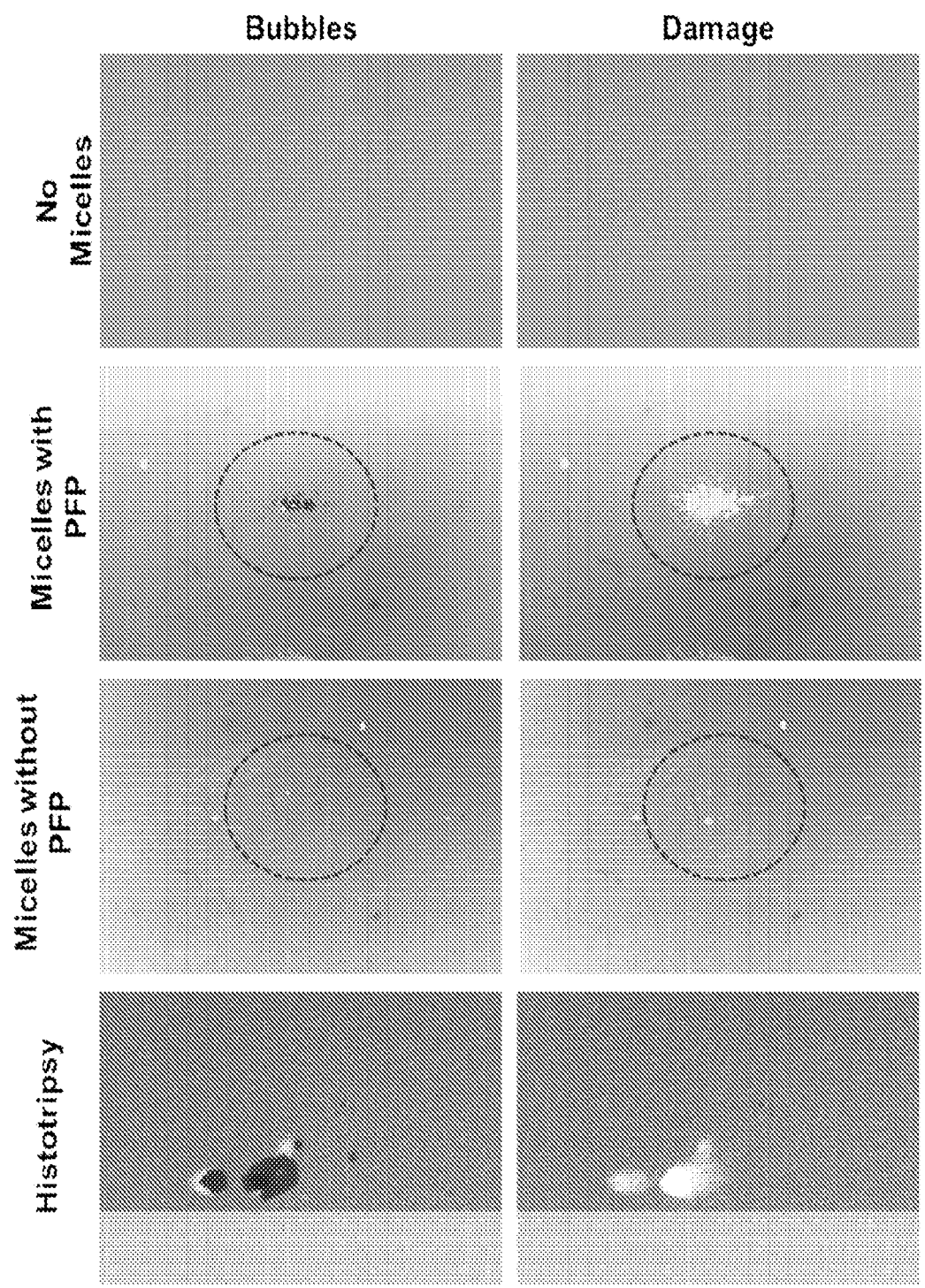

FIG. 25 is a set of images of agarose gel phantoms comparing saline (no micelles), PFP encapsulated micelles (micelles with PFP) empty micelles (micelles without PFP) [10 Hz, 17 mPA (18V), 2000 ultrasound pulses] and regular histotripsy phantom [50 Hz, 22 MPa (30V), 2000 pulses ultrasound].

DETAILED DESCRIPTION

Nanobubbles

Nanometer-sized particles or bubbles (also known as, "nanobubbles") are described in the art. See, for example, Rapoport et al., *Bubble Sci Eng Technol.* 1 (1-2): 31-39 (2009); Gao et al., *Ultrasonics* 48(4): 260-270 (2008; e-publication November 2007); Jiang, *J Applied Polymer Sci* 114: 3472-3478 (2009); Rapoport et al., *J Natl Cancer Inst* 99: 1095-1106 (2007); Krupka et al., *Molec Pharmaceutics* 7(1):

49-59 (2009); U.S. Patent Application Publication No. 2008/0181853 (published on Jul. 31, 2008).

The invention provides nanobubbles useful in methods of diagnosing and treating diseases and medical conditions, including, but not limited to, cancer and tumors. As used herein, the term "nanobubbles" is synonymous with the term "nanodroplets," "nanomicelles," "nano-sized micelles" and "nano-carriers" such that nanodroplets, nanomicelles (or nano-sized micelles), and nanocarriers are also considered a part of the invention.

The invention provides a nanobubble comprising an amphiphilic ABC triblock copolymer, wherein: block A comprises a hydrophilic polymer, block B comprises a crosslinking polymer, and block C comprises a hydrophobic copolymer comprising (i) methyl methacrylate (MMA) and (ii) a fluorinated monomer, wherein the fluorinated monomer is present in the hydrophobic copolymer of block C at 25 mole percent or less.

The invention also provides a nanobubble produced from micellization of an amphiphilic ABC triblock copolymer, wherein: block A comprises a hydrophilic polymer, block B comprises a crosslinking polymer, and block C comprises a hydrophobic copolymer comprising (i) methyl methacrylate (MMA) and (ii) a fluorinated monomer, wherein the fluorinated monomer is present in the hydrophobic copolymer of block C at 25 mole percent or less.

Size

In exemplary embodiments, the nanobubble of the invention has an average diameter of less than or about 700 nm (e.g., less than or about 650 nm, less than or about 600 nm, less than or about 550 nm, less than or about 500 nm, less than or about 450 nm, less than or about 400 nm, less than or about 350 nm, less than or about 300 nm, less than or about 250 nm, less than or about 200 nm, less than or about 150 nm, less than or about 100 nm, less than or about 75 nm, less than or about 50 nm, less than or about 25 nm, less than or about 15 nm, less than or about 10 nm) at about 20° C. or at about 37° C.

In exemplary embodiments, the nanobubble of the invention has average diameter within a range of about 100 nm to about 500 nm (e.g., about 100 nm to about 490 nm, about 100 nm to about 480 nm, about 100 nm to about 470 nm, about 100 nm to about 460 nm, about 100 nm to about 450 nm, about 100 nm to about 440 nm, about 100 nm to about 430 nm, about 100 nm to about 420 nm, about 100 nm to about 410 nm, about 100 nm to about 400 nm, about 100 nm to about 390 nm, about 100 nm to about 380 nm, about 100 nm to about 370 nm, about 100 nm to about 360 nm, about 100 nm to about 350 nm, about 100 nm to about 340 nm, about 100 nm to about 330 nm, about 100 nm to about 320 nm, about 100 nm to about 310 nm, about 100 nm to about 300 nm, about 100 nm to about 290 nm, about 100 nm to about 280 nm, about 100 nm to about 270 nm, about 100 nm to about 260 nm, about 100 nm to about 250 nm, about 100 nm to about 240 nm, about 100 nm to about 230 nm, about 100 nm to about 220 nm, about 100 nm to about 210 nm, about 100 nm to about 200 nm, about 100 nm to about 190 nm, about 100 nm to about 180 nm, about 100 nm to about 170 nm, about 100 nm to about 160 nm, about 100 nm to about 150 nm, about 100 nm to about 140 nm, about 100 nm to about 130 nm, about 100 nm to about 120 nm, about 100 nm to about 110 nm, about 110 nm to about 500 nm, about 120 nm to about 500 nm, about 130 nm to about 500 nm, about 140 nm to about 500 nm, about 150 nm to about 500 nm, about 160 nm to about 500 nm, about 170 nm to about 500 nm, about 180 nm to about 500 nm, about 190 nm to about 500 nm, about 200 nm to about 500 nm, about 210 nm to about 500 nm, about 220 nm to about 500 nm, about 230 nm to about 500 nm, about 240 nm to about 500 nm, about 250 nm to about 500 nm, about 260 nm to about 500 nm, about 270 nm to about 500 nm, about 280 nm to about 500 nm, about 290 nm to about 500 nm, about 300 nm to about 500 nm, about 310 nm to about 500 nm, about 320 nm to about 500 nm, about 330 nm to about 500 nm, about 340 nm to about 500 nm, about 350 nm to about 500 nm, about 360 nm to about 500 nm, about 370 nm to about 500 nm, about 380 nm to about 500 nm, about 390 nm to about 500 nm, about 400 nm to about 500 nm, about 410 nm to about 500 nm, about 420 nm to about 500 nm, about 430 nm to about 500 nm, about 440 nm to about 500 nm, about 450 nm to about 500 nm, about 460 nm to about 500 nm, about 470 nm to about 500 nm, about 480 nm to about 500 nm, about 490 nm to about 500 nm) at about 20° C.

In exemplary aspects, the nanobubble of the invention has an average diameter with a range of about 200 nm and about 700 nm at 22° C. and at 37° C. In exemplary aspects, the nanobubble of the invention has an average diameter with a range of about 200 nm and about 600 nm at 22° C. and at 37° C. In exemplary aspects, the nanobubble of the invention has an average diameter with a range of about 200 nm and about 500 nm at 22° C. and at 37° C. In exemplary aspects, the nanobubble of the invention has an average diameter with a range of about 200 nm and about 400 nm at 22° C. and at 37° C. In exemplary aspects, the nanobubble of the invention has an average diameter with a range of about 200 nm and about 300 nm at 22° C. and at 37° C. In exemplary aspects, the nanobubble of the invention has an average diameter with a range of about 300 nm and about 700 nm at 22° C. and at 37° C., about 400 nm to about 700, about 500 nm to about 700 nm, or about 600 nm to about 700 nm at 22° C. and at 37° C.

In exemplary aspects, the nanobubble of the invention has an average diameter with a range of about 300 nm and about 600 nm, about 300 nm to about 500 nm, about 300 nm to about 400 nm, about 400 nm to about 600 nm, or about 500 nm to about 600 nm n, at 22° C. and at 37° C.

Non-Toxicity, Safety

In exemplary aspects, the nanobubble of the invention is substantially non-toxic to cells, in the absence of ultrasound. Cellular toxicity upon exposure to the nanobubbles of the invention, in the absence of ultrasound, may be assayed through methods known in the art. For example, cellular toxicity may be assayed by testing the integrity of the cell membrane via the use of vital dyes (e.g., trypan blue or propidium iodide), or by monitoring the passage of substances (e.g., lactate dehydrogenase) that are normally sequestered inside cells to the outside. Cellular toxicity also may be assessed by using the 3-(4,5-Dimethyl-2-thiazolyl)-2,5-diphenyl-2H-tetrazolium bromide (MTT) assay, which is described herein. See, Example 3. Additionally, cytotoxicity may be measured by ATP-based assays in which ATP is a marker of viability.

As used herein, the term "substantially non-toxic" in the context of the nanobubbles of the invention means that the nanobubbles are toxic to 10% or less of a population of cells, when incubated with the population of cells, in the absence of ultrasound. In exemplary aspects, the nanobubbles of the invention are toxic to about 10% or less of a population of cells, when incubated with the population of cells, in the absence of ultrasound (e.g., <500 kHz ultrasound), as measured by, e.g., an MTT assay. In exemplary aspects, not more than 10% of a population of cells are killed upon incubation of the nanobubbles of the invention without ultrasound with the cells. In exemplary aspects, the nanobubbles of the invention are toxic to less than or about 9% (e.g., less than or about 8%, less than or about 7%, less than or about 6%, less than or about 5%, less than or about 4%, less than or about 3%, less than or about 2%, or less than or about 1%) of a population of cells, when the nanobubbles are incubated with the population of cells, in the absence of ultrasound, as measured by, e.g., an MTT assay.

Ultrasound-Mediated Cell Ablation and Histotripsy

In the presence of ultrasound (e.g., <500 kHz), the nanobubbles cavitate. Cavitation is the formation and then immediate implosion of cavities in liquid that are consequential to the forces acting upon the liquid. In exemplary aspects, cavitation occurs when a liquid is subjected to rapid changes of pressure that cause the formation of cavities when the pressure is relatively low. When the nanobubbles are near, on, or within a cell, and the nanobubbles cavitate, the effect on the cell is ablation of the cell.

In exemplary aspects, the nanobubbles of the invention are used in combination with histotripsy to achieve cell ablation of unwanted cells. Histotripsy is a technique to achieve mechanical fractionation of tissue structure using a number of short (several μsec), high intensity ultrasound pulses. The ultrasound intensity used is hundreds of times higher than regular diagnostic imaging and similar to "lithotripsy" which has been used for breaking down kidney stones. See, e.g., Hempel et al., *J Urol* 184(4): 1484-1489 (2011). Histotripsy uses microsecond-long, high pressure, shockwave pulses to create a cluster of dense micro-bubbles (i.e. a bubble cloud) using pre-existing gas pockets in the body.[53-55] These microbubbles have been shown to expand reaching an average diameter of 10-100 μm, contract, and energetically collapse in a process termed cavitation, which mechanically fractionate the treated tissue into a liquid-like acellular homogenate with astonishingly high precision.[56-58] However, the acoustic pressure required to initiate a cavitation bubble cloud from the very small gas nuclei (<10 nm) pre-existing in the body using a micro-second long pulse is very high (~30 MPa).[59] This high pressure is primarily to overcome the initially large Laplace pressure caused by the surface tension at the interface between the liquid shell and the gas core of the small nuclei.[59] The nanobubbles of the invention comprise contrast agents which expand to reach an average diameter of 10-100 μm necessary to produce cellular disruption at a significantly reduced acoustic pressure with low frequency ultrasound (e.g., <500 kHz). This reduced cavitation threshold by the nano-bubbles allows for precise and efficient ablation of multi-foci prostate cancer cells. When applying an acoustic pressure that is above the threshold of cavitation of the nanobubbles but below the cavitation threshold without the contrast agent, only cancer cells bound to the targeted nanobubbles will be ablated while the surrounding cells will remain undamaged. The nanobubbles of the invention allow for selective and simultaneous ablation of multiple foci of prostate cancer cells in a large tissue volume in a short period of time by using a therapeutic US transducer with a large focal zone. Treatment of a large focal zone can also be achieved by using a lower US frequency (<500 kHz). Moreover, the lower frequency facilitates the penetration through bones and a long tissue path by reducing the attenuation and aberration effects, which makes this technique well suited for the non-invasive ablation of prostate cancer cells. Furthermore, the combination of targeted nano-bubbles with application of a large focal zone therapeutic US will allow selective ablation of prostate cancer foci that may not be detected with clinical imaging because of their small size due to the significantly reduced cavitation threshold in these cancer lesions (where the nanobubbles are bound) compared to normal tissue.

In exemplary aspects, the nanobubbles undergo cavitation in the presence of or when exposed to ultrasound pulses with a peak negative pressure which is less than what is normally used in histotripsy (e.g., 30 MPa, 25 MPa). Thus, the threshold for nanobubble cavitation and cell ablation is lower, relative to those ultrasound pulses applied in standard histotripsy (pulse repetition frequency of 50 Hz, peak negative pressure of 25 MPa). In exemplary aspects, the nanobubbles undergo cavitation in the presence of or when exposed to ultrasound pulses with a peak negative pressure of less than about 25 MPa and greater than about 7 MPa or less than about 22 MPa and greater than about 7 MPa. In exemplary aspects, the nanobubbles undergo cavitation in the presence of or when exposed to ultrasound pulses with a peak negative pressure within a range of about 10 MPa and 25 MPa (e.g., within a range of about 10 MPa to about 22.5 MPa, within a range of about 10 MPa to about 20 MPa, within a range of about 10 MPa to about 17.5 MPa, within a range of about 10 MPa to about 15 MPa, within a range of about 10 MPa to about 12.5 MPa, within a range of about 12.5 MPa to about 25 MPa, within a range of about 15 MPa to about 25 MPa, within a range of about 17.5 MPa to about 25 MPa, within a range of about 17.5 MPa to about 25 MPa, within a range of about 20 MPa to about 25 MPa, within a range of about 22.5 MPa to about 25 MPa, within a range of about 12.5 MPa to about 22.5 MPa, or within a range of about 15 MPa to about 20 MPa).

Composition

In exemplary embodiments, the nanobubbles of the invention comprise an amphiphilic ABC triblock copolymer. In exemplary embodiments, the nanobubbles of the invention are produced by micellization of an amphiphilic ABC triblock copolymer. Amphiphilic ABC triblock copolymers suitable for comprising or for producing the nanobubbles of the invention are described herein.

Amphiphilic ABC Triblock Copolymer

Block A comprises a hydrophilic polymer. As used herein, "hydrophilic" means "water loving" and refers to a polymer that mix well with water. The hydrophilic polymer has an affinity for water and readily absorbs or dissolves in water. Hydrophilic polymers are known in the art. In exemplary aspects, the hydrophilic polymer of block A comprises an amphiphilic group selected from the group consisting of: ethylene oxide, carboxylic acid, hydroxyl, and a quaternized amine group. In exemplary aspects, the hydrophilic polymer of block A is selected from the group consisting of: polyethylene glycol (PEG), poly(trimethyl ethyl methacrylate), poly (acrylic acid), and poly(N-2-hydroxy propyl)methacrylamide (PHPMA). In exemplary aspects, the hydrophilic polymer of block A is polyethylene glycol (PEG). The hydrophilic polymer (e.g., the PEG), in exemplary aspects, has a number average molecular weight of about 1 kDa to about 6 kDa or about 1 kDa to about 5 kDa (e.g., 1.0 kDa, 1.5 kDa, 2.0 kDa, 2.5 kDa, 3.0 kDa, 3.5 kDa, 4.0 kDa, 4.5 kDa, 5.0 kDa). In exemplary aspects, the PEG has a number average molecular weight of about 1 kDa to about 4 kDa, about 1 kDa to about 3 kDa, about 1 kDa to about 2 kDa, about 2 kDa to about 5 kDa, about 3 kDa to about 5 kDa, or about 4 kDa to about 5 kDa.

Block B comprises a crosslinking polymer. Many crosslinking polymers are known in the art and include any polymer comprising one or more functional groups that may be crosslinked to one another. In exemplary aspects, the crosslinking polymer comprises one or more amine reactive functional groups. In exemplary aspects, the crosslinking polymer comprises a functional group that allows for rapid reaction with a crosslinker. In exemplary embodiments, the crosslinking polymer of Block B is polyacrylic acid (PAA) or poly(hydroxyl ethyl acrylate) (PHEA) or poly(pentafluorophenyl acrylate) (PP FPA). In exemplary aspects, the crosslinking polymer has a number average molecular weight of about 1 kDa to about 5 kDa (e.g., 1.0 kDa, 1.5 kDa, 2.0 kDa, 2.5 kDa, 3.0 kDa, 3.5 kDa, 4.0 kDa, 4.5 kDa, 5.0 kDa) or about 0.5 kDa to about 3 kDa. In exemplary aspects, the crosslinking polymer has a number average molecular weight of about 1 kDa to about 4 kDa, about 1 kDa to about 3 kDa, about 1 kDa to about 2 kDa, about 1.3 kDa to about 1.8 kDa, about 2 kDa to about 5 kDa, about 3 kDa to about 5 kDa, or about 4 kDa to about 5 kDa. In exemplary embodiments, the crosslinking polymer has a number average molecular weight of about 1.0, 1.1, 1.2, 1.3, 1.4, 1.5, 1.6, 1.7, 1.8, 1.9, or 2.0. In exemplary aspects, the crosslinking polymer has a number average molecular weight of about 0.5 kDa to about 2.5 kDa, about 0.5 kDa to about 2.0 kDa, about 0.5 kDa to about 1.5 kDa, about 0.5 kDa to about 1.0 kDa, about 1.0 kDa to about 3.0 kDa, about 1.5 kDa to about 3.0 kDa, about 2.0 kDa to about 3.0 kDa, or about 2.5 kDa to about 3.0 kDa.

Block C comprises a hydrophobic copolymer comprising (i) methyl methacrylate (MMA) and a fluorinated monomer, wherein the fluorinated monomer is present in the hydrophobic copolymer of block C at about 25 mole percent or less. In exemplary aspects, the fluorinated monomer is present in the hydrophobic copolymer of block C at about 24 mole percent or less, about 23 mole percent or less, about 22 mole percent or less, about 21 mole percent or less, about 20 mole percent or less, about 19 mole percent or less, about 18 mole percent or less, about 17 mole percent or less, about 16 mole percent or less, about 15 mole percent or less, about 14 mole percent or less, about 13 mole percent or less, about 12 mole percent or less, about 11 mole percent or less, about 10 mole percent or less, about 9 mole percent or less, about 8 mole percent or less, about 7 mole percent or less, about 6 mole percent or less, about 5 mole percent or less, about 4 mole percent or less, about 3 mole percent or less, about 2 mole percent or less, or about 1 mole percent or less.

In exemplary aspects, the fluorinated monomer is present in the hydrophobic copolymer of block C at an amount between about 1 mole percent and about 25 mol percent, about 2 mole percent and about 25 mol percent, about 3 mole percent and about 25 mol percent, about 4 mole percent and about 25 mol percent, about 5 mole percent and about 25 mol percent, about 6 mole percent and about 25 mol percent, about 7 mole percent and about 25 mol percent, about 8 mole percent and about 25 mol percent, about 9 mole percent and about 25 mol percent, about 10 mole percent and about 25 mol percent, about 11 mole percent and about 25 mol percent, about 12 mole percent and about 25 mol percent, about 13 mole percent and about 25 mol percent, about 14 mole percent and about 25 mol percent, about 15 mole percent and about 25 mol percent, about 16 mole percent and about 25 mol percent, about 17 mole percent and about 25 mol percent, about 18 mole percent and about 25 mol percent, about 19 mole percent and about 25 mol percent, about 20 mole percent and about 25 mol percent, about 21 mole percent and about 25 mol percent, about 22 mole percent and about 25 mol percent, about 23 mole percent and about 25 mol percent, or about 24 mole percent and about 25 mol percent.

In exemplary aspects, the number of fluorine atoms per unit of hydrophobic copolymer is between about 60 and about 255. In exemplary aspects, the number of fluorine atoms per unit of hydrophobic copolymer is between about 68 to about 250, about 75 to about 225, about 100 to about 200, about 125 to about 175, about 60 to about 225, about 60 to about 200, about 60 to about 175, about 60 to about 150, about 60 to about 125, about 60 to about 100, about 75 to about 255, about 100 to about 255, about 125 to about 255, about 150 to about 255, about 175 to about 255, about 200 to about 255, or about 225 to about 255.

In exemplary aspects, the fluorinated monomer comprises a fluorinated alkyl chain. In exemplary aspects, the fluorinated alkyl chain comprises a chain of n carbon atoms, wherein n is 8 to 20 (e.g., 8, 9, 10, 11, 12, 13, 14, 15, 16, 17, 18, 19, 20), and wherein up to m carbon atoms are completely fluorinated, wherein m=n−2.

In exemplary aspects, the fluorinated monomer is a fluorinated lipid chain. In certain aspects, the fluorinated lipid chain comprises fluorinated oleic acid or 3,3,4,4,5,5,6,6,7,7, 8,8,9,9,10,10,10-heptadecafluorodecan-1-ol.

In exemplary aspects, the fluorinated monomer is hexadecafluorodecylmethacrylate (HDFMA), 3,3,4,4,5,5,6,6,7,7,8, 8,9,9,10,10,10-Heptadecafluorodecyl methacrylate, 1H,1H, 2H,2H-perfluorooctyl methacrylate, or 2,2,2-Trifluoroethyl methacrylate. In some aspects, block C comprises a hydrophobic random copolymer comprising MMA and HDFMA. In exemplary aspects, the hydrophobic copolymer of Block C is a random copolymer of comprising (i) methyl methacrylate (MMA) and a fluorinated monomer. In exemplary aspects, the mole ratio of the monomers of MMA to the monomers of HDFMA is between about 80 and 95, as described herein.

In some aspects, the hydrophobic copolymer of Block C comprises a polymer other than MMA, e.g., an acrylic polymer other than MMA. In exemplary aspects, the acrylic polymer comprises a structure of Formula I:

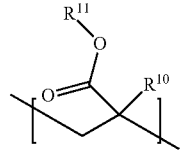

[Formula I]

In some embodiments, $R^{10}$ is hydrogen, methyl, ethyl, or propyl and $R^{11}$ is $C_1$-$C_{50}$ alkyl. Suitable monomers of Formula I for use in the present invention according to these embodiments include, for example, methyl acrylate, ethyl acrylate, propyl acrylate, isopropyl acrylate, n-butyl acrylate, isobutyl acrylate, tert-butyl acrylate, hexyl acrylate, isooctyl acrylate, isodecyl acrylate, octadecyl acrylate, lauryl acrylate, 2-ethylhexyl acrylate, 4-tert-butylcyclohexyl acrylate, 3,5,5-trimethylhexyl acrylate, isobornyl acrylate, ethyl methacrylate, butyl methacrylate, isobutyl methacrylate, tert-butyl methacrylate, hexyl methacrylate, 2-ethylhexyl methacrylate, isodecyl methacrylate, lauryl methacrylate, stearyl methacrylate, cyclohexyl methacrylate, 3,3,5-trimethylcyclohexyl methacrylate, ethyl 2-ethylacrylate, ethyl 2-propylacrylate, and isobornyl methacrylate. In exemplary aspects, the acrylic polymer is ethyl methacrylate, butyl methacrylate, isobutyl methacrylate, tert-butyl methacrylate, or hexyl methacrylate.

In exemplary aspects, the fluorinated monomer of the hydrophobic copolymer of Block C comprises a structure of Formula II:

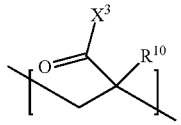

[Formula II]

In some embodiments, suitable monomers for use in the present invention include fluorinated acrylic monomers. Suitable monomers of Formula VII for use in the present invention according to these embodiments include, for example, 2,2,3,3,4,4,5,5,6,6,7,7-dodecafluoroheptyl acrylate, 4,4,5,5, 6,6,7,7,8,9,9,9-dodecafluoro-2-hydroxy-8-(trifluoromethyl) nonyl methacrylate, 3,3,4,4,5,5,6,6,7,7,8,8,9,9,10,10,11,12, 12,12-eicosafluoro-11-(trifluoromethyl)dodecyl methacrylate, 3,3,4,4,5,5,6,6,7,7,8,8,9,9,10,10,11,11,12,12, 12-heneicosafluorododecyl acrylate, 3,3,4,4,5,5,6,6,7,7,8,8, 9,9,10,10,11,11,12,12,12-heneicosafluorododecyl methacrylate, 3,3,4,4,5,5,6,6,7,7,8,8,9,9,10,10,10-heptadecafluorodecyl methacrylate, 2,2,3,3,4,4,4-heptafluorobutyl acrylate, 2,2,3,3,4,4,4-heptafluorobutyl methacrylate, 2,2,3,4,4,4-hexafluorobutyl acrylate, 2,2,3,4,4, 4-hexafluorobutyl methacrylate, 1,1,1,3,3,3-hexafluoroisopropyl acrylate, 1,1,1,3,3,3-hexafluoroisopropyl methacrylate, 2,2,3,3,4,4,5,5-octafluoropentyl acrylate, 2,2,3,3,4,4,5, 5-octafluoropentyl methacrylate, 2,2,3,3,3-pentafluoropropyl acrylate, 2,2,3,3,3-pentafluoropropyl methacrylate, 1H,1H,2H,2H-perfluorodecyl acrylate, 2,2,3, 3-tetrafluoropropyl methacrylate, 3,3,4,4,5,5,6,6,7,7,8,8,8-tridecafluorooctyl acrylate, 3,3,4,4,5,5,6,6,7,7,8,8,8-tridecafluorooctyl methacrylate, 2,2,2-trifluoroethyl methacrylate, 1,1,1-trifluoro-2-(trifluoromethyl)-2-hydroxy-4-methyl-5-pentyl methacrylate, and 2-[(1',1',1'-trifluoro-2'-(trifluoromethyl)-2'-hydroxy)propyl]-3-norbornyl methacrylate. In exemplary aspects, the fluorinated monomer is 4,4,5, 5,6,6,7,7,8,9,9,9-dodecafluoro-2-hydroxy-8-(trifluoromethyl)nonyl methacrylate, 3,3,4,4,5,5,6,6,7,7,8,8, 9,9,10,10,11,12,12,12-eicosafluoro-11-(trifluoromethyl) dodecyl methacrylate, 3,3,4,4,5,5,6,6,7,7,8,8,9,9,10,10,11, 11,12,12,12-heneicosafluorododecyl methacrylate, 3,3,4,4, 5,5,6,6,7,7,8,8,9,9,10,10,10-heptadecafluorodecyl methacrylate, 2,2,3,3,4,4,4-heptafluorobutyl methacrylate, 2,2,3,4,4,4-hexafluorobutyl methacrylate, 1,1,1,3,3,3-hexafluoroisopropyl methacrylate, 2,2,3,3,4,4,5,5-octafluoropentyl methacrylate, 2,2,3,3,3-pentafluoropropyl methacrylate, 2,2,3,3-tetrafluoropropyl methacrylate, 3,3,4,4,5,5, 6,6,7,7,8,8,8-tridecafluorooctyl methacrylate, 2,2,2-trifluoroethyl methacrylate, 1,1,1-trifluoro-2-(trifluoromethyl)-2-hydroxy-4-methyl-5-pentyl methacrylate, or 2-[(1',1',1'-trifluoro-2'-(trifluoromethyl)-2'-hydroxy)propyl]-3-norbornyl methacrylate.

In exemplary aspects, the hydrophobic random copolymer has a number average molecular weight of about 3 kDa to about 12.5 kDa, about 3 kDa to about 12 kDa, about 3 kDa to about 11 kDa, about 3 kDa to about 10 kDa, about 3 kDa to about 9 kDa, about 3 kDa to about 8 kDa, about 3 kDa to about 7 kDa, about 3 kDa to about 6 kDa, about 3 kDa to about 5 kDa, about 3 kDa to about 4 kDa, about 3.5 kDa to about 12.5 kDa, about 4 kDa to about 12.5 kDa, about 5 kDa to about 12.5 kDa, about 6 kDa to about 12.0 kDa or 12.5 kDa, about 7 kDa to about 12.5 kDa, about 8 kDa to about 12.5 kDa, about 9 kDa to about 12.5 kDa, about 10 kDa to about 12.5 kDa, about 11 kDa to about 12.5 kDa, or about 12 kDa to about 12.5 kDa. In exemplary aspects, the hydrophobic random copolymer has a number average molecular weight of about 5.0 to about 7.0 (e.g., 5.0 kDa, 5.1 kDa, 5.2 kDa, 5.3 kDa, 5.4 kDa, 5.5 kDa, 5.6 kDa, 5.7 kDa, 5.8 kDa, 5.9 kDa, 6.0 kDa, 6.1 kDa, 6.2 kDa, 6.3 kDa, 6.4 kDa, 6.5 kDa, 6.6 kDa, 6.7 kDa, 6.8 kDa, 6.9 kDa, 7.0 kDa). In exemplary aspects, the hydrophobic random copolymer has a number average molecular weight of about 6.6 kDa to about 11.4 kDa, or about 6.6 kDa to about 10.5 kDa, about 6.6 kDa to about 10.0 kDa, about 6.6 kDa to about 9.5 kDa, about 6.6 kDa to about 9.0 kDa, about 6.6 kDa to about 8.5 kDa, about 7.0 kDa to about 11.4 kDa, about 7.5 kDa to about 11.4 kDa, about 8.0 kDa to about 11.4 kDa, about 8.5 kDa to about 11.4 kDa, about 9.0 kDa to about 11.4 kDa, or about 9.5 kDa to about 11.4 kDa.

In exemplary aspects, the hydrophobic random copolymer is made via Atom Transfer Radical Polymerization (ATRP), as further described herein.

In exemplary aspects, the amphiphilic ABC triblock copolymer has a number average molecular weight of about 6.7 kDa to about 19.1 kDa, about 7 kDa to about 19.1 kDa, about 8 kDa to about 19.1 kDa, about 8.5 kDa to about 19.1 kDa, about 9 kDa to about 19.1 kDa, about 9.5 kDa to about 19.1 kDa, about 10 kDa to about 19.0 kDa or about 19.1 kDa, about 10.5 kDa to about 19.1 kDa, about 10.2 kDa to about 18.1 kDa, about 11 kDa to about 19.1 kDa, about 11.5 kDa to about 19.1 kDa, about 12 kDa to about 19.1 kDa, about 12.5 kDa to about 19.1 kDa, about 13 kDa to about 19.1 kDa, about 13.5 kDa to about 19.1 kDa, about 14 kDa to about 19.1 kDa, about 14.5 kDa to about 19.1 kDa, about 15.0 kDa to about 19.1 kDa, about 15.5 kDa to about 19.1 kDa, about 16.0 kDa to about 19.1 kDa, about 16.5 kDa to about 19.1 kDa, about 17.0 kDa to about 19.1 kDa, about 17.5 kDa to about 19.1 kDa, about 18 kDa to about 19.1 kDa, about 18.5 kDa to about 19.1 kDa, about 19 kDa to about 19.1 kDa, about 6.7 kDa to about 19 kDa, about 6.7 kDa to about 18.5 kDa, about 6.7 kDa to about 18 kDa, about 6.7 kDa to about 17.5 kDa, about 6.7 kDa to about 17.0 kDa, about 6.7 kDa to about 16.5 kDa, about 6.7 kDa to about 16 kDa, about 6.7 kDa to about 15.5 kDa, about 6.7 kDa to about 15 kDa, about 6.7 kDa to about 14.5 kDa, about 6.7 kDa to about 14 kDa, about 6.7 kDa to about 13.5 kDa, about 6.7 kDa to about 13.0 kDa, about 6.7 kDa to about 12.5 kDa, about 6.7 kDa to about 12 kDa, about 6.7 kDa to about 11.5 kDa, about 6.7 kDa to about 11 kDa, v, about 6.7 kDa to about 10.5 kDa, about 6.7 kDa to about 10 kDa, about 6.7 kDa to about 9.5 kDa, about 6.7 kDa to about 9 kDa, about 6.7 kDa to about 8.5 kDa, about 6.7 kDa to about 8 kDa, or about 6.7 kDa to about 7.5 kDa. In exemplary aspects, the number average molecular weight is about 10.2 kDa.

In exemplary aspects, the hydrophilic polymer of block A is PEG, the crosslinking polymer of block B is PAA, and the hydrophobic copolymer of block C is a hydrophobic random copolymer comprising MMA and HDFMA. In exemplary embodiments, the amphiphilic ABC triblock copolymer comprises, per unit of tri-block copolymer, about 10 to about 30 (e.g., about 10 to about 25, about 10 to about 20, about 10 to about 15, about 10 to about 12, about 12 to about 30, about 15 to about 30, about 20 to about 30, about 25 to about 30) w/w % PEG. In exemplary embodiments, the amphiphilic ABC triblock copolymer comprises, per unit of tri-block copolymer, about 8 to about 25 (e.g., about 8 to about 20, about 8 to about 15, about 8 to about 10, about 10 to about 25, about 15 to about 25, about 20 to about 25) w/w PAA. In exemplary embodiments, the amphiphilic ABC triblock copolymer comprises, per unit of tri-block copolymer, about 32 to about 77 (e.g., about 32 to about 75, about 32 to about 70, about 32 to about 65, about 32 to about 60, about 32 to about 55, about 32 to about 50, about 32 to about 45, about 32 to about 40, about 32 to about 35, about 35 to about 77, about 40 to about 77, about 45 to about 77, about 50 to about 77, about 55 to about 77, about 60 to about 77, about 65 to about 77, about 70 to about 77, about 75 to about 77) w/w % of the hydrophobic random copolymer.

In exemplary aspects, the ratio of the molecular weight of block C to the molecular weight of block A of the nanobubbles is within a range of about 0.25 to about 4.00. In exemplary aspects, the ratio of the molecular weight of block C to the molecular weight of block A is within a range of about 0.4 to about 3.25, within a range of about 1.0 to about 2.0, or within a range of about 1.5 to about 2.0. In exemplary aspects, the ratio of the molecular weight of block C to the molecular weight of block A is within a range of about 0.25 to about 3.50, about 0.25 to about 3.0, about 0.25 to about 2.50, about 0.25 to about 2.0, about 0.25 to about 1.5, about 0.25 to about 1.0, about 0.75 to about 4.0, about 1.25 to about 4.0, about 1.75 to about 4.0, about 2.25 to about 4.0, about 2.75 to about 4.0, or about 3.25 to about 4.0.

In exemplary aspects, the ratio of the number of units of block C to the number of units of block A is within a range of about 0.10 to about 1.2 (e.g., 0.10, 0.20, 0.30, 0.40, 0.50, 0.60, 0.70, 0.80, 0.90, 1.0, 1.1, 1.2). In exemplary aspects, the ratio of the number of units of block C to the number of units of block A is within a range of about 0.10 to about 1.0. In exemplary aspects, the ratio of the number of units of block C to the number of units of block A is within a range of about 0.4 to about 0.55.

In exemplary aspects, the amphiphilic ABC triblock copolymer comprises ((PEG)$_x$-b-(PAA)$_y$-b-P(MMA-co-HDFMA)$_z$, wherein x is 45 to 113 (e.g., 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109 110, 111, 112, 113) y is 10 to 25 (e.g., 10, 11, 12, 13, 14, 15, 16, 17, 18, 19, 20, 21, 22, 23, 24, 25), and z is 14 to 60 (e.g., 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60). In exemplary embodiments, x is 45, y is 10, and z is 28. In exemplary embodiments, x is 113, y is 11, and z is 52.5.

In exemplary embodiments, the nanobubble of the invention comprises a shell and a core. In exemplary embodiments, the nanobubble comprises a hydrophilic brush, a shell, and a core. In exemplary aspects, the hydrophilic brush comprises or is made of block A of the amphiphilic triblock copolymer, the shell comprises or it made of block B of the triblock copolymer and the core comprises or is made of block C of the triblock copolymer. In exemplary aspects, the shell is crosslinked.

In exemplary embodiments, the hydrophilic polymer of block A is PEG, the crosslinking polymer of block B is PAA, and the hydrophobic random copolymer comprises MMA and HDFMA.

Random copolymers, methods of making the same, and polymers of the invention

Further provided herein is the hydrophobic copolymer of block C of the amphiphilic triblock copolymer.

Also provided is a random copolymer comprising monomers of methyl methacrylate (MMA) and monomers of hexadecafluorodecylmethacrylate (HDFMA), wherein the mole ratio of the monomers of MMA to the monomers of HDFMA is between about 80 and about 95. In exemplary aspects, the hydrophobic copolymer of block C of the amphiphilic triblock copolymer is the same as the random copolymer comprising MMA and HDFMA. In exemplary aspects, the mole ratio of the monomers of MMA to the monomers of HDFMA is between about 80 and about 90. the mole ratio of the monomers of MMA to the monomers of HDFMA is between about 80 and 85. the mole ratio of the monomers of MMA to the monomers of HDFMA is between about 85 and 95. the mole ratio of the monomers of MMA to the monomers of HDFMA is between about 90 and 95. the mole ratio of the monomers of MMA to the monomers of HDFMA is about 80, 81, 82, 83, 84, 85, 86, 87, 88, 89, 90, 91, 92, 93, 94, or 95. In exemplary aspects, the random copolymer has a number average molecular weight within a range of about 3 kDa to about 12.5 kDa, or any of the number average molecule weights described above in the context of hydrophobic random copolymers.

In some aspects, MMA is substituted with another acrylic polymer. In exemplary aspects, the acrylic polymer comprises a structure of Formula I:

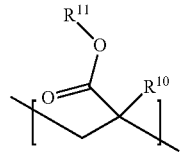

[Formula I]

In some embodiments, R$^{10}$ is hydrogen, methyl, ethyl, or propyl and R$^{11}$ is C$_1$-C$_{50}$ alkyl. Suitable monomers of Formula I for use in the present invention according to these embodiments include, for example, methyl acrylate, ethyl acrylate, propyl acrylate, isopropyl acrylate, n-butyl acrylate, isobutyl acrylate, tert-butyl acrylate, hexyl acrylate, isooctyl acrylate, isodecyl acrylate, octadecyl acrylate, lauryl acrylate, 2-ethylhexyl acrylate, 4-tert-butylcyclohexyl acrylate, 3,5,5-trimethylhexyl acrylate, isobornyl acrylate, ethyl methacrylate, butyl methacrylate, isobutyl methacrylate, tert-butyl methacrylate, hexyl methacrylate, 2-ethylhexyl methacrylate, isodecyl methacrylate, lauryl methacrylate, stearyl methacrylate, cyclohexyl methacrylate, 3,3,5-trimethylcyclohexyl methacrylate, ethyl 2-ethylacrylate, ethyl 2-propylacrylate, and isobornyl methacrylate. In exemplary aspects, the acrylic polymer is ethyl methacrylate, butyl methacrylate, isobutyl methacrylate, tert-butyl methacrylate, or hexyl methacrylate.

In exemplary aspects, HDFMA substituted with another fluorinated monomer. In exemplary aspects, the fluorinated monomer comprises a structure of Formula II:

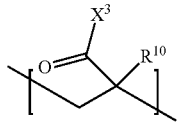

[Formula II]

In some embodiments, suitable monomers for use in the present invention include fluorinated acrylic monomers. Suitable monomers of Formula VII for use in the present invention according to these embodiments include, for example, 2,2,3,3,4,4,5,5,6,6,7,7-dodecafluoroheptyl acrylate, 4,4,5,5, 6,6,7,7,8,9,9,9-dodecafluoro-2-hydroxy-8-(trifluoromethyl) nonyl methacrylate, 3,3,4,4,5,5,6,6,7,7,8,8,9,9,10,10,11,12, 12,12-eicosafluoro-11-(trifluoromethyl)dodecyl methacrylate, 3,3,4,4,5,5,6,6,7,7,8,8,9,9,10,10,11,11,12,12, 12-heneicosafluorododecyl acrylate, 3,3,4,4,5,5,6,6,7,7,8,8, 9,9,10,10,11,11,12,12,12-heneicosafluorododecyl methacrylate, 3,3,4,4,5,5,6,6,7,7,8,8,9,9,10,10,10-heptadecafluorodecyl methacrylate, 2,2,3,3,4,4,4-heptafluorobutyl acrylate, 2,2,3,3,4,4,4-heptafluorobutyl methacrylate, 2,2,3,3,4,4,4-hexafluorobutyl acrylate, 2,2,3,4,4, 4-hexafluorobutyl methacrylate, 1,1,1,3,3,3-hexafluoroisopropyl acrylate, 1,1,1,3,3,3-hexafluoroisopropyl methacrylate, 2,2,3,3,4,4,5,5-octafluoropentyl acrylate, 2,2,3,3,4,4,5, 5-octafluoropentyl methacrylate, 2,2,3,3,3- pentafluoropropyl acrylate, 2,2,3,3,3-pentafluoropropyl methacrylate, 1H,1H,2H,2H-perfluorodecyl acrylate, 2,2,3,3-tetrafluoropropyl methacrylate, 3,3,4,4,5,5,6,6,7,7,8,8,8-tridecafluorooctyl acrylate, 3,3,4,4,5,5,6,6,7,7,8,8,8-tridecafluorooctyl methacrylate, 2,2,2-trifluoroethyl methacrylate, 1,1,1-trifluoro-2-(trifluoromethyl)-2-hydroxy-4-methyl-5-pentyl methacrylate, and 2-[(1',1',1'-trifluoro-2'-(trifluoromethyl)-2'-hydroxy)propyl]-3-norbornyl methacrylate. In exemplary aspects, the fluorinated monomer is 4,4,5,5,6,6,7,7,8,9,9,9-dodecafluoro-2-hydroxy-8-(trifluoromethyl)nonyl methacrylate, 3,3,4,4,5,5,6,6,7,7,8,8,9,9,10,10,11,12,12,12-eicosafluoro-11-(trifluoromethyl) dodecyl methacrylate, 3,3,4,4,5,5,6,6,7,7,8,8,9,9,10,10,11,11,12,12,12-heneicosafluorododecyl methacrylate, 3,3,4,4,5,5,6,6,7,7,8,8,9,9,10,10,10-heptadecafluorodecyl methacrylate, 2,2,3,3,4,4,4-heptafluorobutyl methacrylate, 2,2,3,4,4,4-hexafluorobutyl methacrylate, 1,1,1,3,3,3-hexafluoroisopropyl methacrylate, 2,2,3,3,4,4,5,5-octafluoropentyl methacrylate, 2,2,3,3,3-pentafluoropropyl methacrylate, 2,2,3,3-tetrafluoropropyl methacrylate, 3,3,4,4,5,5,6,6,7,7,8,8,8-tridecafluorooctyl methacrylate, 2,2,2-trifluoroethyl methacrylate, 1,1,1-trifluoro-2-(trifluoromethyl)-2-hydroxy-4-methyl-5-pentyl methacrylate, or 2-[(1',1',1'-trifluoro-2'-(trifluoromethyl)-2'-hydroxy)propyl]-3-norbornyl methacrylate.

In some aspects, the random copolymers are synthesized by free radical polymerization. In some aspects, the free radical polymerization is controlled (or living) radical polymerization CRP. See, e.g., Bisht et al., *Living Free-Radical Polymerization—A Review*, J. Macromol. Sci.—Polymer Reviews C41(3): 139-173 (2001). Examples of living radical polymerization include atom transfer radical polymerization (ATRP) and stable free radical polymerization (SFRP). In exemplary aspects, the random copolymers are made through a process called Atom Transfer Radical Polymerization (ATRP). ATRP is a well-known method by those skilled in the art for the synthesis of random copolymers. See, e.g., Matyjaszewski, *Atom Transfer Radical Polymerization (ATRP): Current Status and Future Perspectives*, Macromolecules 45(10):4015-4039 (2012). In exemplary aspects, the random copolymers are produced through introducing into a Schlenk tube under argon CuBr, N-(n-Pentyl)-2-pyridylmethanimine, protected maleimide functional initiator, MMA, HDFMA and toluene.

In exemplary aspects, the number average molecular weight of the random copolymer of the invention is between about 3 kDa and 12.5 kDa, as described for the hydrophobic copolymer of block C. In exemplary aspects, the number average molecular weight of the random copolymer of the invention is between about 6.0 kDa and 12.0 kDa, optionally, about 6.6 kDa or about 11.4 kDa.

The invention provides a method of making a random copolymer comprising monomers of methyl methacrylate (MMA) and monomers of hexadecafluorodecylmethacrylate (HDFMA), comprising introducing into a Schlenk tube under argon CuBr, N-(n-Pentyl)-2-pyridylmethanimine, protected maleimide functional initiator, MMA, HDFMA and toluene. In exemplary aspects, the method comprises the steps of (i) degassing by three freeze-pump-thaw cycles, (ii) heating at 90° C. under stirring conditions the Schlenk tube in an oil bath for a time between 1 and 2 hours, thereby obtaining a mixture, (iii) diluting the mixture with THF, thereby obtaining a diluted mixture, (v) passing the diluted mixture through an alumina column to remove complex salts, (vi) precipitating in heptane, and (vii) filtering, thereby obtaining a random copolymer comprising MMA and HDFMA. In exemplary aspects, the feed ratio of (MMA monomer/HDFMA monomers) is between 80/20 and 95/5 mol %. In exemplary aspects, 1.5 mL, $1.4 \times 10^{-2}$ mol MMA and 1.25 mL, $3.74 \times 10^{-3}$ HDFMA are used. In exemplary aspects, CuBr (33.5 mg, $2.33 \times 10^{-4}$ mol), N-(n-Pentyl)-2-pyridylmethanimine (86.5 µL, $4.68 \times 10^{-4}$ mol), protected maleimide functional initiator (83.3, $2.23 \times 10^{-4}$ mmol), MMA (1.5 mL, $1.4 \times 10^{-2}$ mol), HDFMA (1.25 mL, $3.74 \times 10^{-3}$) and 2.5 mL Toluene are introduced in a Schlenk tube under argon.

The random copolymer produced in this manner are provided herein.

Also provided is a block copolymer comprising a block of the random copolymer of the invention, or otherwise described herein. In exemplary aspects, the block copolymer comprises a first block A, a second block B, and a third block C, wherein at least one of A, B, and C is hydrophobic and at least one of A, B, and C is hydrophilic. In exemplary aspects, the first block, A, comprises a hydrophilic polymer, the second block, B, comprises a hydrophilic, cross-linkable polymer, and the third block, C, comprises the hydrophobic random copolymer. Block A, block B, and block C are further described herein. In exemplary aspects, the hydrophilic polymer of block A is polyethylene glycol (PEG), poly(trimethyl ethyl methacrylate), poly(acrylic acid), or polyn (N-2-hydroxy propyl)methacrylamide (PHPMA). In exemplary aspects, the crosslinking polymer of the block B is polyacrylic acid (PAA) or poly(hydroxyl ethyl acrylate) (PHEA) or PPFPA. In exemplary aspects, the block copolymer has an average molecular weight of about 6.7 kDa to about 19.1 kDa, about 10 kDa to about 19 kDa, about 10.2 kDa, or about 18.1 kDa.

Also provided herein is an amphiphlic ABC triblock copolymer. The amphiphilic block copolymer comprising a block A comprises a hydrophilic polymer, block B comprises a crosslinking polymer, and block C comprises a hydrophobic copolymer comprising (i) methyl methacrylate (MMA) and (ii) a fluorinated monomer, wherein the fluorinated monomer is present in the hydrophobic copolymer of block C at 25 mole percent or less, comprising ((hydrophilic polymer of block A)$_x$-b-(crosslinking polymer of block B)$_y$-b-P(MMA-co-fluorinated monomer), wherein x is 45 to 113, y is 10 to 25, and z is 14 to 60. In exemplary aspects, x is 45, y is 10, and z is 28 or x is 113, y is 11, and z is 52.5. Block A, block B, and block C are further described herein. Also, the average molecular weight of the ABC triblock copolymer is described herein.

The invention provides any nanobubble comprising the inventive random copolymer, block copolymer of amphiphilic ABC triblock copolymer described herein.

Targeting Ligands

In exemplary embodiments, the nanobubble comprises a targeting ligand, and optionally the targeting ligand is attached to a tip of the hydrophilic polymer of block A. In exemplary aspects, at least 10% of the hydrophilic polymer of block A is attached at its tip to a targeting ligand. In exemplary aspects, at least 25% of the hydrophilic polymer of block A is attached at its tip to a targeting ligand. In exemplary aspects, at least 50% of the hydrophilic polymer of block A is attached at its tip to a targeting ligand. In exemplary aspects, at least 75% of the hydrophilic polymer of block A is attached at its tip to a targeting ligand.

The targeting ligand may be any peptide, protein, antibody, or fragment thereof, aptamer, or like that targets the nanobubble to a particular cell type or tissue type. Antibodies, antigen-binding fragments thereof, and aptamers are described below.

In exemplary embodiments, the cell which is targeted by the nanobubble expresses a molecule that specifically binds to the targeting ligand of the nanobubble. In exemplary aspects, the cell is a cancer cell which expresses a molecule that specifically binds to the targeting ligand of the nanobubble, and the targeting ligand is considered as a "cancer-cell targeting ligand."

Numerous molecules expressed by cancer cells are known in the art, and it is contemplated that the targeting ligand of the nanobubble of the invention binds to one or more of these molecules. In exemplary aspects, targeting ligand binds to one or more of: alphafetoprotein (AFP), which is known to be expressed by germ cell tumor cells and heptaocellular tumor cells, carcinoembryonic antigen (CEA), which is known to be expressed by bowel cancer cells, CA-125, which is known to be expressed by ovarian cancer cells, MUC-1, which is known to be expressed by breast cancer cells, epithelial tumor antigen (ETA), which is known to be expressed by breast cancer cells, tyrosinase, which is known to be expressed by malignant melanoma cells, melanoma-associated antigen, which is known to be expressed by malignant melanoma cells, prostate specific membrane antigen, which is known to be expressed by prostate cancer cells, CA19-9, which is known to be expressed by pancreatic, colorectal, gastric, and hepatic carcinoma cells, CA15-3, which is known to be expressed by breast cancer cells, Her-2, which is known to be expressed by breast cancer cells. In exemplary aspects, the targeting ligand binds to prostate-specific membrane antigen (PSMA). In exemplary aspects, the targeting ligand is a PSMA-specific antibody. In exemplary aspects, the targeting ligand binds to a receptor for N-acetyl-galactosamine, galactose, or an EPPT1 peptide. In exemplary aspects, the targeting ligand is N-acetyl-galactosamine, galactose, or an EPPT1 peptide. The amino acid sequence of the EPPT1 peptide is known in the art. See e.g. U.S. Publication No. 2006/0269479, Mandarano et al. *Biomed. Imaging Interv. J.*, 6:e13 (2010).

The targeting ligand may be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, and the like. In this regard, the antibody may be considered as a mammalian or avian antibody, e.g., a mouse antibody, rabbit antibody, goat antibody, horse antibody, chicken antibody, hamster antibody, human antibody, and the like.

The antibody can have any level of affinity or avidity for the antigen which is expressed by the cell being targeted by the nanobubble. Binding constants, including dissociation constants, may be determined by methods known in the art, including, for example, methods which utilize the principles of surface plasmon resonance, e.g., methods utilizing a Biacore™ system. In accordance with the foregoing, in some embodiments, the antibody is in monomeric form, while in other embodiments, the antibody is in polymeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the binding agent.

In some embodiments, the antibody can be a genetically-engineered antibody, e.g., a single chain antibody, a humanized antibody, a chimeric antibody, a CDR-grafted antibody, an antibody which includes portions of CDR sequences specific for the antigen expressed by the cell being targeted by the nanobubble, a humaneered antibody, a bispecific antibody, a trispecific antibody, and the like. Genetic engineering techniques also provide the ability to make fully human antibodies in a non-human source.

In some aspects, the antibody is a chimeric antibody. The term "chimeric antibody" is used herein to refer to an antibody containing constant domains from one species and the variable domains from a second, or more generally, containing stretches of amino acid sequence from at least two species.

In some aspects, the antibody is a humanized antibody. The term "humanized" when used in relation to antibodies is used to refer to antibodies having at least CDR regions from a nonhuman source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

Use of the terms "chimeric or humanized" herein is not meant to be mutually exclusive, and rather, is meant to encompass chimeric antibodies, humanized antibodies, and chimeric antibodies that have been further humanized. Except where context otherwise indicates, statements about (properties of, uses of, testing, and so on) chimeric antibodies of the invention apply to humanized antibodies of the invention, and statements about humanized antibodies of the invention pertain also to chimeric antibodies. Likewise, except where context dictates, such statements also should be understood to be applicable to antibodies and antigen binding fragments of such antibodies.

The targeting ligand is in some aspects an antigen binding fragment of an antibody, which specifically binds to an antigen expressed by the cell being targeted by the nanobubble, in accordance with the disclosures herein. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like. Antibody fragments of the invention, however, are not limited to these exemplary types of antibody fragments.

A domain antibody comprises a functional binding unit of an antibody, and can correspond to the variable regions of either the heavy ($V_H$) or light ($V_L$) chains of antibodies. A domain antibody can have a molecular weight of approximately 13 kDa, or approximately one-tenth of a full antibody. Domain antibodies may be derived from full antibodies such as those described herein. The antigen binding fragments in some embodiments are monomeric or polymeric, bispecific or trispecific, bivalent or trivalent.

Antibody fragments that contain the antigen binding, or idiotype, of the antibody molecule may be generated by techniques known in the art. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment, and the two Fab' fragments which may be generated by treating the antibody molecule with papain and a reducing agent.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)).

Recombinant antibody fragments, e.g., scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., Biomol Eng. 2001 18:95-108, (2001) and Todorovska et al., *J Immunol Methods.* 248:47-66, (2001).

Bispecific antibodies (bscAb) are molecules comprising two single-chain Fv fragments joined via a glycine-serine linker using recombinant methods. The V light-chain ($V_L$) and V heavy-chain ($V_H$) domains of two antibodies of interest in exemplary embodiments are isolated using standard PCR methods. The $V_L$ and $V_H$ cDNA's obtained from each hybridoma are then joined to form a single-chain fragment in a two-step fusion PCR. Bispecific fusion proteins are prepared in a similar manner. Bispecific single-chain antibodies and bispecific fusion proteins are antibody substances included within the scope of the present invention. Exemplary bispecific antibodies are taught in U.S. Patent Application Publication No. 2005-0282233A1 and International Patent Application Publication No. WO 2005/087812, both applications of which are incorporated herein by reference in their entirety.

Suitable methods of making antibodies are known in the art. For instance, standard hybridoma methods are described in, e.g., Harlow and Lane (eds.), Antibodies: A Laboratory Manual, CSH Press (1988), and CA. Janeway et al. (eds.), Immunobiology, $5^{th}$ Ed., Garland Publishing, New York, N.Y. (2001)).

Monoclonal antibodies for use in the invention may be prepared using any technique which provides for the production of antibody molecules by continuous cell lines in culture. These include but are not limited to the hybridoma technique originally described by Koehler and Milstein (Nature 256: 495-497, 1975), the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985).

When the hybridoma technique is employed, myeloma cell lines may be used. Such cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/15XXO Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Aptamers

In exemplary aspects, the targeting ligand of the nanobubble of the invention is an aptamer. For more on aptamers, see, generally, Gold, L., Singer, B., He,Y.Y., Brody. E., "Aptamers As Therapeutic And Diagnostic Agents," J. Biotechnol. 74:5-13 (2000). Relevant techniques for generating aptamers may be found in U.S. Pat. No. 6,699,843, which is incorporated by reference in its entirety.

Ultrasound Contrast Agents

In exemplary aspects, the nanobubble has a core comprising or encapsulating an ultrasound contrast agent. In exemplary aspects, the ultrasound contrast agent has a boiling point which is greater than about 25° C. In exemplary aspects, the ultrasound contrast agent is selected from the group consisting of: perfluorocarbon (PFC), perfluoropentane (PFP), perfluoropropane, perfluorobutane, and perfluorohexane. In exemplary aspects, the loaded % of the ultrasound contrast agent is between about 0.5% and about 3% or about 1% to about 2%.

Therapeutic Agents

In exemplary embodiments, the nanobubble comprises a therapeutic agent. In exemplary aspects, the nanobubble comprises a core coated with an oil and the oil comprises a therapeutic agent.

Suitable therapeutic agents for use herein include without limitation analgesics and analgesic combinations, anesthetics, anorexics, anti-allergics, antiarthritics, antiasthmatic agents, antibiotics, anticholinergics, anticonvulsants, antidepressants, antihemophilics, antidiabetic agents, antidiarrheals, antifungals, antigens, antihistamines, antihypertensives, anti-inflammatories, antimigraine preparations, antinauseants, antineoplastics, antiparkinsonism drugs, antiprotozoans, antipruritics, antipsychotics, antipyretics, antispasmodics, antivirals, calcium channel blockers, cardiovascular preparations, central nervous system stimulants, contraceptives, cough and cold preparations including decongestants, diuretics, enzyme inhibitors, enzymes, genetic material including DNA and RNA, growth factors, growth hormones, hormone inhibitors, hypnotics, immunonanobubbles, immunosuppressive agents, microbicides, muscle relaxants, parasympatholytics, peptides, peripheral and cerebral vasodilators, proteins, psychostimulants, receptor agonists, sedatives, spermicides and other contraceptives, steroids, sympathomimetics, tranquilizers, vaccines, vasodilating agents including general coronary, viral vectors, small organic molecules, and combinations thereof.

Antiviral agents include, but are not limited to, nucleoside phosphonates and other nucleoside analogs, 5-amino-4-imidazolecarboxamide ribonucleotide (AICAR) analogs, glycolytic pathway inhibitors, anionic polymers, and the like, more specifically: antiherpes agents such as acyclovir, famciclovir, foscarnet, ganciclovir, idoxuridine, sorivudine, trifluridine, valacyclovir, and vidarabine; and other antiviral agents such as abacavir, adefovir, amantadine, amprenavir, cidofovir, delviridine, 2-deoxyglucose, dextran sulfate, didanosine, efavirenz, entecavir, indinavir, interferon alpha and PEGylated interferon, interferon alfacon-1, lamivudine, nelfinavir, nevirapine, ribavirin, rimantadine, ritonavir, saquinavir, squalamine, stavudine, telbivudine, tenofovir, tipranavir, valganciclovir, zalcitabine, zidovudine, zintevir, and mixtures thereof. Still other antiviral agents are glycerides, particularly monoglycerides, which have antiviral activity. One such agent is monolaurin, the monoglyceride of lauric acid.

Anti-inflammatory agents include, but are not limited to, corticosteroids, e.g., lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or higher potency corticosteroids such as clobetasol propionate, betamethasone benzoate, betamethasone diproprionate, diflorasone diacetate, fluocinonide, mometasone furoate, triamcinolone acetonide, and mixtures thereof.

Antibiotic agents include, e.g., those of the lincomycin family, such as lincomycin per se, clindamycin, and the 7-deoxy,7-chloro derivative of lincomycin (i.e., 7-chloro-6,7,8-trideoxy-6-[[(1-methyl-4-propyl-2-pyrrolidinyl)carbonyl]amino]-1-thio-L-threo-alpha-D-galacto-octopyranoside); other macrolide, aminoglycoside, and glycopeptide antibiotics such as erythromycin, clarithromycin, azithromycin, streptomycin, gentamicin, tobramycin, amikacin, neomycin, vancomycin, and teicoplanin; antibiotics of the tetracycline family, including tetracycline per se, chlortetracycline, oxytetracycline, demeclocycline, rolitetracycline, methacycline and doxycycline; and sulfur-based antibiotics, such as the sulfonamides sulfacetamide, sulfabenzamide, sulfadiazine, sulfadoxine, sulfamerazine, sulfamethazine, sulfamethizole, and sulfamethoxazole; streptogramin antibiotics such as quinupristin and dalfopristin; and quinolone antibiotics such as ciprofloxacin, nalidixic acid, ofloxacin, and mixtures thereof.

Antifungal agents include, e.g., miconazole, terconazole, isoconazole, itraconazole, fenticonazole, fluconazole, ketoconazole, clotrimazole, butoconazole, econazole, metronidazole, 5-fluorouracil, amphotericin B, and mixtures thereof.

Antihemophilic agents include, e.g., antifibrinolytic amino acids, aprotinin, 1-deamino-8-d-arginine vasopressin, aminocaproic acid, tranexamic acid and conjugated estrogens, and mixtures thereof (Mannucci et al. (1998). New. Eng. J. Med. 339:245)

Other anti-infective agents include miscellaneous antibacterial agents such as chloramphenicol, spectinomycin, polymyxin B (colistin), and bacitracin, anti-mycobacterials such as such as isoniazid, rifampin, rifabutin, ethambutol, pyrazinamide, ethionamide, aminosalicylic acid, and cycloserine, and antihelminthic agents such as albendazole, oxfendazole, thiabendazole, and mixtures thereof.

In exemplary aspects, the therapeutic agent is an anticancer therapeutic. The anti-cancer therapeutic may be any of those known in the art, including, but not limited to, platinum complex, verapamil, podophyllotoxin, carboplatin, procarbazine, mechlorethamine, cyclophosphamide, camptothecin, ifosfamide, melphalan, chlorambucil, busulfan, nitrosourea, adriamycin, dactinomycin, daunorubicin, doxorubicin, bleomycin, plicamycin, mitomycin, etoposide (VP16), tamoxifen, taxol, transplatinum, 5-fluorouracil, vincristine, vinblastine, methotrexate, gemcitabine and other similar anti-cancer agents. See, for example, the Physician's Desk reference and Goodman and Gilman's "Pharmaceutical Basis of Therapeutics" ninth edition, Eds. Hardman et al., 1996.

Any of the therapeutic agents may be administered in the form of a salt, ester, amide, prodrug, conjugate, active metabolite, isomer, fragment, analog, or the like, provided that the salt, ester, amide, prodrug, conjugate, active metabolite, isomer, fragment, or analog is pharmaceutically acceptable and pharmacologically active in the present context. Salts, esters, amides, prodrugs, conjugates, active metabolites, isomers, fragments, and analogs of the agents may be prepared using standard procedures known to those skilled in the art of synthetic organic chemistry and described, for example, by J. March, Advanced Organic Chemistry: Reactions, Mechanisms and Structure, 5th Edition (New York: Wiley-InterScience, 2001).

Methods of Treatment

The nanobubbles of the invention may be used in a method of treating cancer in a subject. In exemplary aspects, the method comprises administering to the subject a nanobubble of the invention and ultrasound. In exemplary aspects, the nanobubble comprises a targeting ligand that binds to a marker or molecule expressed on the surface of the cells of the cancer being treated. Suitable targeting ligands are known in the art and are also described herein. In exemplary aspects, the targeting ligand is a binding agent that binds to PSMA (e.g., a PSMA-specific antibody or aptamer), or is N-acetyl-galactosamine, galactose, or an EPPT1 peptide. In exemplary aspects, the nanobubble comprises a core coated with an oil comprising an anti-cancer therapeutic agent. Suitable anti-cancer therapeutic agents are known in the art and are also described herein. In exemplary aspects, the anti-cancer therapeutic agent is doxorubicin, docetaxel, or cabzitaxel.

Ultrasound

In the methods described herein, ultrasound is applied to the subject. In exemplary aspects, the ultrasound is applied at a pulse repetition frequency and/or at a peak negative pressure described herein.

In exemplary aspects, ultrasound pulses with a peak negative pressure which is less than what is normally used in histotripsy (pulse repetition frequency of 50 Hz, peak negative pressure of 25 MPa) is used in the inventive methods of treatment. In exemplary aspects, ultrasound pulses are applied at a peak negative pressure of less than 25 MPa. In exemplary aspects, ultrasound pulses are applied at a peak negative pressure within a range of about between 7 MPa and 30 MPa, or about 7 MPa to about 25 MPa, or about 7 MPa to about 22 MPa or about 10 MPa and 25 MPa (e.g., within a range of about 10 MPa to about 22.5 MPa, within a range of about 10 MPa to about 20 MPa, within a range of about 10 MPa to about 17.5 MPa, within a range of about 10 MPa to about 15 MPa, within a range of about 10 MPa to about 12.5 MPa, within a range of about 12.5 MPa to about 25 MPa, within a range of about 15 MPa to about 25 MPa, within a range of about 17.5 MPa to about 25 MPa, within a range of about 17.5 MPa to about 25 MPa, within a range of about 20 MPa to about 25 MPa, within a range of about 22.5 MPa to about 25 MPa, within a range of about 12.5 MPa to about 22.5 MPa, or within a range of about 15 MPa to about 20 MPa).

Cancer

The cancer treatable by the methods disclosed herein may be any cancer, e.g., any malignant growth or tumor caused by abnormal and uncontrolled cell division that may spread to other parts of the body through the lymphatic system or the blood stream. The cancer in exemplary aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In exemplary aspects, the cancer is a prostate cancer (e.g., a benign prostate hyperplasia), breast cancer, liver cancer, or pancreatic cancer.

Pharmaceutical Compositions and Formulations

In exemplary embodiments, the nanobubble of the invention, is formulated into a pharmaceutical composition, along with a pharmaceutically acceptable carrier, diluent, or excipient. In this regard, the invention further provides pharmaceutical compositions comprising a nanobubble of the invention, which composition is intended for administration to a subject, e.g., a mammal.

In some embodiments, the nanobubble is present in the pharmaceutical composition at a purity level suitable for administration to a subject. In some embodiments, the nanobubble has a purity level of at least about 90%, about 91%, about 92%, about 93%, about 94%, about 95%, about 96%, about 97%, about 98% or about 99%, and a pharmaceutically acceptable diluent, carrier or excipient.

Depending on the route of administration, the particular nanobubble intended for use, as well as other factors, the pharmaceutical composition may comprise additional pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface nanobubbles, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, which discloses various components used in formulating pharmaceutically acceptable compositions and known techniques for the preparation thereof.

Routes of Administration

With regard to the invention, the nanobubbles, or the pharmaceutical composition comprising the same, may be administered to the subject via any suitable route of administration. The following discussion on routes of administration is merely provided to illustrate exemplary embodiments and should not be construed as limiting the scope in any way.

Formulations suitable for oral administration can consist of (a) liquid solutions, such as an effective amount of the nanobubble of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the nanobubble of the present disclosure in a flavor, usually sucrose and acacia or tragacanth, as well as pastilles comprising the nanobubble of the present disclosure in an inert base, such as gelatin and glycerin, or sucrose and acacia, emulsions, gels, and the like containing, in addition to, such excipients as are known in the art.

The nanobubbles of the present disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the nanobubble is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The nanobubble of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the nanobubble of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the nanobubble of the invention can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the nanobubble of the disclosure can be formulated as inclusion complexes, such as cyclodextrin inclusion complexes, or liposomes.

Dosages

The nanobubbles of the disclosure are believed to be useful in methods of treating cancer in a subject, and other methods, as described herein. For purposes of the disclosure, the amount or dose of the nanobubble administered should be sufficient to effect, e.g., a therapeutic or prophylactic response, in the subject or animal over a reasonable time frame. For example, the dose of the nanobubble of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular nanobubble and the condition of the animal (e.g., human), as well as the body weight of the animal (e.g., human) to be treated.

Controlled Release Formulations

In some embodiments, the nanobubbles described herein can be modified into a depot form, such that the manner in which the nanobubble of the invention is released into the body to which it is administered is controlled with respect to time and location within the body (see, for example, U.S. Pat. No. 4,450,150). Depot forms of nanobubbles of the invention can be, for example, an implantable composition comprising the nanobubbles and a porous or non-porous material, such as a polymer, wherein the nanobubble is encapsulated by or diffused throughout the material and/or degradation of the non-porous material. The depot is then implanted into the desired location within the body of the subject and the nanobubble is released from the implant at a predetermined rate.

The pharmaceutical composition comprising the nanobubble in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art, and may be applicable to such controlled release formulations comprising nanobubbles. See, for example, Qian et al., *J Pharm* 374: 46-52 (2009) and International Patent Application Publication Nos. WO 2008/130158, WO2004/033036; WO2000/032218; and WO 1999/040942.

Timing of Administration

The disclosed pharmaceutical compositions and formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data, and initially gauged based on timing used for other nanoparticle-based therapeutics.

Combinations

In some embodiments, the nanobubbles described herein are administered alone, and in alternative embodiments, the nanobubbles described herein are administered in combination with another therapeutic agent, e.g., another nanobubble of the invention of different type (e.g., structure), or another anti-cancer therapeutic. Suitable therapeutic agents and anti-cancer therapeutics are described in the art and herein. In some embodiments, the other therapeutic is a chemotherapeutic agent. In some aspects, the chemotherapeutic agent is a DNA crosslinker or an agent that targets DNA synthesis (e.g., cisplatin). In some aspects, the chemotherapeutic agent comprises any of a platinum coordination compound (e.g., cisplatin), topoisomerase inhibitor (e.g., camptothecin), antibiotic compound (e.g., doxorubicin, mitomycin, bleomycin, daunorubicin, streptozocin), an antimitotic alkaloid (e.g., vinblastine, vincristine, videsine, Taxol, vinorelbine), or an anti-viral (e.g., gemcitabine).

In exemplary embodiments, the nanobubble is administered simultaneously as the other therapeutic. In alternative embodiments, the nanobubble is administered either before or after the other therapeutic.

Diagnostic Methods

Provided herein are diagnostic-type methods utilizing the nanobubbles of the invention. For example, a method of determining the presence of a cancer cell in a subject is provided.

The method comprises the steps of administering to the subject (i) a nanobubble of the invention, wherein the nanobubble comprises (a) a cancer cell-targeting ligand which binds to a marker of the cancer cell and (b) an ultrasound contrast agent, and (ii) ultrasound. In exemplary aspects, the nanobubble comprises a cancer cell-targeting ligand, such as any of those described herein. In exemplary aspects, the ultrasound is applied after the nanobubbles are administered to the subject. Without being bound to any particular theory, the nanobubbles localize to the cancer via the cancer cell targeting ligand, allowing imaging of the cancer. In exemplary aspects, the cancer cell which is targeted by the nanobubbles is any one of the aforementioned cancers, e.g., prostate cancer, breast cancer, liver cancer, pancreatic cancer, or prostate hyperplasia. In exemplary aspects, the targeting ligand is any one of those described herein, e.g., a PSMA-specific aptamer or antibody, N-acetyl-galactosamine, galactose, or EPPT1 peptide.

The detection of cancer cells provides a basis for diagnosis, staging, monitoring, or prognosis of cancer. Accordingly, the invention also provides a method of diagnosing, staging, monitoring, or prognosing a cancer in a subject. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound. In exemplary aspects, the nanobubble comprises a cancer cell-targeting ligand. In exemplary aspects, the ultrasound is applied after the nanobubbles are administered to the subject. Wherein the cancer is monitored, the method comprises administration of the nanobubble comprising the cancer cell-targeting ligand, ultrasound contrast agent, with ultrasound occurs at a first and second time point, wherein the first time point before the second time point.

The detection of cancer cells also provides a basis for the determination of a subject's need for anti-cancer treatment and determination of efficacy of an anti-cancer treatment in a subject. The detection of cancer cells additionally provides a basis for testing a compound for anti-cancer therapeutic activity. Accordingly, the invention further provides a method of determining a subject's need for anti-cancer treatment, a method of determining efficacy of an anti-cancer treatment in a subject, a method of screening a compound for anti-cancer therapeutic activity. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound. In exemplary aspects, the nanobubble comprises a cancer cell-targeting ligand. In exemplary aspects, the ultrasound is applied after the nanobubbles are administered to the subject. In exemplary aspects of the inventive method of determining efficacy of an anti-cancer treatment in a subject, the administration of the nanobubble comprising the cancer cell-targeting ligand, ultrasound contrast agent, with ultrasound occurs at a first and second time point, wherein the first time point occurs before treatment and the second time point occurs after treatment. With regard to the inventive method of testing a compound for anti-cancer therapeutic activity, the administration of the nanobubble comprising the cancer cell-targeting ligand, ultrasound contrast agent, with ultrasound occurs at a first and second time point, wherein the first time point occurs before administration of the compound and the second time point occurs after administration of the compound.

The detection of cancer cells provides a basis the determination of a subject's risk for cancer, or for monitoring the risk. Accordingly, the invention furthermore provides a method of determining a subject's risk for cancer and a method of monitoring a subject's risk for cancer. In exemplary aspects, the method comprises the steps of administering to the subject (i) a nano-sized particle, e.g., a nanobubble, a nanodroplet, of the invention, wherein the nano-sized particle comprises (a) a cancer cell-targeting ligand which binds to a marker of the cancer cell and (b) an ultrasound contrast agent, and (ii) ultrasound. In exemplary aspects, the nanobubble comprises a cancer cell-targeting ligand. In exemplary aspects, the ultrasound is applied after the nanobubbles are administered to the subject. Wherein a risk is monitored, the method comprises administration of the nanobubble comprising the cancer cell-targeting ligand, ultrasound contrast agent, with ultrasound occurs at a first and second time point, wherein the first time point before the second time point.

Subjects

In exemplary embodiments of the invention, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In exemplary aspects, the mammal is a human.

Kits

The nanobubbles of the invention may be provided as a kit or a package or unit dose. As used herein, the term "unit dose" is a discrete amount of a composition, e.g., a therapeutic composition, dispersed in a suitable carrier. Accordingly, the invention further provide kits, packages, and unit doses, each of which comprises a nanobubble in accordance with the descriptions herein.

In exemplary embodiments, the components of the kit/unit dose are packaged with instructions for administration to a subject, e.g., a human. In exemplary embodiments, the kit comprises one or more devices for administration to a subject, e.g., a needle and syringe, a dropper, a measuring spoon or cup or like device, an inhaler, and the like. In exemplary aspects, the nanobubbles of the invention, are pre-packaged in a ready to use form, e.g., a syringe, an intravenous bag, an inhaler, a tablet, capsule, etc. In some aspects, the kit further comprises other therapeutic or diagnostic agents or pharmaceutically acceptable carriers (e.g., solvents, buffers, diluents, etc.), including any of those described herein. In exemplary aspects, the kit comprises a source of ultrasound.

The following examples are given merely to illustrate the present invention and not in any way to limit its scope.

EXAMPLES

Example 1

This example describes the design and synthesis of a set of nanobubbles of the invention.

Figure 1A:
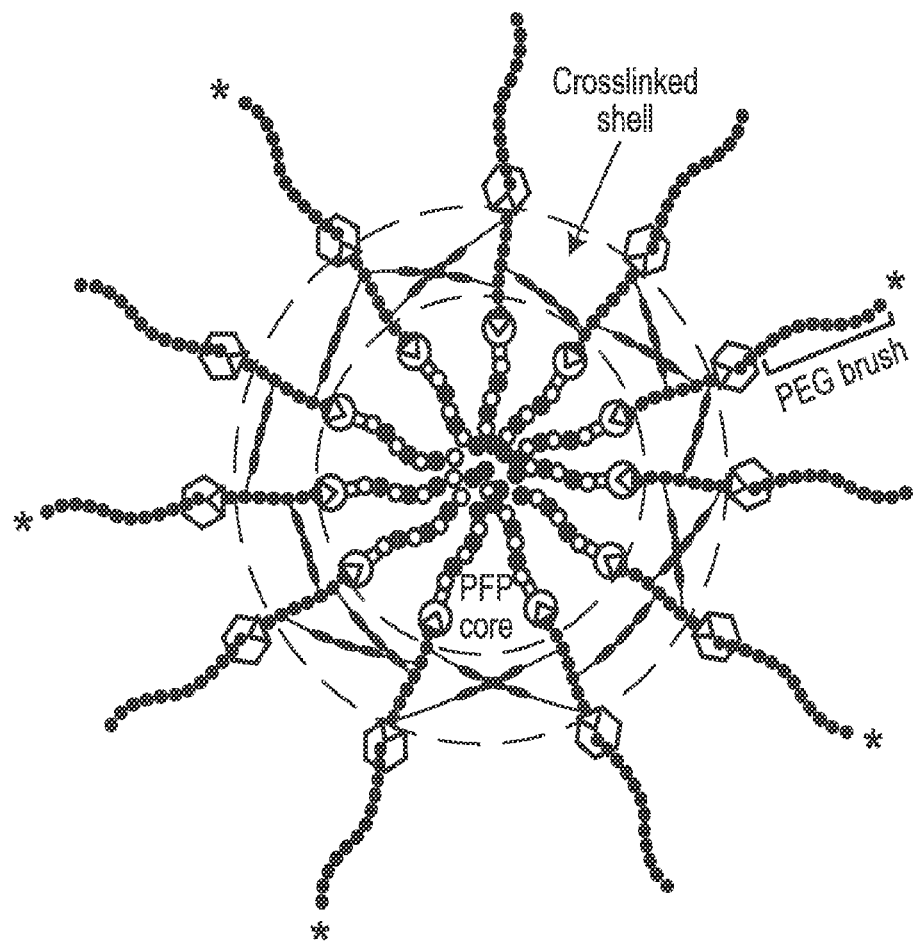
FIG. 1A is a schematic of a targeted nano-bubble showing the PFP core (US contrast agent) encapsulated by a flexible polymer shell that displays a brush of PEG chains, which present a "tunable" number of anti-PSMA antibody.

We designed and subsequently developed targeted nanobubbles for use in combination with ultrasound (US) for detection, imaging, and selective ablation of recurrent prostate cancer cells. We designed the nanobubbles to encapsulate perfluoropentane (PFP), an ultrasound (US) contrast agent with a boiling point of 29.2° C., using a new tri-block copolymer composed of a hydrophilic PEG block, a central functionalized block, and a PFP-miscible block to form stable nano-micelles (FIG. 1A). Functional groups displayed on the central block of the tri-block copolymer were designed to be cross-linked to "stitch" the polymer chains together forming a flexible polymer shell that displays a "brush" of hydrophilic PEG chains, which were designed to present an array of targeting ligands against prostate-specific membrane antigen (PSMA). We designed the nanobubbles so that the PFP in the core of these micelles transition from the liquid to the gas phase when injected into the systemic blood circulation due to higher body temperature (37° C.) compared to PFP boiling point (29° C.) and micelle perturbation by therapeutic US forms a gaseous PFP core surrounded by a flexible polymer shell (FIG. 1A). The difference in acoustic impedance between the gas core of these nano-bubbles and the surrounding medium, coupled with the oscillation of the nano-bubbles, were to increase their acoustic scattering and echogenicity on ultrasound imaging. We designed nanobubbles to have a smaller diameter from those of commercial micro-bubbles that have an average diameter of 1-6 μm. Our targeted nano-bubbles were designed to have a diameter <500 nm, so that they are able to diffuse from the systemic circulation into tumor's interstitial tissue and selectively bind to prostate cancer cells allowing their detection on US imaging. Additionally, the nanobubbles were designed such that selective binding of targeted nano-bubbles to PSMA expressed on the surface of prostate cancer cells would cause the aggregation of multiple nano-bubbles on cancer cell surface, which would further increase their echogenicity on US images.

Design of Amphiphilic, Self-Assembling, Copolymers for Formulation of Nano-Bubble Contrast Agents The main challenge in formulating nano-bubble contrast agents is their high surface tension, which results in their quick dissolution in the blood stream.[65,66] Using stiff polymer[67-74] and lipid[76-79] shells proved to lower the surface tension and minimize the dissolution of the nano-bubbles but it also interfered with bubble's oscillation and reduced their contrast on US imaging.[31] Therefore, successful development of nano-bubble contrast agents requires the design of a new shell that can stabilize the gaseous PFP core and reduce bubble's surface tension while maintaining nano-bubble's oscillation in response to therapeutic US.

Perfluoropentane (PFP) is an extremely hydrophobic, non-toxic, and non-carcinogenic fluoroalkane with a boiling point (29.2° C.) between room (20-25° C.) and body temperature (37° C.), which allows its injection into the body in the form of liquid droplets dispersed in an aqueous medium that convert to bubbles in the systemic circulation. This interesting behavior motivated the use of PFP as an US contrast agent and as a carrier for gene and drug delivery.[80-82] However, PFP has a very high interfacial tension against water because of its hydrophobic nature, which hinders its dispersion in aqueous media.[83] Ionic, non-ionic, and polymeric surfactants have been used to reduce PFP interfacial tension and improve its dispersion in water by forming core-shell micelles that entrap PFP in their cores.[29,82-85] However, these micelles exhibit broad size distribution with an average size >1 μm, which hinders their diffusion from the systemic circulation into the interstitial tissue and consequently limit their clinical utility to US imaging of the vascular compartment.[86-89]

Figure 1B:
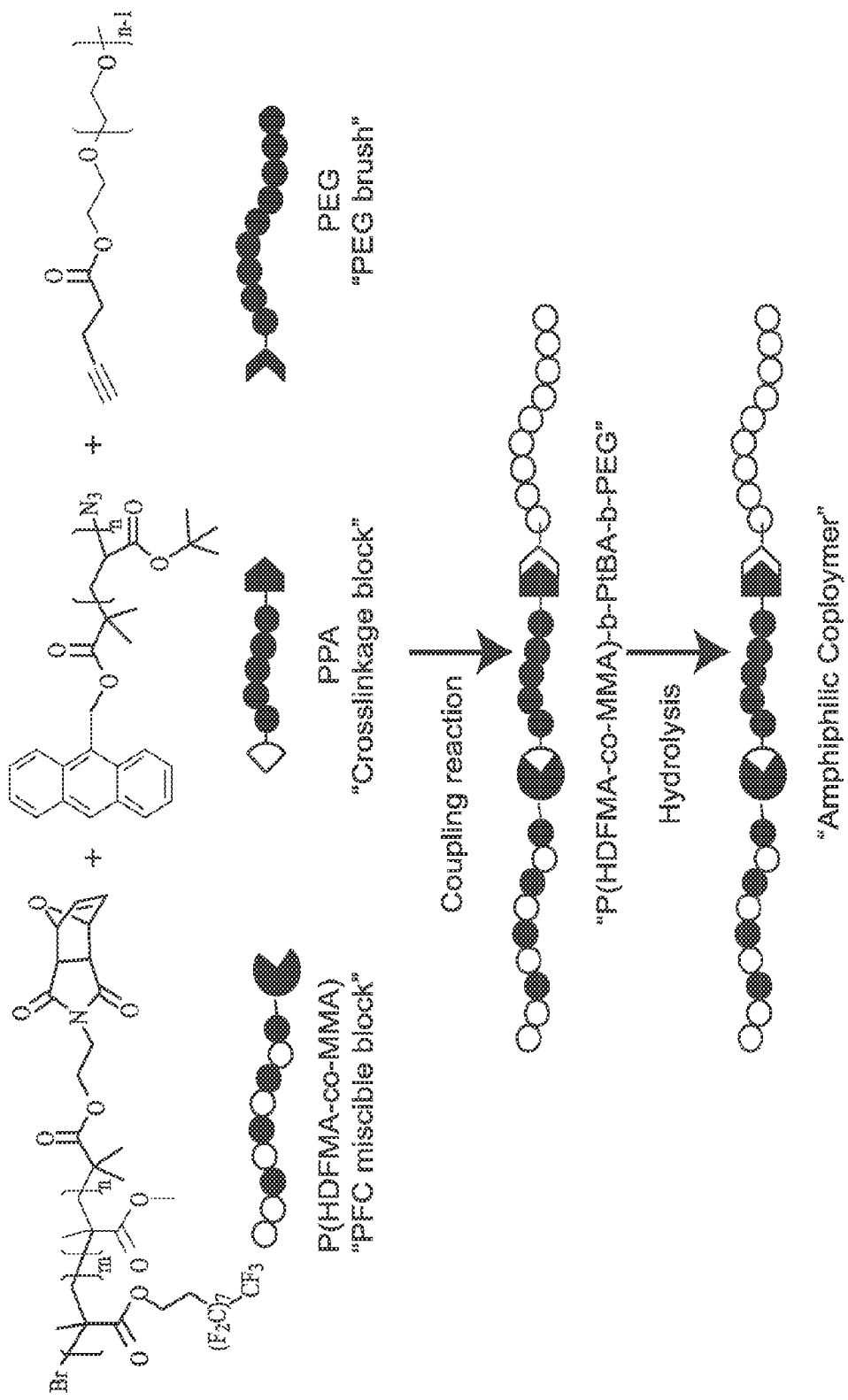
FIG. 1B is a drawing depicting the structure and synthesis of amphiphilic tri-block copolymers.

To overcome these limitations, we have designed and synthesized a new amphiphilic tri-block copolymer that proved to self-assemble around a PFP core forming stable nano-micelles. Briefly, we synthesized an ABC tri-block copolymer that is composed of a hydrophilic polyethylene glycol (PEG) block, a central polyacrylic acid (PAA) block, and a hydrophobic block of methyl methacrylate (MMA) and hexadecafluorodecyl methacrylate (HDFMA) random copolymer (FIG. 1B).

Figure 1C:
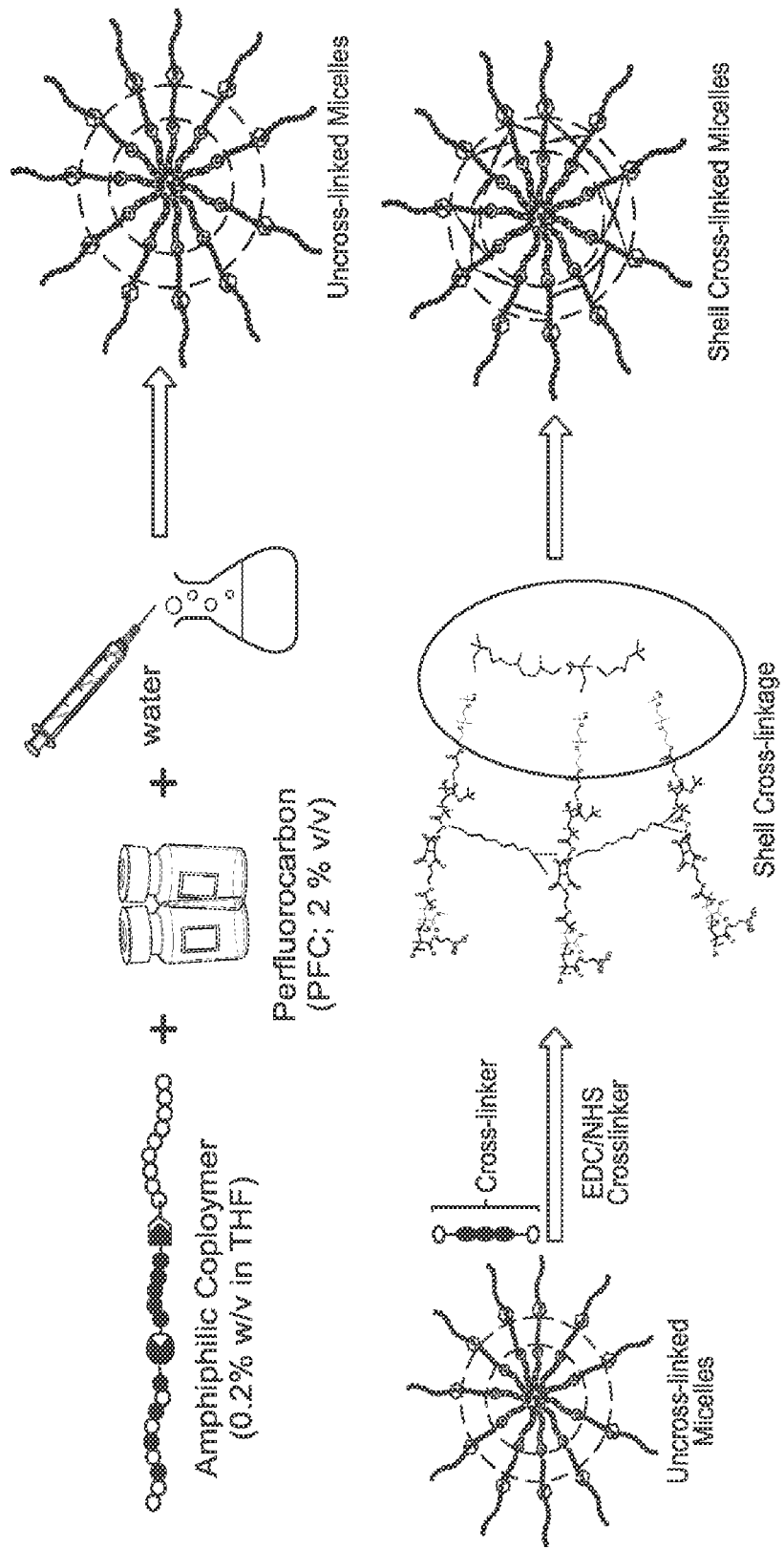
FIG. 1C is a drawing depicting the formulation of uncrosslinked and cross-linked PFP-loaded nano-micelles.

We hypothesized that dispersing PFP in an aqueous medium (e.g. PBS) in presence of this tri-block copolymer will allow the hydrophobic block, P(MMA-co-HDFMA), to interact with the dispersed hydrophobic PFP droplets and trigger polymer's assembly into uniform nano-sized micelles (FIG. 1C). We envisioned that uncross-linked micelles can be further stabilized by cross-linking the carboxylic acid groups present in the central PAA block using 2,2'-(ethylenedioxy)-bis(ethylamine) as a cross-linker via established NHS/EDC coupling chemistry.[90-92] Further, we chose PEG as the hydrophilic block based on its unique properties including: i) resistance to the adsorption of plasma proteins,[93] ii) conferring "stealth" properties to the micelles allowing them to evade recognition and uptake by the reticular endothelial system (lungs, liver, and spleen),[94] iii) increasing particle's accumulation in tumor tissue via passive targeting strategies,[95,96] iv) allowing easy covalent coupling of targeting ligands (e.g. J591 antibody) to develop targeted nano-carriers,[97,98] and v) its established biocompatibility.[99,100]

Figure 1D:
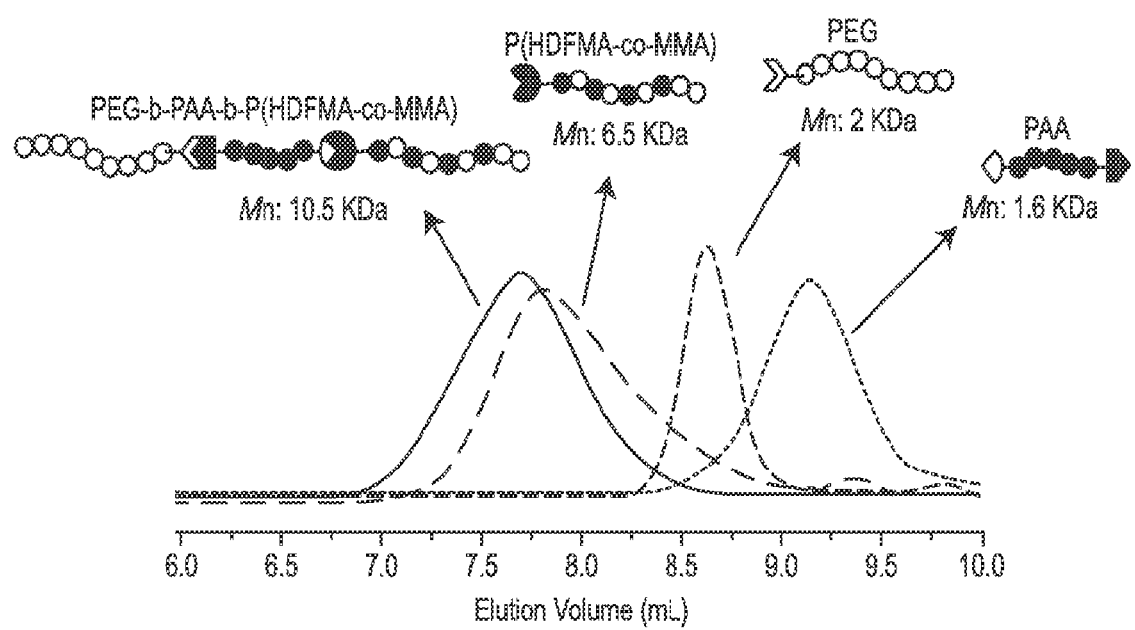
FIG. 1D is a graph of GPC traces of individual blocks and final tri-block copolymer.
Figure 1E:
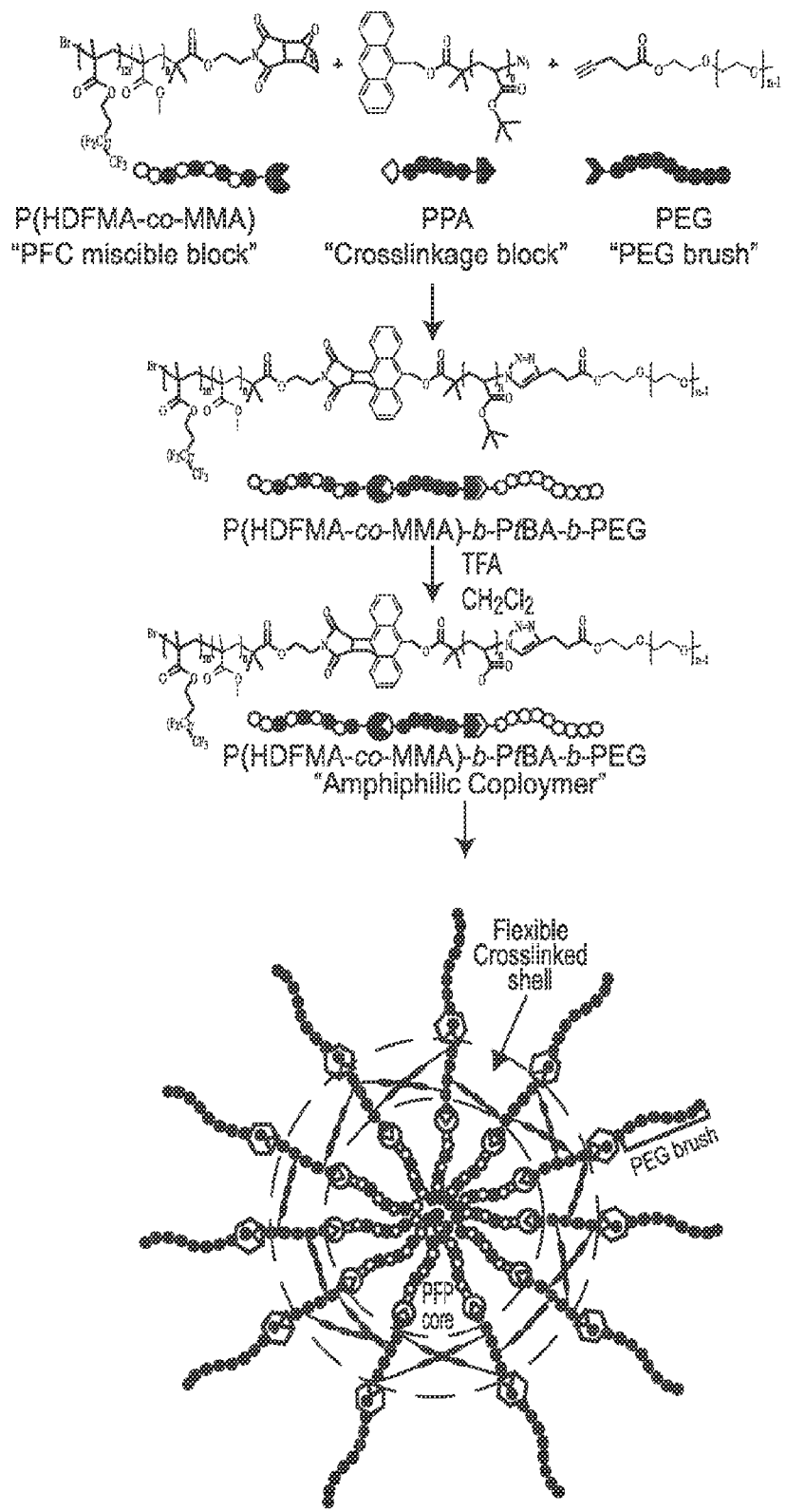
FIG. 1E is a schematic representation of PFC encapsulated nano-droplet

Synthesis of Amphiphilic Tri-block Copolymer:

Formulation of uniform nano-bubbles with narrow size distribution depends primarily on the ability to synthesize well-defined amphiphilic polymers with narrow molecular weight distribution. Consequently, we utilized controlled polymerization techniques particularly atom transfer radical polymerization (ATRP) to synthesize the PAA and P(MMA-co-HDFMA) blocks with average molecular weights of 1.6 KDa and 6.5 KDa, respectively. We engineered the terminal functional groups of the PEG, PAA, and P(MMA-co-HDFMA) blocks to allow their sequential coupling through Diels-Alder[101-103] and azid-alkyne[104-106] "click" reactions following established procedures (FIG. 1B). Our synthesis strategy is to utilize an anthracene-functionalized initiator to polymerize t-butylacrylate monomers to obtain the PAA block with a bromine group on one end of the polymer chain and the anthracene group (coupling partner in Diels-Alder reaction) on the other. Subsequently, we transformed the terminal bromine group to azide to allow coupling through azide-alkyne cycloaddition reaction. We polymerized MMA and HDFMA monomers to obtain the hydrophobic P(MMA-co-HDFMA) block with a protected maleimide group (the second partner in Diels-Alder coupling reaction) on one end of the polymer chain. We functionalized commercial PEG (2 KDa) with a terminal alkyne group to allow coupling to the central PAA block via conventional azid-alkyne addition reaction. The asymmetric functionalization of these blocks allowed their controlled coupling in a single reaction to yield a well-defined amphiphilic tri-block copolymer (FIG. 1B). Gel permeation chromatography (GPC) results confirm the synthesis of well-defined blocks and their coupling into an amphiphilic tri-block $(PEG)_{45}$-b-$(PAA)_{10}$-b-P(MMA-co-HDFMA)$_{28}$ copolymer (10.2 KDa) with narrow molecular weight distribution (FIG. 1D).

We hypothesized that increasing the size of the nano-bubbles between 100-500 nm will increase the volume of the encapsulated PFP and increase their echogenicity on US imaging. On the contrary, increasing the shell cross-linkage density will increase its stiffness and reduce nano-bubbles oscillation in response to US, which will reduce echogenicity. Our goal was to systematically investigate the effect of molecular weight and the hydrophilic/hydrophobic balance in $(PEG)_x$-b-$(PAA)_y$-b-P(MMA-co-HDFMA)$_z$ copolymers on the size, stability, and echogenicity of the formulated nano-bubbles to develop a robust strategy to "tune" their imaging and therapeutic activity.

Formulation of Nano-Bubbles with Different Size (100-500 nm)

ABC-3 of Table 1, $(PEG)_{45}$-b-$(PAA)_{10}$-b-P(MMA-co-HDFMA)$_{28}$, copolymer has an average molecular weight of 10.2 KDa and the ratio of hydrophobic MMA and HDFMA monomers to hydrophilic ethylene glycol (EG) and acrylic acid (AA) monomers is ~1/2. It successfully encapsulates PFP (2% v/v) into shell cross-linked nano-bubbles with an average size of 259±18 nm at 37° C. Using the same synthetic strategies described earlier (FIG. 1B), we will synthesize a series of copolymers (Table 1) with different molecular weights (~6.5, 8.5, 10, 13, 15, 16, and 19 KDa) and different ratios of hydrophobic/hydrophilic monomers (1/2, 1/2.5, 1/3, 1/4.5) and test their ability to encapsulate different amounts of PFP (0.5%-5% v/v) using the formulation methods summarized earlier (FIG. 1C). We will vary shell cross-linkage density of the nano-micelles by varying the molar ratio of the cross-linker to the carboxylic acid groups of the PAA block (1/1, 0.5/1, 0.25/1). We will measure the size and zeta potential of the nano-micelles using 90Plus particle size analyzer with ZetaPALS capability (Brookhaven Instruments Corporation).[109] We expect that polymers with higher content of hydrophobic monomers (e.g. ABC-4) will form smaller and more compact micelles compared to those with higher content of hydrophilic monomers (e.g. ABC-5). We also expect the polymers with higher molecular weight (e.g. ABC-7) to form bigger micelles compared to shorter polymers with similar compositions (e.g. ABC-2).

(i.e., the two ends of the PEG chain can attach to different chemical groups), and biocompatible. Further, PEG also is soluble in some organic systems.

Figure 2A:
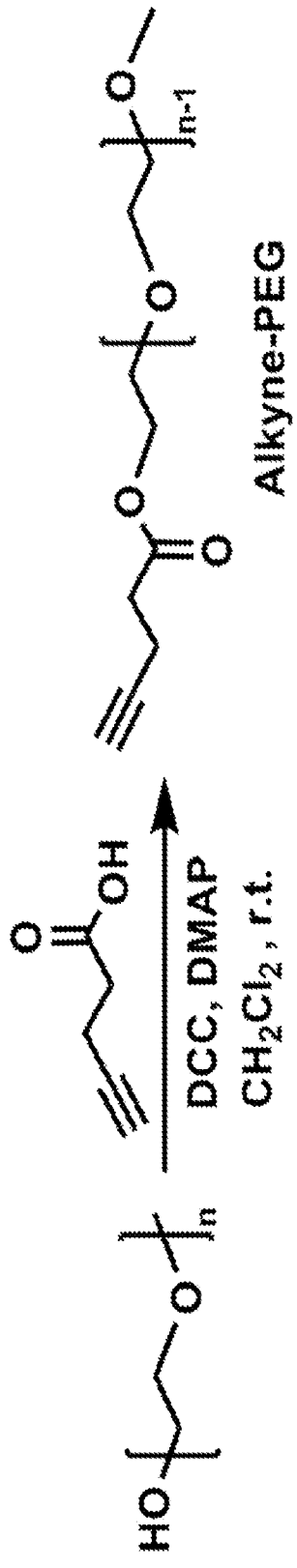
FIGS. 2A to 2G are a collection of schemes for synthesizing an amphiphilic triblock copolymer and the use thereof in preparing cross-linked micelles.
Figure 2B:
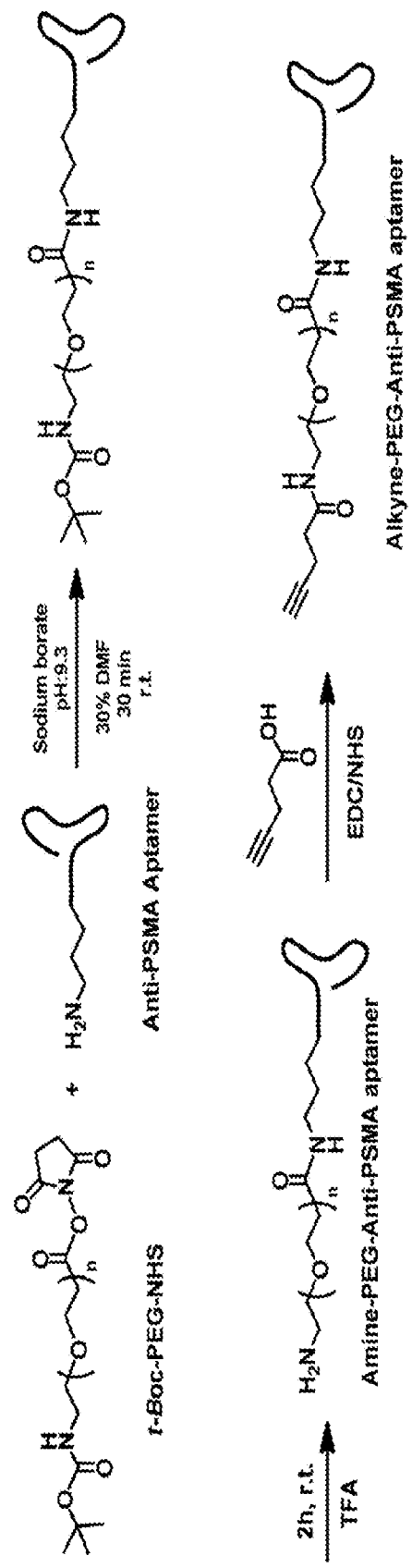
Figure 2C:
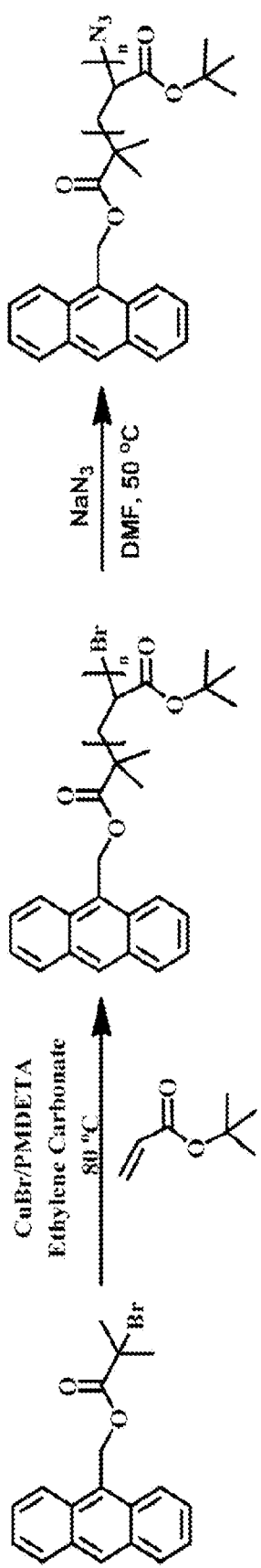

Synthesis of Cross-Linkable Block (PtBA):

Poly(t-butyl acrylate) (PtBA) was used as a precursor of crosslinking block B. Block B was synthesized using Atom Transfer Radical Polymerization (ATRP) with an anthracene functional initiator that included a bromine functionality on one end. The bromine functionality was converted to an azide group for participation in a click reaction (Scheme 3; FIG. 2C). The tert-butyl groups of PtBA were eventually hydrolyzed (after formation of the A-B-C triblock polymer) to result in poly acrylic acid (PAA). Block B includes 10 to 25 repeating units (e.g., 10, 15, 20, or 25 units), and a typical ABC block copolymer useful for the formation of a cross-linked shell includes 10 acrylic acid units.

Block B can also consist of poly(hydroxyl ethyl acrylate) (PHEA). Before formation of block B, however, the hydroxyl group of the monomer must be protected (e.g., with a tert-butyldimethylsilyl group) to control polymerization and improve solubility. After a polymer is obtained with the desired number of repeating units (i.e., 10, 15, 20, 25, or 30 units), and a one-pot click reaction is run to obtain the ABC block copolymer, the protecting group can be removed. If desired, the deprotected hydroxyl group can be functionalized to perform different types of cross-linking reactions, such as the photopolymerization of acrylate groups, or the photodimerization of cinnamate groups.

TABLE 1

| Polymer Name | $M_n$ of PEG block (# of EG units) | $M_n$ of PAA block (# of AA units) | $M_n$ of P(MMA-co-DFMA) block (# of units) | $M_{n\text{-}phobic}/M_{n\text{-}philic}$ | #$_{phobic}$/#$_{philic}$ units | $M_n$ of ABC copolymer (g/mol) |
|---|---|---|---|---|---|---|
| ABC-1 | 2,000 (45) | 1,650 (10) | 3,130 (12) | 1/1.1 | 1/4.5 | 6,750 |
| ABC-2 | 2,000 (45) | 1,650 (10) | 4,700 (21) | 1/1.3 | 1/2.6 | 8,350 |
| ABC-3 | 2,000 (45) | 1,650 (10) | 6,630 (28) | 1/1.8 | 1/1.9 | 10,230 |
| ABC-4 | 2,000 (45) | 1,650 (10) | 12,500 (58) | 1/1 | 3.4/1 | 16,150 |
| ABC-5 | 5,000 (113) | 1,650 (10) | 3,130 (12) | 1/4.7 | 1/10.2 | 9,770 |
| ABC-6 | 5,000 (113) | 1,650 (10) | 6,630 (28) | 1/1 | 1/4.4 | 13,280 |
| ABC-7 | 5,000 (113) | 1,650 (10) | 8,650 (40) | 1.3/1 | 1/3 | 15,300 |
| ABC-8 | 5,000 (113) | 1,650 (10) | 12,500 (58) | 1/2.1 | 1/1.9 | 19,150 |

Figure 2D:
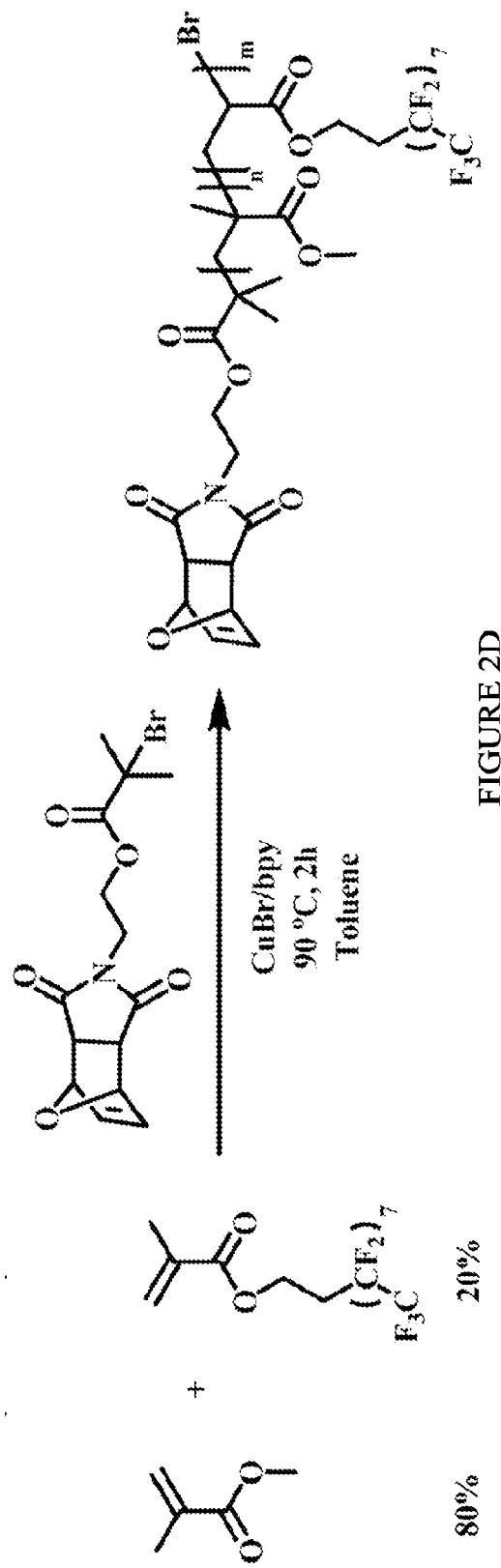
Figure 2E:
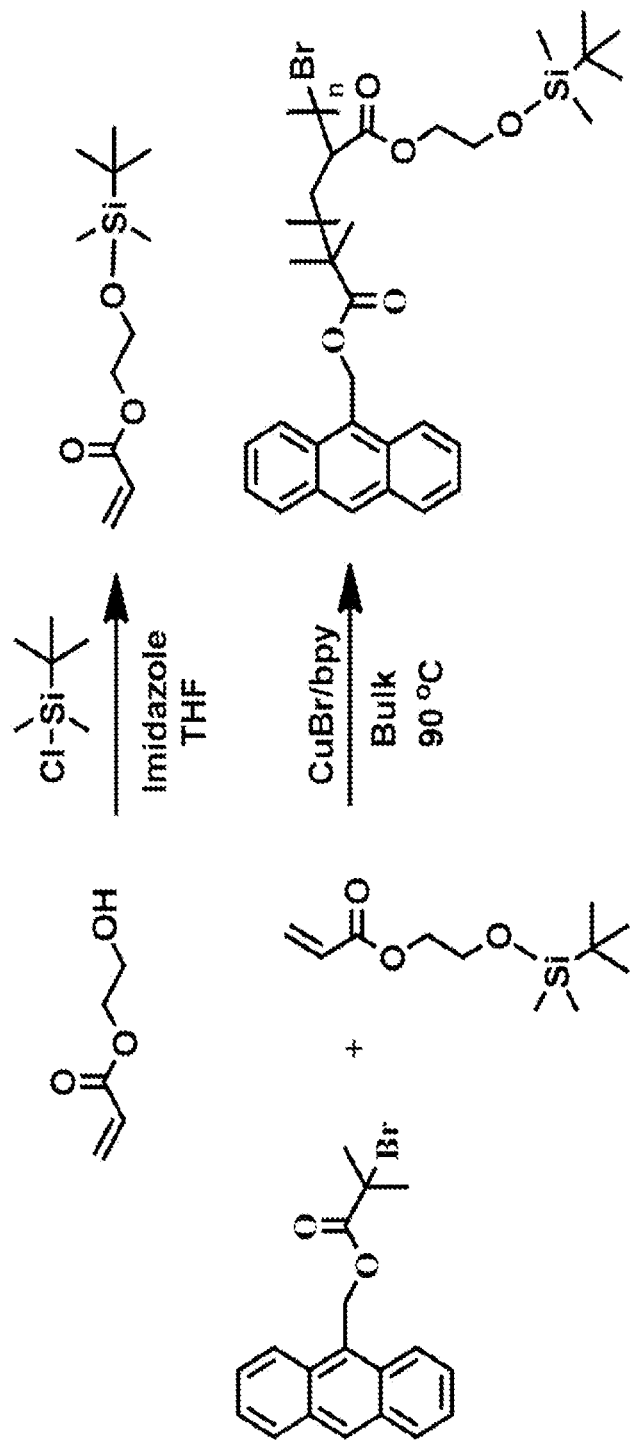

Preparation of Block A:

Commercially available PEG (e.g, 1 kDa, 2 kDa, 3.4 kDa, and 5 kDa PEG) was used for functionalization. Alkyne-PEG-aptamers were synthesized using commercially available tert-Boc-PEG-NHS and 2 kDa, 3.4 kDa, or 5 kDa PEG. The preparation of mono- and di-functional PEG aptamers is shown in Schemes 1 and 2 (FIGS. 2A and 2B), respectively. These aptamers are the targeted portion of the final amphiphillic triblock polymer. A PSMA-specific antibody, J591, was attached to the tip of each PEG to act as a targeting ligand that binds to a prostate cancer-specific antigen. PEG was chosen as block A because it is water-soluble, commercially available in varying molecular weights, bi-functional Synthesis of Hydrophobic Block P(MMA-Co-HDFMA):

Block C is hydrophobic and includes methyl methacrylate (MMA) and 1H,1H,2H,2H-heptadecafluorodecyl methacrylate (HDFMA). HDFMA is fluorinated monomer, which interacts with PFC. The purpose producing a copolymer of MMA and HDFMA for block C instead of a homopolymer composed of HDFMA is to improve solubility of block C. HDFMA and MMA were copolymerized via ATRP using a maleimide functional initiator (Scheme 4; FIG. 2D). The mole percentage of HDFMA was 20%, but may vary as 5, 10, 15, 20, or 25%. The P(HDFMA-co-MMA) hydrophobic blocks that were synthesized are summarized in Table 2.

TABLE 2

| Code | Time (min) | Conv.[b] (%) | Ligand | # of HDFMA[c] | # of MMA[c] | $M_{n theo}$[d] (g/mol) | $M_{n NMR}$[c] (g/mol) | $M_{n GPC}$[e] (g/mol) | $M_w/M_n$[e] |
|---|---|---|---|---|---|---|---|---|---|
| YYD38 | 120 | 50 | bpy | 15 | 43 | 7780 | 12500 | 10980 | 1.26 |
| YYD55 | 60 | 38 | PMDETA | 9.9 | 30.5 | 5730 | 8650 | 9150 | 1.22 |
| YYD342 | 120 | 30 | n-Pentyl | 9 | 25 | 4920 | 7290 | 7470 | 1.09 |
| YYD349 | 108 | 48 | n-Pentyl | | | | 7660 | 7825 | 1.12 |

TABLE 2-continued

| Code | Time (min) | Conv.[b] (%) | Ligand | # of HDFMA[c] | # of MMA[c] | $M_{ntheo}$[d] (g/mol) | $M_{nNMR}$[c] (g/mol) | $M_{nGPC}$[e] (g/mol) | $M_w/M_n$[e] |
|---|---|---|---|---|---|---|---|---|---|
| YYD348 | 130 | 42 | n-Pentyl |  |  | 6750 |  | 8300 | 1.14 |
| YYD70 | 120 | 31 | n-Pentyl | 8 | 20 | 5070 | 6630 | 5500 | 1.15 |
| YYD351 | 90 | 35 | n-Pentyl | 9.5 | 30 | 5685 | 8050 | 6250 | 1.14 |
| YYD352 | 84 | 21 | n-Pentyl | 6.6 | 18 | 3550 | 5340 | 5200 | 1.10 |
| YYD66 | 60 | 18.8 | n-Pentyl | 6 | 15 | 2925 | 4700 | 4550 | 1.17 |
| YYD350 | 75 | 17 | n-Pentyl | 6.4 | 16 | 2945 | 5000 | 4500 | 1.12 |
| YYD344 | 90 | 8 | n-Pentyl | 3.5 | 8 | 1775 | 2663 | 3860 | 1.09 |
| YYD347 | 105 | 10 | n-Pentyl | 4 | 10 | 1880 | 3130 | 3500 | 1.15 |

[a][I]$_0$/[CuBr]$_0$/[L]$_0$ = 1/1/2 for bpy and n-Pentyl, [I]$_0$/[CuBr]$_0$/[L]$_0$ = 1/1/1 for PMDETA, in Toluene. MMA/HDFMA: 80/20 in feed.
[b]Determined by gravimetrically.
[c]Calculated from $^1$H NMR spectra.
[d]Calculated by using $M_{n\,theo}$ = ([M]$_0$/[I]$_0$ × (%) Conv. × 100 + $M_{wI}$)
[e]Determined from GPC by using PMMA standards, THF as an eluent at 35° C.

For block C, the HDFMA fluorinated monomer can be replaced with another fluorinated monomer that contains less fluorine (e.g., 2,2,2-Trifluoro ethyl methacrylate, TFEMA). When HDFMA is replaced with TFEMA, the mole percentage of TFEMA would be increased in the resulting copolymer.

Block copolymerization (instead of random copolymerization) of MMA and HDFMA was unsuccessful because of the poor solubility of HDFMA.

Figure 2F:
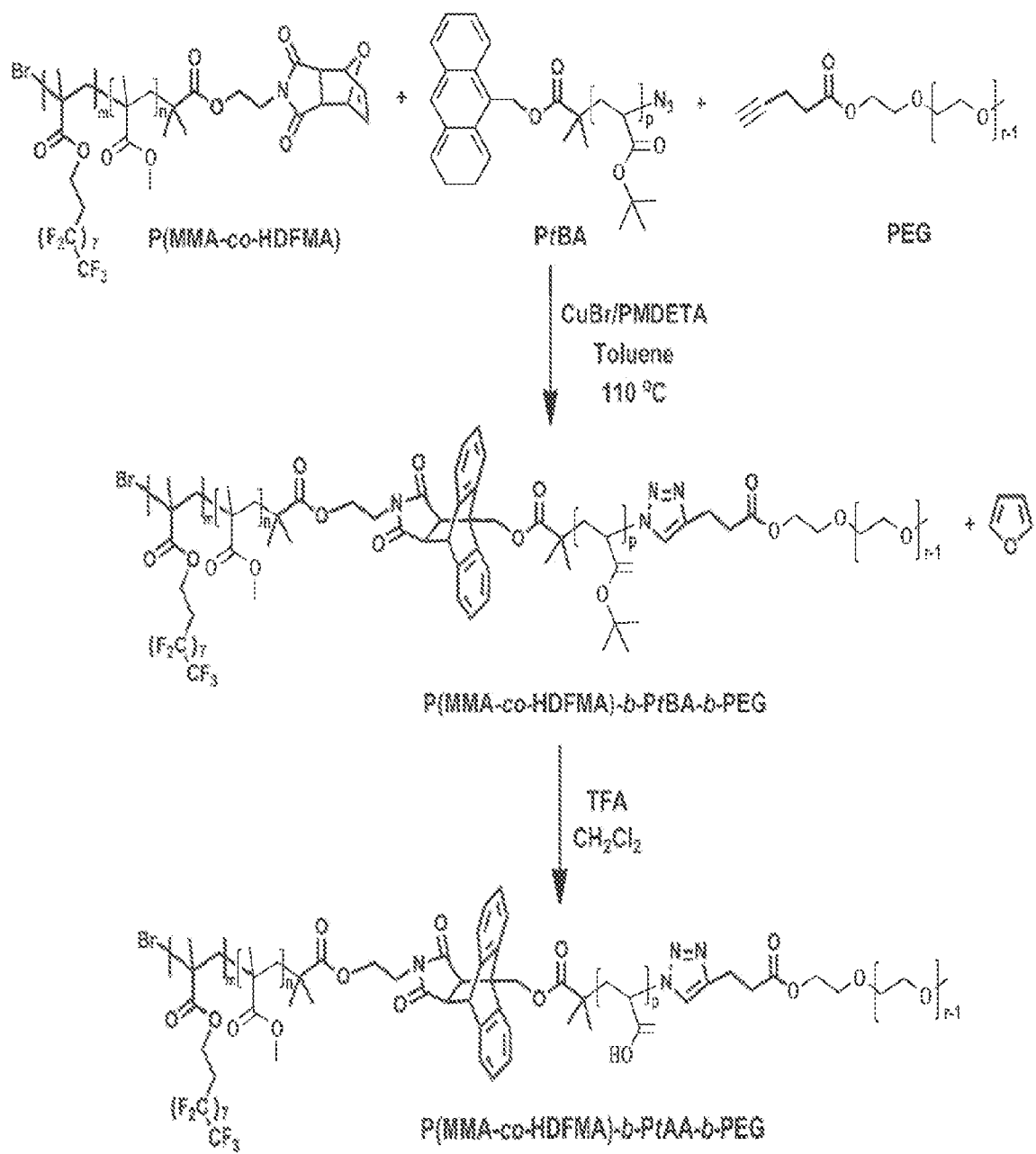

Blocks A, B, and C were reacted to form the ABC triblock copolymer via a one-pot diels-Alder and azide-alkyne click reaction (Scheme 6; FIG. 2F). ABC triblock copolymers having different compositions were synthesized, such as PEG$_{45}$-b-PAA$_{10}$-b-P(MMA$_{43}$-co-HDFMA$_{15}$), PEG$_{45}$-b-PAA$_{10}$-b-P(MMA$_{20}$-co-HDFMA$_{8}$), PEG$_{113}$-b-PAA$_{10}$-b-P(MMA$_{30}$-co-HDFMA$_{10}$) (Table 3).

TABLE 3

| Polymer code | $M_n$ of Hydrophobic P(MMA-co-HDFMA) block (# of units) (g/mol) | $M_n$ of crosslinkable PAA block (# of units) (g/mol) | $M_n$ of Hydrophilic PEG block (# of units) (g/mol) | $M_{nHP}/M_{nHF}$ | # of HP/# of HF units | $M_n$ of ABC block copolymer (g/mol) |
|---|---|---|---|---|---|---|
| YYD125* | 12500 (58) | 1650 (10) | 2000 (45) | 3.42 | 1.05 | 16150 |
| YYD218 | 6630 (28) | 1650 (10) | 2000 (45) | 1.81 | 0.50 | 10280 |
| YYD280 | 8650 (40) | 1650 (10) | 5000 (113) | 1.30 | 0.32 | 15600 |

*Polymer crushed down during micellization process.

Figure 2G:
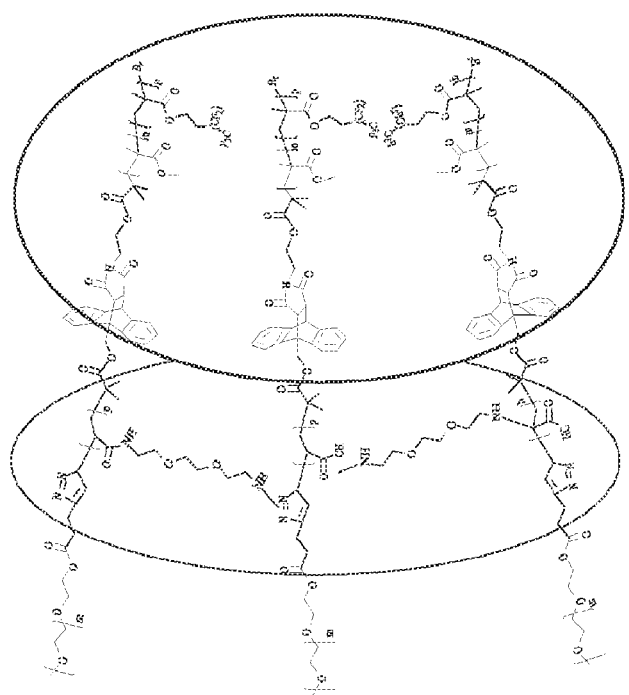
Figure 2G:
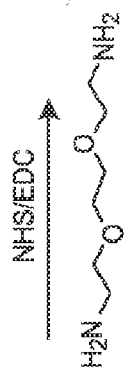
Figure 2G:
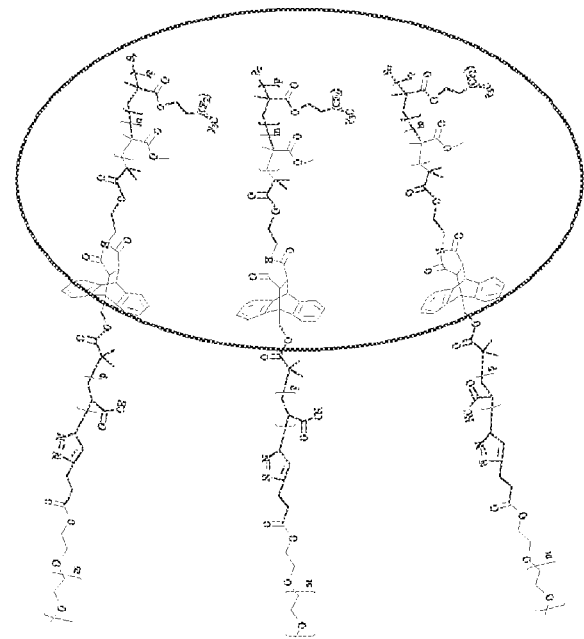

Formulation of Nano-Bubble Contrast Agents:

The ability of (PEG)$_{45}$-b-(PAA)$_{10}$-b-P(MMA-co-HDFMA)$_{28}$ copolymer to self-assemble into nano-sized micelles was investigated as follows. A solution of the polymer in tetrahydrofuran (0.2% w/v) was prepared. This solution was combined with a solution of PFP (2% v/v), with stirring and at a temperature 0° C. (FIG. 1C). Water was slowly added to this solution mixture to trigger micelle formation. The resulting solution was transferred to a dialysis bag (MWCO of 1 KDa), and was subsequently dialyzed against an ice cold PBS solution to remove organic solvent. After 8 hours of dialysis, a milky solution of uncross-linked micelles loaded with PFP was obtained. Half of the micelle solution was used to prepare shell cross-linked micelles by reacting the carboxylic acid groups of block B's PAA with 2,2'-(ethylenedioxy)-bis(ethylamine) cross-linker via NHS/EDC coupling chemistry (FIGS. 1C and 2G; Scheme 7).[90-92] The size and zeta potential of cross-linked and uncross-linked micelles at room temperature (22° C.) and body temperature (37° C.) were measured using a 90Plus particle size analyzer with ZetaPALS capability (Brookhaven Instruments Corporation, Holtsville, N.Y.).

Figure 3A:
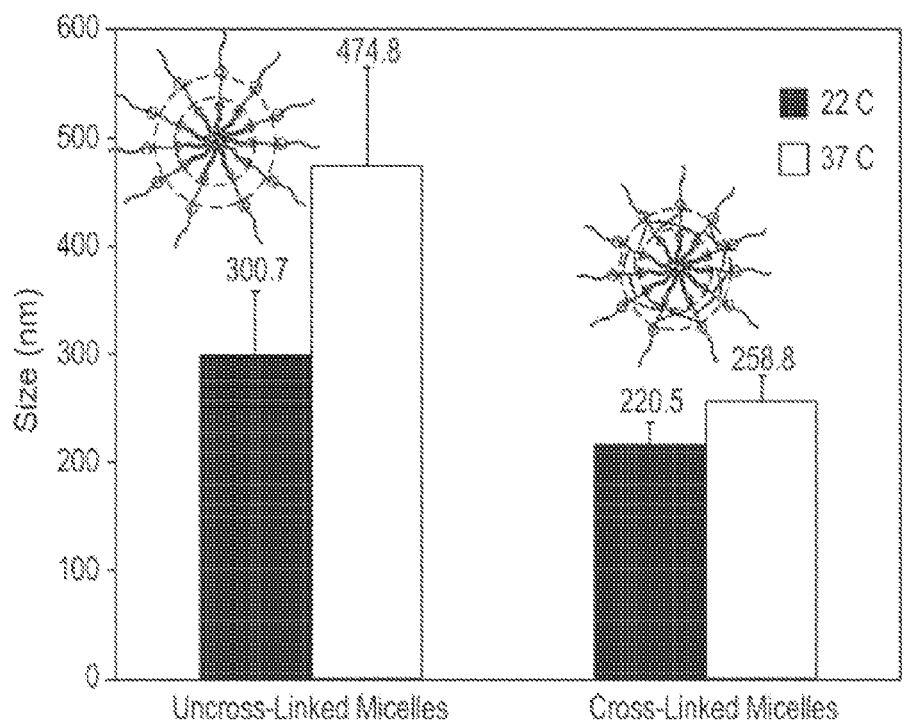
FIGS. 3A to 3C represent a collection of graphs demonstrating the size of micelles before and after cross-linked reaction at 22 and 37 C for three different experiments. XL=cross-linked; NXL=not cross-linked.

The results show that (PEG)$_{45}$-b-(PAA)$_{10}$-b-P(MMA-co-HDFMA)$_{28}$ copolymer assembles into nano-micelles with an average diameter of 300±62 nm at room temperature. The average diameter of these nano-micells expands to 475±91 nm upon heating the micelle solution to 37° C. The heat-responsive expansion is probably due to transition of the encapsulated PFP from the liquid phase to the gas phase, which results in the formation of nano-bubbles. At room temperature, the cross-linked micelles showed a decrease in their average diameters to 220±15 nm, and then underwent a modest diameter increase, to 259±18 nm, upon heating at 37° C. This result is expected due to the formation of a chemically "stitched" polymer shell that slows down the diffusion of the PFP gas out of the micelle core (FIG. 3A). These results collectively show successful formulation of nano-bubbles.

Our results show that (PEG)$_{45}$-b-(PAA)$_{10}$-b-P(MMA-co-HDFMA)$_{28}$ copolymer assembles into nano-micelles with an average diameter of 300±62 nm at room temperature, which expands to 475±91 nm upon heating the micelle solution to 37° C. probably due to transition of the encapsulated PFP from the liquid to the gas phase forming nano-bubbles. Cross-linked micelles showed a decrease in their average size to 220±15 nm at room temperature with a modest size increase to 259±18 nm upon heating the micelle solution to 37° C., which is expected due to the formation of a chemically "stitched" polymer shell that slows down the diffusion of the PFP gas out of the micelle core (FIG. 3A). These results collectively show successful formulation of nano-bubbles.

Table 4 shows the importance of the polymer and the PFC used for micellization. When a buffer solution was used instead of water, micelles were not obtained.

TABLE 4

| Code | % of Polymer | Amount of Polymer | THF (mL) | % of PFC | PFC (μL) | Final Volume (mL) | Final Polymer Conc. (M) | # of Particle in mL | Micelles Size (nm) |
|---|---|---|---|---|---|---|---|---|---|
| YYD241 | 0.1% | 1.2 mg | $1.34^b$ | 1% | 26 | 4 | $2.85 \times 10^{-5}$ | — | 145 ± 71 |
| YYD255 | 0.1% | 1.2 mg | $1.34^b$ | 1% | 26 | 4.2 | $2.66 \times 10^{-5}$ | NXL: $1.51 \times 10^{11}$ | 191 ± 176 |
|  |  |  |  |  |  |  |  | XL: $3.25 \times 10^{11}$ | 99 ± 133 |
| YYD276 | 0.1% | 3 mg | $3.35^b$ | 1% | 67 | 12.5 | $2.85 \times 10^{-5}$ | — | 296 ± 186 |
|  |  |  |  |  |  |  |  | XL: $7.92 \times 10^{12}$ | 375 ± 97 |
| YYD286 | 0.2% | 2.4 mg | $1.34^b$ | 2% | 52 | 4.5 | $5.07 \times 10^{-5}$ | — | 258 ± 162 |
|  |  |  |  |  |  |  |  |  | 111 ± 72 |
| $\text{YYD285}^a$ | 0.2% | 2.4 mg | $1.34^b$ | 4% | 130 | 4.5 | $5.07 \times 10^{-5}$ | — | — |
| YYD363 | 0.2% | 2.4 mg | $1.34^b$ | 1% | 26 | 5 | $4.69 \times 10^{-5}$ | NXL: $5.28 \times 10^{12}$ | 163 ± 180 |
|  |  |  |  |  |  |  |  | XL: $4.58 \times 10^{12}$ | 94 ± 36 |
| YYD360 | 0.2% | 2.4 mg | $1.34^c$ | 2% | 52 | — | — | — | — |
| YYD361 | 0.2% | 2.4 mg | $1.34^c$ | 1% | 26 | — | — | — | — |
| YYd362 | 0.1% | 1.2 mg | $1.34^c$ | 1% | 26 | — | — | — | — |

[a] Phase separation was observed between THF and PFP.
[b] Same amount water was added to system slowly.
[c] 1.34 mL MES buffer solution was added slowly instead of water, each cases polymer crashed down.

Figure 3B:
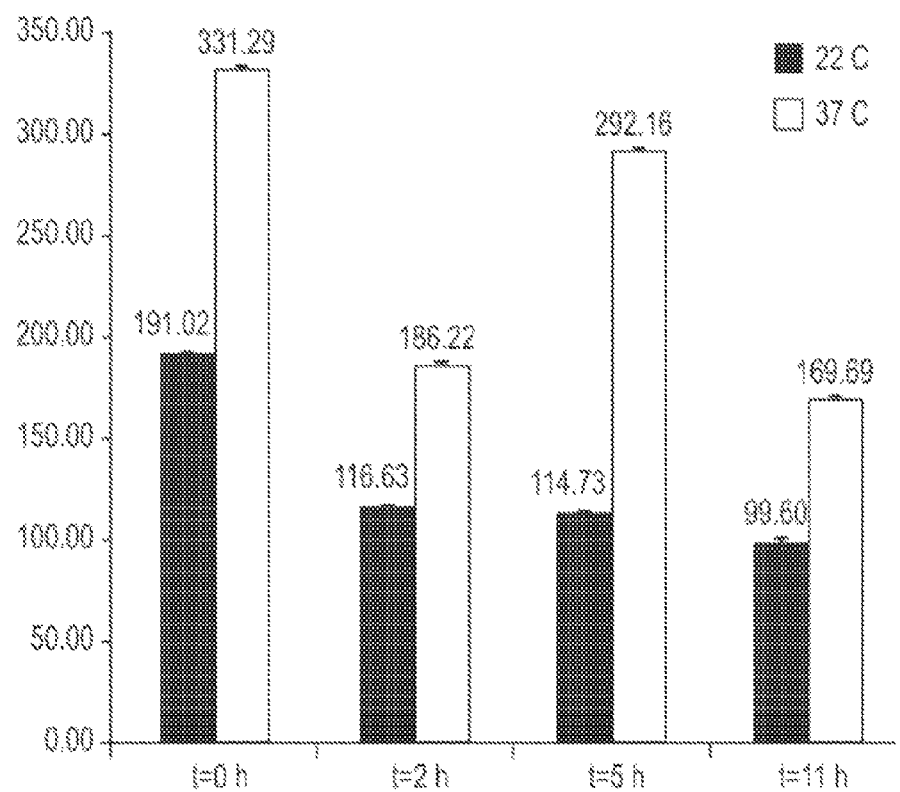
Figure 3C:
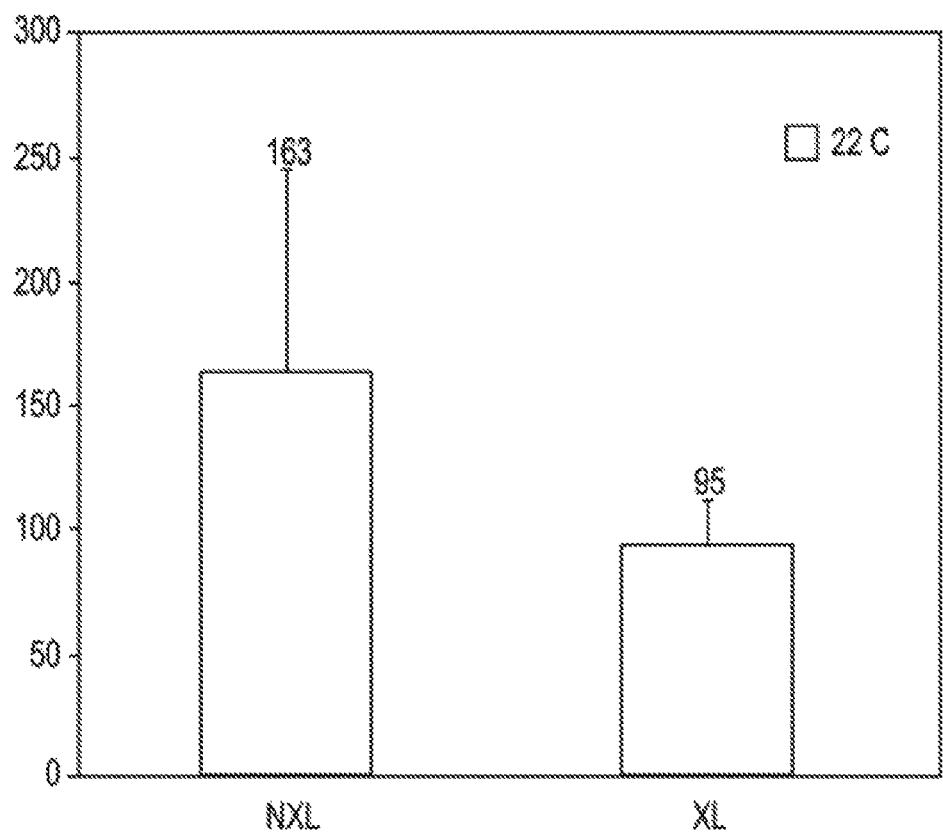

After the cross-linking reaction, the size of the micelles was monitored by dynamic light scattering (DLS), and data is shown in FIG. 3A to 3C. The cross-linking reaction showed a reduction in micelle size.

Example 2

Ultrasound Imaging of Nanobubbles

Nano-sized micelles prepared as described in Table 4, were used for imaging and therapy experiments. We prepared a vessel gel phantom by embedding a hollow polyethylene (PE) tube in a 10% w/v gelatin mixed with 0.5% w/w graphite (a sound scatterer) to prepare a gel that displays a similar speckle to soft tissue on ultrasound imaging. We filled the hollow PE tube in the center of the phantom with 4 mL of the nano-bubbles solution (size=375±97 nm; concentration=$7.92 \times 10^{12}$ nano-bubbles/mL) to evaluate the enhancement in echogenicity caused by the nano-bubbles solution on ultrasound imaging. We collected US images of the vessel phantom filled either with the nano-bubbles solution (test) or PBS (control) using HDI 5000 ultrasound imaging system and a 10 MHz linear array imaging probe, which matches the frequency range used for clinical prostate imaging.[107] US backscatter was collected from a 2-5 mm×2-5 mm region-of-interest (ROI) inside the vessels filled with the nano-bubbles solution and PBS. Selection of this ROI ensured that the signals collected for backscatter analysis were from inside the vessel and were not from the gelatin phantom. The scanner was set for its maximum dynamic range of 170 dB and gain adjusted for a moderately bright image without saturation. The median backscatter amplitude in a ROI with nano-bubbles solution was calculated and compared to that of PBS to evaluate the increase in echogenicity. Our initial results show a significant increase in backscatter amplitude for nano-bubbles solution by 58.8±5.97 dB compared to PBS as clearly shown by the US images (FIGS. 4A to 4C).

We also tested the stability of our nano-bubbles in kidney at body temperature (37° C.) to show whether they are going to be visible for sufficient treatment time or not. We injected nano-bubbles into kidney at 37° C. and record continuously backscatter image using HDI 5000 ultrasound imaging system and a 10 MHz linear array imaging probe (FIG. 5). Nano-bubbles were still visible 30 min after injection, but increased in speckle amplitude likely a result of aggregation at the injection site (FIG. 6).

Histotripsy with Nano-Bubbles:

In a histotripsy-induced cavitation process, the gas nuclei rapidly grow to 10-100 μm followed by violent collapse to produce cellular disruption.[54,108] We hypothesized that similar bubble expansion can be achieved with the nano-bubble contrast agents at a significantly reduced pressure with low frequency (<500 kHz) US. To test this hypothesis, we simulated the peak negative pressure threshold required to expand a nano-bubble contrast agent with a diameter of 100-500 nm to reach 50 μm in soft tissue at 0.2, 0.5, and 1.1 MHz. The simulation shows that the pressure threshold decreases with decreasing the US frequency (FIG. 7A). For example, the pressure threshold is 1.7 MPa at 200 kHz, 6.3 MPa at 500 kHz, and 21.3 MPa at 1.1 MHz, which is significantly lower compared to the ~30 MPa threshold observed without the nano-bubble contrast agents. To validate the simulation results, we exposed PBS (control) and nano-bubbles (test) solutions heated to 37° C. (body temperature) to a 1-cycle long histotripsy pulse using a 500 kHz focused transducer (20 cm diameter and 15 cm focal distance) while imaging the cavitation in both solutions using a high speed camera (Phantom V210, Vision Research). No cavitation was observed in the PBS solution with a peak negative pressure as high as 25 MPa, which is the maximal peak negative pressure for this transducer (FIG. 7B). In comparison, individual cavitation began to form at peak negative pressure of 7 MPa in the nano-bubbles solution, which correspond very well with the simulation results (FIGS. 7A & 7B). By increasing the pressure, the area of the focal zone with higher pressure than the cavitation threshold also increased, which produced a larger and denser bubble cloud (FIG. 7B). The bubbles within the cloud grew up to 500 μm before their collapse.

Bubble expansion was analyzed by time and results showed that nano-bubbles expanded to over 600 μm before collapse within 120 μs (FIG. 8). We also tried multifocal ablation using nano-bubbles. Focal region contains two dialysis tubes filled with nano-bubbles and cavitation occurs only sight of nano-bubbles at intermediate pressure (17.3 MPa) (FIG. 9).

Investigating the Echogenicity and Stability of the Nano-Bubbles

Recent reports[72] showed that lipid micro-bubbles modified with pluronic polymers distributed to the tumor tissue raised in the flanks of nude mice in <5 min after their injection but the observed enhancement in US signal sharply decayed within few minutes. In comparison, our results show that shell cross-linked nano-bubbles exhibit a significant increase in backscatter amplitude compared to PBS solution (FIG. 4C) throughout the duration of the imaging experiment (~45 minutes), which suggest their high stability.

The echogenicity and stability of different nano-bubbles at physiologic conditions (pH 7.4; 37° C.) are investigated to identify the formulations that retain >80% of the initial backscatter amplitude (recorded at t=0 min) for ≥120 minutes, which, based on published reports[72,82], is a sufficient time for the targeted nano-bubbles to "home" to tumor tissue and increase the contrast of the cancer micro-foci on US imaging. Following the experiment plan described above, a vessel phantom is filled with different cross-linked nano-bubbles and their backscatter amplitude (i.e. echogenicity) is measured and compared to PBS solution (control) as a function of time using a research US imaging system (Verasonics) with a 10 MHz linear array, which is similar in frequency and array type to the transrectal US imaging probe clinically used for prostate imaging. The backscatter intensity from the nano-bubbles are based on the mean speckle amplitude within a region-of-interest (ROI) in the vessel phantom. Whether the nano-bubbles undergo cavitation and subsequently dissolve under insonificaiton of diagnostic US (Mechanical index <1.9) is tested by increasing the US power output from low to high, recording US backscatter, and identifying the power/mechanical index level at which the backscatter intensity significantly drops for each nano-bubble formulation, which indicates cavitation/dissolution.[110] In-phase/quadrature (IQ)) data are collected and processed using MATLAB (Mathworks) for backscatter analysis. These experiments are carried out in triplicates (n=3) for each nano-bubble formulation (test) and the control (PBS), followed by statistical analysis of the difference in backscatter amplitude using student t-test with a confidence interval of 95%, wherein $P \leq 0.05$ indicates statistical difference between groups. Physical stability (aggregation or dissolution) of the nano-bubbles under insonificiation is examined by measuring the size and size distribution at different time points using dynamic light scattering (Brookhaven Instruments). Results of this study are expected to identify the composition(s) of the most stable nano-bubble contrast agents, which are then used to prepare J591-targeted nano-bubbles for subsequent in vitro and in vivo experiments.

Formulation of J591-Targeted Nano-Bubbles

J591 is a monoclonal antibody that specifically binds to the extracellular domain of PSMA, a molecule overexpressed on the surface of prostate cancer cells,[111] which led to its clinical use for targeted delivery of therapeutic radionuclides to prostate cancer tissue.[112-115] Consequently, J591 monoclonal is proposed for use in targeting our nano-bubbles to recurrent prostate cancer micro-foci. The J591 antibody is conjugated to the carboxylic group of COOH-PEG-Alkyne via a standard EDC/NHS coupling reaction following published protocols[116] to prepare J591-PEG-alkyne conjugate, which reacts with PAA and P(MMA-co-HDFMA) blocks following the methods described earlier to prepare $J591\text{-}(PEG)_x\text{-}(PAA)_y\text{-}b\text{-}P(MMA\text{-}co\text{-}HDFMA)_z$ polymers. The molar ratio of J591-polymer conjugates (10%, 25%, and 50%) mixed with non-targeted tri-block copolymer are changed to vary the number of J591 targeting ligands displayed on nano-bubbles surface. The physicochemical properties, echogenicity, and stability of J591-targeted nano-bubbles are investigated using the methods described above.

In Vitro Imaging of Prostate Cancer Spheroids Using Targeted Nano-Bubbles

C42B (PSMA+) prostate cancer cells are cultured to form 3D spheroids with different sizes (50-500 μm) following our published protocols.[119] The spheroids surface is fluorescently labeled with Streptavidin-Alexa Fluor488 dye (green) via an established copper-free "click" coupling reaction[120] to allow spheroids imaging using fluorescence microscopy. Fluorescently-labeled spheroids are seeded in cubic-shaped side-chambers (500 μm×500 μm×500 μm) distributed on the sides of a microfluidic channel (100 μm height×2 mm width)[121] patterned in an optically-transparent fibrin gel phantom to mimic the micro-foci of prostate cancer cells in vitro. The inlet and outlet of the microfluidic channel are fitted with a PE tube and the inlet is connected to an automated syringe pump to fill the microfluidic channel and the side-chambers with different concentrations ($1\times10^4$, $1\times10^8$, $1\times10^{12}$ nano-bubbles/mL) of targeted nano-bubbles. Prostate cancer spheroids are imaged using the Verasonics system and the 10 MHz imaging probe for 120 minutes. The size and location of the regions with enhanced echogenicity on US images are compared to the fluorescent images of the spheroids to determine if they match. The IQ data collected from the Verasonics system are used to calculate the contrast at the spheroids location with respect to the phantom background, which allows us to monitor the binding of targeted nano-bubbles to spheroids surface as a function of: i) spheroids size, ii) nano-bubbles concentration, iii) number of targeting ligands per nano-bubble, and iv) incubation time. Results are expected to show the optimum concentration of nano-bubbles and number of targeting ligands/nano-bubble required for binding to prostate cancer spheroids. Using this experimental approach, the binding of targeted nano-bubbles are compared to C42B (PSMA+) and PC-3 (PSMA-) spheroids using US imaging to evaluate their binding specificity.

In Vivo Imaging of Prostate Cancer Cells Using Targeted Nano-Bubbles

Orthotopic cancer models have been developed by injecting ~$1\times10^6$ C42B-Lux and PC-3-Lux prostate cancer cells (expressing the luciferase enzyme) into the dorsolateral lobe of the prostate gland of male CB17 SCID mice and monitoring their growth by bioluminescence imaging (BLI) using IVIS imaging system (Caliper Life Sciences).[122-124] This orthotopic mice model (C42B-Lux) is used to investigate if targeted nano-bubbles can selectively "home" to the implanted cancer cells and enhance their contrast on US imaging. The tumor-bearing mice are divided into two groups (n=5/group) where targeted nan-bubbles are administered to the $1^{st}$ group (test) at the concentration that produced highest echogenic signal (identified the above experiment) and an equal volume of saline is administered to the $2^{nd}$ group (control) via tail vein injections. The change in tumor volume is monitored using luminescence imaging every 3 days for a total of 6 weeks following established BLI protocols.[123,124] Using the Verasonics system and 10 MHz imaging probe, the prostate of both mice groups are imaged on the same day of the BLI following established US imaging protocols.[125,126] Briefly, image acquisition is started 10 s before administering the assigned solution (nano-bubbles or saline) and imaging is continued for an additional 60 s followed by acquiring 10 s video clips at 5, 10, 15, 30, 45, 60, 75, 90, 105, and 120 minutes after injection. The image series is registered at each time point to the t=0 images using 2D rigid body registration before calculating the mean gray scale value in the hyperechogenic zone in the prostate for all time points then normalize the images by the baseline value (pre-injection) for each mouse. The fold enhancement in echogenic signal as a function of time is calculated by subtracting the baseline value from each time point for each mouse. The calculated fold enhancement in echogenic signal in mice treated with targeted nano-bubbles is compared to the calculated echogenic signal in mice treated with saline at the same time points to determine: i) if targeted nano-bubbles will "home" to tumor lesion, and ii) the smallest tumor volume that can be imaged using these targeted nano-bubbles. The hyperechogenic zone on US images are compared to the zone of highest luminescence on BLI in all studies to confirm that enhanced scattering is localized to prostate cancer cells.

In Vivo Toxicity of Targeted Nano-Bubbles

The hematologic (RBC & WBC and hematocrit value), liver (serum levels of ALT and AST enzymes), kidney (serum creatinine level), and heart (serum ROS level) toxicity of targeted nano-bubbles compared to saline-treated mice 24-hours after each injection are investigated using the tests listed between parentheses. A blinded examination of the heart, lungs, liver, kidneys, and spleen isolated from both mice groups at the end of the imaging experiments are carried out to identify pathological signs of nano-bubbles toxicity.

Multi-Foci Targeted Ablation of Prostate Cancer Cells In Vitro

Different concentrations ($1 \times 10^4$, $1 \times 10^8$, $1 \times 10^{12}$ nano-bubbles/mL) of targeted nano-bubbles are loaded into the microfluidic channel embedded in fibrin gel phantom containing prostate cancer spheroids and are incubated for a period of time (as identified in an above experiment) to allow their binding to cancer cells. Low frequency (<500 KHz) and low pressure (FIG. 8) US is applied to the spheroids to investigate the feasibility of cell disruption by the expansion and collapse of the bound nano-bubbles. The generation and expansion of micro-bubbles are simultaneously monitored using a high speed camera (Phantom V210, Vision Research). Previous animal experiments showed that short pulses (<5 cycles) at a low pulse repetition frequency (PRF) were efficient in fractionating canine prostate tissue.[52,58,127] These parameters are used as a starting point and the effect of combinations of different parameters (PRF, pulse duration, pressure) are investigated to identify the combination that produces precise and efficient ablation of cancer spheroids in the fibrin gel, which is used in subsequent in vivo studies. Spheroids disruption is evaluated by comparing their fluorescent images before and after each treatment.

Selective In Vivo Ablation of Prostate Cancer Cells Using Targeted Nano-Bubbles

C42B-Lux cancer cells are injected into the prostate of twenty mice and the cells are allowed to grow for 5 weeks while regularly monitoring the change in tumor volume using BLI before dividing the mice into four groups (n=5/group) where each group will receive a different treatment (Table 5).

| Group | Targeted Nano-bubbles | Histotripsy | Saline |
|---|---|---|---|
| Group 1 (Test)++ | + | + | − |
| Group 2 (Test)+ | + | − | − |
| Group 3 (Test)+ | − | + | − |
| Group 4 (Control) | − | − | + |

100 μL of targeted nano-bubbles solution are administered to the mice in group 1 (test) via tail vein injections after adjusting the solution concentration to deliver the number of nano-bubbles proved most efficient in ablating cancer spheroids in vitro. The histotripsy parameters that were most effective in ablating prostate spheroids in vitro to group 1 are applied and the resulting therapeutic activity is evaluated by measuring the reduction in the intensity of the luminescence signal after the treatment compared to its baseline value before the treatment using BLI. US imaging is also used to monitor the drop in echogenic signal (hypoechogenic) of the cancer lesion after the histotripsy treatment. The independent effect of targeted nano-bubbles (group 2) and histotripsy (group 3) on ablation of prostate cancer cells using the same nano-bubbles dose is investigated and the histotripsy parameters are applied to group 1. Saline injections are given to Group 4 and this group is used as a control. The prostates of all 20 mice are harvested and submitted for microscopic analysis by the histology core to determine the size of ablated tumor region and the extent of damage in neighboring healthy tissue in response to each treatment. This pilot study is expected to establish the therapeutic potential of targeted nano-bubble contrast agents in combination with histotripsy in ablating prostate cancer cells. Statistical comparison between different groups are performed using ANOVA with a confidence interval of 95% where P≤0.05 will indicate statistical difference between groups.

Example 3

The following materials and techniques were used in Examples 4 to 10.

Materials:

Methyl methacrylate (MMA, Sigma-Aldrich, 99%), 3,3,4,4,5,5,6,6,7,7,8,8,9,9,10,10,10-heptadecafluorodecyl methacrylate (HDFMA, Sigma-Aldrich, 97%), tert-butyl acrylate (tBA, Sigma-Aldrich, 98%) and N,N,N',N'',N''-pentamethyldiethylenetriamine (PMDETA, Sigma-Aldrich, 99%) were passed through basic alumina column to remove the inhibitor. N-(n-Pentyl)-2-pyridylmethanimine was synthesized according to the literature procedure.[2] Copper (I) bromide (CuBr, Sigma-Aldrich, 99.9%), 2-bromoisobutyryl bromide (Fluka, >97%), tetrahydrofuran anhydrous (THF, Sigma-Aldrich, >99.9%), N,N' Dicyclohexylcarbodiimide (DCC, Sigma-Aldrich, 99%), dimethylaminopyridine (DMAP, Acros, 99%), 4-pentynoic acid (Sigma-Aldrich, 99%), furan (Sigma-Aldrich, 99%), maleic anhydride (Fluka, 99%), 9-anthracene methanol (Aldrich, 99%), N-hydroxy succinimide (NHS, Fluka, 97%), N-(3-Dimethylaminopropyl)-N-ethylcarbodiimide hydrochloride (EDC, Fluka >98%), poly(ethylene glycol) monomethylether (Me-PEG, $M_n$: 2000 and 5000, Sigma-Aldrich), sodium azide (NaN$_3$, Acros, 99%), 2-(N-morpholino)ethanesulfonic acid monohydrate (MES, Acros, 99%), triethylamine (TEA, Sigma-Aldrich, 99%), trifluoroacetic acid (TFA, Acros, 99%), ethylene carbonate (Sigma-Aldrich, 98%), 2,2'-(ethylenedioxy)-bis(ethylamine) (Sigma-Aldrich, 98%) were used as received. G5-(NH$_2$)$_{128}$ PAMAM dendrimers with DAB core, and bovine serum albumin (BSA) were purchased from Sigma-Aldrich Inc. (St. Louis, Mo.). RPMI medium 1640, fetal bovine serum (FBS), 0.25% trypsin/0.20% ethylene diamine teraacetic acid (EDTA), phosphate buffered saline (PBS), penicillin/streptomycin/amphotericin, sodium pyruvate, and non-essential amino acid solutions were purchased from Invitrogen Corporation (Carlsbad, Calif.). MTT Assay Kit was purchased from American Type Culture Collection (Manassas, Va.). T-75 flasks, Costar 96-well plates, and cell culture supplies were purchased from Corning Inc. (Corning, N.Y.).

Characterization:

$^1$H NMR and $^{13}$C NMR spectra of 5-10% (w/w) solutions in CDCl$_3$ or D$_2$O with Si(CH$_3$)$_4$ as an internal standard were recorded using 400 MHz and 500 MHz Varian Mercury system (Palo Alto, Calif.) at room temperature, respectively. Gel permeation chromatography (GPC) measurements were obtained from a Viscotek GPCmax Autosampler system consisting of a pump and Water 2414 refractive index (RI) detector. The molecular weight and molecular weight distribution of final polymers were determined based on their elution volume on an Styragel HR 4E column compared to a series of poly(methyl methacrylate) standards (PolyAnalitik Inc, Canada) using THF as a mobile phase at a flow rate of 1 ml/min at 35° C. Data were analyzed using Viscotek OmniSEC Omni-01 software. FT-IR spectra were recorded on a Perkin-Elmer FT-IR Spectrum 4100 type A. Differential scanning calorimetry (DSC) was performed on Perkin-Elmer Diamond DSC calibrated with indium. Glass transition temperatures were measured, after a first heating (from 20° C. to 120° C.) and cooling (from 120° C. to 20° C.) cycle. Thermograms were recorded during the second heating cycle (from 20 to 120° C.) at 10° C./min under nitrogen flow and the glass transition temperature (T$_g$) was determined at the midpoint between upper and lower intersection of the baseline with the tangent to the transition step. Micelles size were measured using Dynamic Light Scattering (DLS) 90Plus particle size analyzer with ZetaPALS capability (Brookhaven Instruments Corporation, Holtsville, N.Y.).

Synthesis of 9-anthyrylmethyl 2-bromo-2-methyl propanoate 9-anthyrylmethyl 2-bromo-2-methyl propanoate was synthesized by following literature.[3] 9-Anthracene methanol (1.50 g, 7.18 mmol) and DMAP (0.175 g, 1.44 mmol) were dissolved in 50 mL of CH$_2$Cl$_2$, and Et$_3$N (1.2 mL, 8.6 mmol) was added. The reaction mixture was then cooled to 0° C. 2-bromo isobutyryl bromide (1.82 g, 7.89 mmol) was added dropwise within 30 minutes to this solution. The reaction mixture was stirred for 15 min at 0° C. then for overnight at room temperature. The ammonium salt was filtered off and the solvent was evaporated under reduced pressure. The remaining residue was extracted with CH$_2$Cl$_2$, and saturated aqueous NaHCO$_3$ and combined organic phases dried over Na$_2$SO$_4$. The solution was concentrated, and the crude product was purified by column chromatography over silica gel eluting with hexane/EtOAc (10:1) to give 5 as yellow solid. Yield: 2.15 g (84%). EIMS m/z 379.0 for [M+Na]+ C$_{19}$H$_{17}$O$_2$BrNa calculated 379.04. $^1$H NMR (500 MHz, CDCl$_3$, δ): 8.55 (s, 1H, ArH of anthracene), 8.35 (d, J. 8.99 Hz, 2H, ArH of anthracene), 8.05 (d, J=8.49 Hz, 2H, ArH of anthracene), 7.60-7.45 (m, 4H, ArH of anthracene), 6.24 (s, 2H, CH$_2$-anthracene), 1.89 (s, 6H, C(CH$_3$)$_2$—Br). $^{13}$C NMR (CDCl$_3$, δ): 172, 131.3, 131.1, 129.4, 129.1, 126.7, 125.5, 125.1, 123.9, 69.7, 55.9, 30.7.

Synthesis of 2-bromo-2-methyl-propionic acid 2-(3,5-dioxo-10-oxa-4azatricyclo[5.2.1.02,6]dec-8-en-4-yl)ethyl ester (Protected Maleimide Functional Initiator)

Protected-maleimide functional initiator was synthesized by following literature.[4] Maleic anhydride (10.0 g, 0.1 mol) was suspended in 30 mL of toluene and the mixture warmed to 80° C. Furan (11.3 mL, 0.15 mol) was added via syringe and the turbid solution was stirred for overnight. The mixture was then cooled to ambient temperature white solids formed during standing were collected by filtration and washed with 2×30 mL of diethyl ether afforded 3a,4,7,7a-tetrahydro-4,7-epoxyisobenzofuran-1,3-dione (1) as white needless. Yield: 12.35 g (74%). $^1$H NMR (500 MHz, CDCl$_3$, δ) 6.55 (s, 2H, CH═CH, bridge protons), 5.45 (s, 2H, —CHO, bridge-head protons), 3.15 (s, 2H, CH—CH, bridge protons). $^{13}$C NMR (CDCl$_3$, δ): 169.9, 137.0, 82.2, 48.7.

The adduct 1 (10.0 g, 60.0 mmol) was suspended in methanol (150 mL) and the mixture cooled to 0° C. A solution of ethanolamine (3.6 mL, 60 mmol) in 30 mL of methanol was added dropwise (10 min) to the reaction mixture, and the resulting solution was stirred for 5 min at 0° C., then 30 min at ambient temperature, and finally refluxed for 6 h. After cooling the mixture to ambient temperature, solvent was removed under reduced pressure, and residue was dissolved in 150 mL of CH$_2$Cl$_2$ and washed with 3×100 mL of water. The organic layer was separated, dried over Na$_2$SO$_4$ and filtered. Removal of the solvent under reduced pressure gave white-off solid which was further purified by flash chromatography eluting with ethylacetate (EtOAc) to give the product, 2-(2-hydroxyethyl)-3a,4,7,7a-tetrahydro-1H-4,7-epoxyisoindole-1,3(2H)-dione (2), as a white solid. Yield: 3.3 g (27%). $^1$H NMR (500 MHz, CDCl$_3$, δ): 6.53 (s, 2H, CH═CH, bridge protons), 5.29 (s, 2H, —CHO, bridge-head protons), 3.79-3.70 (m, 4H, NCH$_2$CH$_2$OH), 2.90 (s, 2H, CH—CH, bridge protons). $^{13}$C NMR (500 MHz, CDCl$_3$, δ): 176.8, 136.5, 80.9, 60.1, 47.5, 41.7.

In a 250 mL of round bottom flask were added 2 (2.0 g, 9.55 mmol) and Et$_3$N (1.44 mL, 10.54 mmol) in 100 mL of THF. The mixture was cooled to 0° C., and a solution of 2-bromo isobutyryl bromide (2.34 g, 10.0 mmol) in 25 mL of THF was added dropwise (30 min) to the reaction mixture. The white suspension was stirred for 3 h at 0° C. and subsequently at ambient temperature for overnight. The ammonium salt was filtered off and the solvent was removed under reduced pressure to give a pale-yellow residue that was further purified by column chromatography over silica gel eluting with EtOAc/hexane (1:4) to give compound as a white solid. Yield: 2.5 g (91%). EIMS m/z 338.0 for [M+Na]+C$_{14}$H$_{16}$NO$_5$BrNa calculated 380.02. $^1$H NMR (500 MHz, CDCl$_3$, δ) 6.52 (s, 2H, CH═CH, bridge protons), 5.27 (s, 2H, —CHO, bridge-head protons), 4.33 (t, J=10.5 Hz, 2H, NCH$_2$CH$_2$OC═O), 3.77 (t, J=10.5 Hz, 2H, NCH$_2$CH$_2$OC═O), 2.87 (s, 2H, CH—CH, bridge protons), 1.90 (s, 6H, C(CH$_3$)$_2$—Br). $^{13}$C NMR (500 MHz, CDCl$_3$, δ): 175.8, 171.3, 136.5, 80.8, 62.1, 55.6, 47.4, 37.5, 30.5.

Synthesis of Protected Maleimide Functional Poly(heptadecafluorodecyl methacrylate-co-methyl methacrylate) (PMI-P(HDFMA-co-MMA)-Br)

CuBr (33.5 mg, 2.33×10$^{-4}$ mol), N-(n-Pentyl)-2-pyridylmethanimine (86.5 µL, 4.68×10$^{-4}$ mol), protected maleimide functional initiator (83.3, 2.23×10$^{-4}$ mmol), MMA (2 mL, 1.87×10$^{-2}$ mol), HDFMA (2.07 mL, 4.65×10$^{-3}$) and 3.5 mL Toluene were introduced in a Schlenk tube under argon. The tube was heated at 90° C. in an oil bath and stirred 1 h 40 min. Then the mixture was diluted with THF, and passed through an alumina column to remove the complex salts. Precipitation of the polymer was performed in a ten-fold volume of heptane. The solid was then collected after filtration. Conversion: 25.4%, M$_{n,theo}$:5100 g/mol, M$_{n,NMR}$: 6620 g/mol, M$_{n,GPC}$: 5930 g/mol, M$_w$/M$_n$:1.13. $^1$H NMR (500 MHz, CDCl$_3$, δ): 6.54 (s, 2H, CH═CH), 5.28 (s, 2H, —CHO), 4.47 (t, 2H, NCH$_2$CH$_2$OC═O), 4.26 (bs, CO—O—CH$_2$—CH$_2$—CF$_2$), 3.77 (t, 2H, NCH$_2$CH$_2$OC═O), 3.60 (bs, CO—O—CH$_3$), 2.90 (s, 2H, CH—CH), 2.49 (bs, CO—O—CH$_2$—CH$_2$—

$CF_2$), 2.05-0.85 (m, $CH_2$—$CCH_3$, CO—$(CH_3)_2$). $^{19}$F NMR (470 MHz, $CDCl_3$, δ): −80.8, −113.5, −121.9, −122.7, −123.6, −121.1.

Synthesis of Anthracene Functional Poly(t-Butyl Acrylate) (Anth-PtBA-Br):

CuBr (97.8 mg, $6.82 \times 10^{-4}$ mol), PMDETA (142.4 µL, $6.82 \times 10^{-4}$ mol; anthracene functional initiator (0.244, $6.82 \times 10^{-4}$ mol) as an initiator, t-BA (10 mL, $6.82 \times 10^{-2}$ mol), and ethylene carbonate (10% w/w, 0.92 g) were introduced in a round bottom flask (50 mL) under the argon. The mixture was degassed by three freeze-pump-thaw cycles and left argon atmosphere at 80° C. for 90 min. After the given time, the mixture was diluted with THF. Then the copper complex was removed out by passing through a neutral alumina column, and THF was removed by rotary evaporation. The mixture was precipitated in cold methanol/water (80/20 v/v). After decantation, the polymer was dissolved in $CH_2Cl_2$, extracted with water and the water phase was again extracted with $CH_2Cl_2$ and combined organic phase was dried over $Na_2SO_4$. Finally, the organic phase was evaporated to give anthracene functional poly(tert-butyl acrylate). Conversion: 9%, $M_{n,theo}$: 1510 g/mol, $M_{n,NMR}$:1640 g/mol, $M_{n,GPC}$: 2000 g/mol, $M_w/M_n$:1.26. $^1$H NMR (500 MHz, $CDCl_3$, δ): 8.51 (s, 1H, ArH of anthracene), 8.40 (d, 2H, ArH of anthracene), 8.04 (d, J=8.49 Hz, 2H, ArH of anthracene), 7.58-7.50 (m, 4H, ArH of anthracene), 6.12 (s, 2H, $CH_2$-anthracene), 4.11 ($CH_2CH$—Br), 2.26 ($CH_2CH$—CO), 1.86 (6H, O—CO—$C(CH_3)_2$), 1.45 (9H, CO—O—$C(CH_3)_3$).

Azidation of Anthracene Functional Poly(tert-butyl acrylate) (Anth-PtBA-$N_3$):

Anthracene functional Poly(t-butyl acrylate) (0.5 g, $3.04 \times 10^{-4}$ mol) and 20 equivalent $NaN_3$ (0.396 g, $6.09 \times 10^{-3}$ mol) were stirred in DMF at 50° C. for overnight. The polymer was dissolved in $CH_2Cl_2$, extracted with water and the water phase was again extracted with $CH_2Cl_2$ and combined organic phase was dried over $Na_2SO_4$. Finally, the organic phase was evaporated to give athracene functional azide terminated poly(tert-butyl acrylate). $^1$H NMR (500 MHz, $CDCl_3$, δ): 8.51 (s, 1H, ArH of anthracene), 8.39 (d, J=8.49 Hz, 2H, ArH of anthracene), 8.05 (d, J=8.99 Hz, 2H, ArH of anthracene), 7.58-7.50 (m, 4H, ArH of anthracene), 6.12 (s, 2H, $CH_2$-anthracene), 3.77 ($CH_2CH$—$N_3$), 2.26 ($CH_2CH$—CO), 1.86 (6H, O—CO—$C(CH_3)_2$), 1.45 (9H, CO—O—$C(CH_3)_3$).

Synthesis of Alkene Functional Polyethylenglycol (Alkene-PEG):

$PEG_{2000}$ (5.0 g, $2.5 \times 10^{-3}$ mol) and 4-pentynoic acid (0.367 g, $3.75 \times 10^{-3}$ mol) were dissolved in 25 mL of $CH_2Cl_2$. DMAP (0.308 g, $2.5 \times 10^{-3}$ mol) and a solution of DCC (0.770 g, $3.75 \times 10^{-3}$ mol) in 10 mL of $CH_2Cl_2$ were successively added to the reaction mixture followed by stirring overnight at room temperature. After filtration of the salt, the solution was concentrated and solution of alkyne-PEG was precipitated in diethyl ether tree times and filtered. (Yield: 3.86 g). Functionalization efficiency: 92%. $^1$H NMR (500 MHz, $CDCl_3$, δ): 4.26 9 (t, 2H, CO—O—$CH_2$), 3.71 (t, 2H CO—O—$CH_2$—$CH_2$—O), 3.65 (bs, 180H, $OCH_2CH_2$), 3.38 (s, 3H, O—$CH_3$), 2.58 (2H, $CH_2CH_2$—CO—O), 2.51 (2H, $CH_2CH_2$—CO—O), 1.99 (1H, alkyne proton).

Synthesis of Poly[(heptadecafluorodecyl methacrylate-co-methyl methacrylate)-b-(tert-butyl acrylate)-b-ethyleneglycol] Triblock Copolymer via one-pot Diels-Alder/Azide-Alkene Click Reaction (P((HDFMA-co-MMA)-b-PtBA-b-PEG)):

Protected maleimide functional P(MMA-co-HDFMA) (0.182 g, $2.75 \times 10^{-5}$ mol), Anth-PtBA-$N_3$ (0.050 g, $3.03 \times 10^{-5}$ mol), and PEG-alkyne (0.071 g, $3.03 \times 10^{-5}$ mol) were dissolved in Toluene (10 mL) in a Schlenk tube. CuBr (5.21 mg, $3.63 \times 10^{-5}$ mol) and PMDETA (7.6 µL, $3.63 \times 10^{-5}$ mol) were added, and the reaction mixture was degassed by three freeze-pump-thaw cycles and stirred at 110° C. for 48 h. The mixture was passed through alumina column to remove copper catalyst using THF as an eluent. Concentrated polymer solution was precipitated in hexane. Further precipitations were performed from cold methanol to remove excess of PEG-Alkyne Anth-PtBA-$N_3$ polymers and possible PEG-b-PtBA copolymer completely. (Yield: 90 mg) $^1$H NMR (500 MHz, $CDCl_3$, δ): 7.58-7.19 (8H, aromatic protons), 5.47-5.29 (3H, $CH_2$—CH-triazole and CO-β-$CH_2$-cycloadduct), 4.78 (2H, CH bridge protons), 4.24 (CO—O—$CH_2$—$CH_2$—$CF_2$), 3.78 (2H, CO—O—$CH_2$—$CH_2$—N), 3.63 ($OCH_2CH_2$), 3.47 (CO—O—$CH_3$), 3.38 (3H, $OCH_2CH_2O$—$CH_3$), 3.28 (4H, CO—O—$CH_2$—$CH_2$—N and CH bridge protons of cycloadduct), 3.02 (2H, triazole-$CH_2$—$CH_2$—CO—O), 2.75 (2H, triazole-$CH_2$—$CH_2$—CO—O), 2.47 (CO—O—$CH_2$—$CH_2$—$CF_2$), 2.25 ($CH_2CH$—CO), 2.03-0.84 (O—CO—$C(CH_3)_2$, CO—O—$C(CH_3)_3$ and rest of the backbone protons).

Synthesis of Poly[(heptadecafluorodecyl methacrylate-co-methyl methacrylate)-b-(acrylic acid)-b-ethyleneglycol] Triblock Copolymer (P((HDFMA-co-MMA)-b-PAA-b-PEG)):

P(HDFMA-co-MMA)-b-PtBA-b-PEG copolymer was dissolved in dichloromethane and 10 fold excess of TFA (equivalent to tert-butyl group) was added at 0° C. under argon atmosphere. Reaction mixture was stirred 30 min at this temperature and 24 h stirred at room temperature. Dichloromethane and TFA were evaporated with air stream and polymer was precipitated in methanol. $^1$H NMR (500 MHz, $CDCl_3$, δ): 7.58-7.19 (8H, aromatic protons), 5.47-5.29 (3H, $CH_2$—CH-triazole and CO—O—$CH_2$-cycloadduct), 4.78 (2H, CH bridge protons), 4.24 (CO—O—$CH_2$—$CH_2$—$CF_2$), 3.78 (2H, CO—O—$CH_2$—$CH_2$—N), 3.63 ($OCH_2CH_2$), 3.47 (CO—O—$CH_3$), 3.38 (3H, $OCH_2CH_2O$—$CH_3$), 3.28 (4H, CO—O—$CH_2$—$CH_2$—N and CH bridge protons of cycloadduct), 3.02 (2H, triazole-$CH_2$—$CH_2$—CO—O), 2.75 (2H, triazole-$CH_2$—$CH_2$—CO—00-0), 2.47 (CO—O—$CH_2$—$CH_2$—$CF_2$), 2.25 ($CH_2CH$—CO), 2.03-0.84 (O—CO—$C(CH_3)_2$, and rest of the backbone protons).

Preparation of Shell Cross-Linked Micelles:

PEG-b-(PAA)-b-P(MMA-co-HDFMA) copolymers were dissolved in THF (0.1 or 0.2% w/v) and cooled down to 0° C. before addition of PFP (1 or 2% v/v). Equal amount of water was slowly added to this solution mixture to trigger micelle formation. The micelles solution was transferred into a dialysis bag (MWCO of 1 KDa) and dialyzing against ice cold MES solution or water to remove THF. After 12 hours of dialysis, milky solution of PFP encapsulated noncross-linked micelles was obtained. 5 mL of this micelles solution ($3.18 \times 10^{-7}$ mol of ABC-1, $3.02 \times 10^{-7}$ mol of carboxylic acid groups) was transferred into round bottom flask. 121.1 µl of NHS solution ($6.05 \times 10^{-6}$ mol, 50 mM solution in 100 mM (pH: 5.5) MES buffer pH: 5.5) and 242.2 µl of EDC solution ($1.21 \times 10^{-6}$ mol, 50 mM solution in 100 mM (pH: 5.5) MES buffer) were added to micelles solution and stirred for 45 min followed by addition 151.4 µl of 2,2'-(ethylenedioxy)-bis (ethylamine) as a cross-linker ($1.51 \times 10^{-6}$ mol, 10 mM solution in (pH7.4) PBS buffer). After 6 h stirring in ice bath, micelles solution was transferred into a dialysis bag to remove buffer impurities. Micelles size was determined using dynamic light scattering before and after crosslinking.

Cytotoxicity of Micelles Prepared Using ABC-1 and ABC-2 Copolymer:

Briefly, PC-3 cells were seeded in 96-well plates at a seeding density of 1×10$^5$ cells/well and allowed to adhere overnight before replacing the culture medium with RPMI medium 1640 solution (without phenol red) containing different concentration of micelles and incubating for 24 h under normal culture conditions. The cells were then exposed to 10 µL MTT reagent included in the assay kit following the manufacturer's guidelines, for 2 hours which results in reduction of MTT reagent to purple formazan precipitate. MTT reagent detergent (100 µL) was added to each well and incubated for 3 h in dark at room temperature, followed by measuring the absorbance of this mixture at 570 nm using a Multiskan microplate reader (Thermo Fisher Scientific Inc., Waltham, Mass.). Contribution of free culture medium was eliminated by subtracting the absorbance of equal volume of culture medium at this wavelength. PC-3 cells with RPMI1640culture medium (untreated cells) and 5% v/v Triton X-100 solution were used as negative and positive controls, respectively. The micelles concentrations that result in statistically different than untreated cell were considered cytotoxic.

Opsonization of Micelles Solution:

Fluorescence spectroscopy was used to investigate the interaction between BSA and different micelles solutions. BSA fluoresces with maximum of 340 nm when it is excited at 280 nm because of tryptophan residue. Opsonization of micelles and G5 dendrimer as a control was performed in PBS (pH: 7.4) at a 120 µM concentration in a quartz cuvette. Opsonization was initiated by addition of 0.2 mg/mL BSA (3 µM). Quenching of tryptophan fluorescence due to particle binding was recorded using a QM4 fluorescence spectrophotometer (Perkin-Elmer, Waltman, Mass.). The sample was maintained at 37° C. using a heated cuvette holder with magnetic stir bar, excitation wavelength set to 284 nm ($\lambda_{max}$ of excitation scan) and emission spectrum were recorded from 300 to 450 nm over a 60 min of incubation period. Excitation and emission slit widths set at 5 nm. The fluorescence quenching efficiency is defined as $I_o/I$, where $I_o$ and $I$ are the peak fluorescence intensity at initiation of opsonization and as a function of time, respectively.

Red Blood Cell Tissue Phantom Experiment:

Agarose gel phantoms with an embedded red blood cell (RBC) layer were used to demonstrate the ability of using micelles to mechanically ablate tissue. This tissue phantom has been previously utilized as a model to study the effectiveness of histotripsy fractionation and shown to correlate with tissue fractionation.[1] Tissue phantoms were prepared using a mixture of agarose power (Type VII; Sigma-Aldrich Co., St. Louis, Mo., USA) and canine RBCs in 0.9% isotonic saline. Fresh canine blood was obtained from adult research subjects in an unrelated study and added to an anticoagulant solution of citratephosphate-dextrose (CPD) (#C1765; Sigma-Aldrich Co.) with a CPD-to-blood ratio of 1:9 mL. Whole blood was separated in a centrifuge at 3000 rpm for 10 min. The plasma and white buffy coat were removed, and the RBCs were saved for addition to the phantom.

Agarose was slowly combined with saline while stirring at 20° C. (1.5% w/v agarose/saline), forming a translucent solution. The solution was heated in a microwave oven for 30 s and then stirred. Heating at 30 s intervals and stirring was repeated until the solution turned entirely transparent. The solution was then placed under a partial vacuum of 20.5 µsi for 30 min to degas the mixture. After removing the mixture from the vacuum, mixture was cooled to 37° C. and PFP encapsulated micelles were added to experimental phantom for comparison with micelles without PFP and no micelles phantoms. A layer of these phantom mixtures were then poured into a rectangular polycarbonate housing to fill half of it. The housing was placed in a refrigerator at 4° C. to allow the agarose to cool and solidify. The remaining agarose solution was kept at 37° C. A small amount of agarose solution was mixed with the RBCs (5% RBCs v/v). The frame with solidified agarose was removed from refrigeration, and a thin layer of the RBC-agarose solution was poured onto the gel surface to allow the entire surface to coat in a thin layer. After 5 min, the RBC-agarose layer was solidified, and the remaining agarose solution without RBCs was poured to completely fill the frame. This procedure created a thin layer of RBCs suspended in the center of the agarose phantom.

The focus of a 32 element 500 kHz transducer was aligned with the center of the red blood cell phantom layer. Histotripsy pulses were applied at a pulse repetition frequency of 10 Hz at peak negative pressures of 12.5, 17, and 22 MPa to the center of phantoms containing red blood cell layer embedded with PFP encapsulated micelles, empty micelles, and saline. Regular histotripsy pulses were applied at a pulse reputation frequency of 50 Hz at a peak negative pressure of 22 MPa. Histotripsy bubbles and red blood cell fractionation was monitored using a high-speed, 1 megapixel CCD camera (Phantom V210, Vision Research) capable of a maximum frame rate of 2000 fps. The camera was focused to the red blood cell layer and backlit by a continuous light source. The camera was triggered to record two images for each applied pulse, one 10 µs after the pulse reached the focus to visualized the bubble activity and another frame was captured between pulses to assess tissue damage. The camera exposure time was 10 µs. The bubbles appeared as black regions in the shadow graphic image while red blood cell fractionation was visualized as red blood cells turn transparent after fractionation. Tissue fraction was compared between RBC phantoms with PFP encapsulated micelles, empty micelles and saline as controls.

Example 4

Various amphiphilic copolymers with different hydrophilic/hydrophobic balance (HLB) ratio were designed and synthesized. The compositions and HLB ratio of ABC block copolymer summarized in Table 6.

TABLE 6

| # P Polymer | $M_{n,P(MMA\text{-}co\text{-}HDFMA)}{}^a$ (# of units) (g/mol) | $M_{n,PAA}{}^a$ (# of units) (g/mol) | $M_{n,PEG}{}^a$ (# of units) (g/mol) | $M_{nHP}/M_{nHF}{}^b$ | # of HP/# of HF units$^c$ | $M_{n,ABC}{}^a$ (g/mol) | $M_{n,GPC,ABC}{}^d$ (g/mol) | PD |
|---|---|---|---|---|---|---|---|---|
| 1 | 11390 (52.5) | 1650 (10) | 2000 (45) | 3.12 | 0.96 | 15040 | 14580 | 1.06 |
| 2 | 6720 (29) | 1650 (10) | 2000 (45) | 1.84 | 0.53 | 10370 | 9613 | 1.11 |
| 3 | 11390 (52.5) | 1750 (11) | 5000 (113) | 1.68 | 0.42 | 18140 | 17510 | 1.11 |
| 4 | 8050 (39.5) | 1650 (10) | 5000 (113) | 1.21 | 0.32 | 14700 | 17040 | 1.17 |

TABLE 6-continued

| # P Polymer | $M_{n,P(MMA\text{-}co\text{-}HDFMA)}{}^a$ (# of units) (g/mol) | $M_{n,PAA}{}^a$ (# of units) (g/mol) | $M_{n,PEG}{}^a$ (# of units) (g/mol) | $M_{nHP}/M_{nHF}{}^b$ | # of HP/# of HF units[c] | $M_{n,ABC}{}^a$ (g/mol) | $M_{n,GPC,ABC}{}^d$ (g/mol) | PD |
|---|---|---|---|---|---|---|---|---|
| 5 | 3130 (14) | 1750 (11) | 2000 (45) | 0.83 | 0.25 | 6750 | 6950 | 1.15 |
| 6 | 3130 (14) | 1750 (11) | 5000 (113) | 0.46 | 0.11 | 9770 | 12998 | 1.10 |

[a]Calculated from $^1$H NMR spectra.
[b]$M_{nHP}/M_{nHF}$: Molecular weight of hydrophobic block/molecular weight of hydrophilic block.
[c]# of HP/# of HF units: The number of hydrophobic units/the number of hydrophilic units.
[d]Determined from GPC by using PMMA standards, THF as an eluent at 35° C.

Each copolymer was used for preparation of micelles under the same conditions and micelle features were investigated. Similar trends were observed for almost all amphiphilic copolymers. When micelles were cross-linked, their size decreased compared to their non-crosslinked form. Also the temperature response of each was restricted by crosslinking: when non-crosslinked micelles were heated to body temperature, the non-crosslinked micelles expanded to a greater extent relative to cross-linked micelles. This is likely because increasing chain mobility by heat more effective for noncrosslinked micelles than cross-linked micelles formed linked polymer chains (FIG. 19A). We also know that evaporation of PFP is not possible in such a small volume at this temperature because of increasing Laplace pressure. We have started calling our nanoparticle as nano-droplets instead of nono-bubbles since PFP is still liquid both room and body temperature.

Some of the copolymer compositions could not retain their size when mechanical force was applied by filtration through a 0.8 micrometer filter. As can be seen in FIG. 19B, micelle size slightly decreased after filtration with 0.8 um filtered for those compositions having a lower $M_{nHP}/M_{nHF}$ value.

Based on this assay, two compositions were selected for further characterization and testing: Polymer 2 and 3 (as numbered in Table 1), which will be referred to as ABC1 and ABC2, respectively, hereinafter. While ABC1 and ABC2 are similar in size and HLB value, they differ by their hydrophobic core (6.7 kDa and 11.3 kDa) and size of PEG chains (2 kDa and 5 kDa).

Example 5

This example examines the differences between crosslinked and non-crosslinked shells.

Shell cross-linking is important for two reasons. First, it prevents the polymer chains from falling apart in the micelles, when diluted in the body under their critical micelles concentration. Second, it keeps PFP more stable in the core. Using Differential Scanning calorimetry (DSC), we tested whether or not the middle block was successfully crosslinked. Table 2 summarizes the thermal behavior of the crosslinked and non-crosslinked micelles, block copolymer and their precursors.

As shown in Table 7, P(HDFMA-co-MMA)-1 (6.7 KDa) has a glass transition temperature ($T_g$) of 61.4° C. which increases up to 76.5° C., when the molecular weight of polymer increases to 11.3 KDa. Since P(HDFMA-co-MMA) and PEG is not miscible blocks, the copolymers exhibited two transitions at measured temperature range (20-120° C.) which indicates melting points of PEG and glass transition ($T_g$) of P(HDFMA-co-MMA), respectively. Increasing PEG and P(HDFMA-co-MMA) length increased the related transition. As can be seen in Table 2, non-crosslinked micelles showed similar transitions with related ABC block copolymers, while the cross-linked version exhibited higher transition temperature, presumably due to a restricted mobility of the polymer chains during transition. Second transition temperature difference between cross-linked and noncrosslinked micelles of ABC-2 copolymer was not significant as much as ABC-1 copolymer since longer PEG chains (5 kDa) contributes more as a plasticizer and decreases $T_g$ more than shorter PEG chains (2 kDa).

TABLE 7

| Polymer | $1^{st}$ Transition (Tm for PEG) ° C.[a] | $2^{nd}$ Transition (Tg) ° C.[a] |
|---|---|---|
| P(HDFMA-co-MMA)-1 | — | 61.4 |
| P(HDFMA-co-MMA)-2 | — | 76.5 |
| ABC-1 (6720 g/mol) | 50.8 | 60.9 |
| ABC-2 (11390 g/mol) | 57.2 | 62.5 |
| NXL-$M_{ABC\text{-}1}$ | 50.9 | 60.7 |
| XL-$M_{ABC\text{-}1}$ | 47.5 | 79.1 |
| NXL-$M_{ABC\text{-}2}$ | 55.5 | 63.9 |
| XL-$M_{ABC\text{-}2}$ | 54.2 | 65.0 |

[a]Determined by Differential Scanning Calorimetry (DSC).

Example 6

This example demonstrates that PFP is encapsulated into nano-micelles.

Encapsulation of PFP was confirmed by comparison of empty and PFP encapsulated micelles size. FIG. 20 shows the size differences for ABC1 and 2 before and after encapsulation of 1% PFP. Empty micelles sizes are 149±19 and 213±17 nm and it increased to 324±39 and 333±42 nm for ABC-1 and ABC-2, respectively, after encapsulation of PFP. This clearly showed that PFP contributes to micelles size by occupying some space in the hydrophobic core. Moreover, our red blood cells ablation data (see below) showed that PFP is an essential component which lowers the threshold for mechanical ablation Example 7

This example demonstrates the effect of loaded % of PFP on micelles size and cavitation threshold.

We also investigate how increasing PFP amount effect micelles size. The idea behind of this experiment was increasing amount of PFP might increase the micelles size which will cause to decrease Laplace pressure and threshold of required pressure. FIG. 21 (panel A and B) shows that there is a trend for both copolymers that micelles size increases by increasing amount of encapsulated PFP. We tested 1 and 2 of PFP encapsulated micelles for cavitation to see whether there is significant decrease on threshold or not. Although both micelles have ability to cavitate at lower pressure, we could not observe any detectable pressure difference (FIG. 21C). However, bigger micelles can be failure passing through leaky vasculature of the cancer tissue.

Example 8

This example demonstrates the cytotoxicity of nano-droplets.

Cellular toxicity of micelles was tested using MTT assay. Prostate cancer cells were incubated 24 h with micelles solutions, and then typical MTT assay protocol was performed. In this protocol yellow MTT reagent (tetrazolium salt) is reduced to purple formazan in the mitochondria of living cells. This reduction takes place only when mitochondrial reductase enzymes are active, and therefore absorption of formazan dye at 570 nm directly relates to the number of viable (living) cells. FIG. 22 shows that cell viability is more than 90% for both micelles solutions which indicates both micelles solutions are not toxic at any level of concentration.

Example 9

The example examines the opsonization of nanodroplets.

Binding of nano-droplets to bovine serum albumin was studied by fluorescence quenching technique. Intrinsic fluorescence of tryptophan quenches when BSA interacts with substrate. 120 µM of micelles solution were mixed with 3 µM of BSA at 37° C. Excitation wavelength was determined as maximum wavelength of excitation scan ($\lambda_{ex}$: 284 nm) and emission spectrum was recorded in the range of 300-450 nm. BSA binding of G5 dendrimer and BSA solution were recorded under similar conditions to use as positive control and negative control, respectively. As can be seen in FIG. 23, G5 dendrimer interacts with BSA very quickly. Nono-droplets with PEG outer surface does not interact with BSA as quick as G5 dendrimer does which is expected since PEG increases biocompatibility and circulation time. Although this experiment has not completely finalized yet (micelles solutions need to be triplicates), our preliminary results (FIG. 23) shows that 2 KDa or 5 KDa PEG on the surface does not create significant difference because self-assembly of block copolymer creates a surface which is fully covered by PEG. It is well known that quenching of fluorescence of tryptophan increases by increasing concentration; we performed our experiment at relatively high concentration to see maximum interaction. We also believe micelles size may affect the binding.

Example 10

This example demonstrates the ablation of red blood cells.

Agarose gel phantoms with an embedded red blood cell (RBC) layer were used to demonstrate the ability of using micelles to mechanically ablate tissue. This tissue phantom has been previously utilized as a model to study the effectiveness of histotripsy fractionation and shown to correlate with tissue fractionation.[1] Briefly, degassed agarose gel (1.5% w/v agarose/saline) at 37° C. was mixed with related micelles solution or saline. A layer of these phantom mixtures were then poured into a rectangular polycarbonate housing to fill half of it and placed in a refrigerator at 4° C. to allow the agarose to solidify. A small amount of agarose solution was mixed with the RBCs (5% RBCs v/v) and applied as a thin layer top on the solidified agarose. After 5 min, the RBC-agarose layer was solidified, and the remaining agarose solution without RBCs was poured to completely fill the frame. This procedure created a thin layer of RBCs suspended in the center of the agarose phantom. (FIG. 24) The focus of a 32 element 500 kHz transducer was aligned with the center of the red blood cell phantom layer. Histotripsy pulses were applied at a pulse repetition frequency of 10 Hz at peak negative pressures of 12.5, 17, and 22 MPa to the center of phantoms containing red blood cell layer embedded with PFP encapsulated micelles, empty micelles, or saline. We observed cavitation at all pressure starting with 12.5 MPa for PFP encapsulated micelles. FIG. 25 shows a comparison of different micelles solutions and control experiments which they were exposed histotripsy pulses were applied at a pulse reputation frequency of 10 Hz at a peak negative pressure of 17 MPa (18 V). Phantom without micelles did not give us any cavitation. We observed really clear cavitation and damaged for phantom with PFP encapsulated micelles at this level of pressure. When it is compared with regular histotripsy treatment (50 HZ, 22 MPa pressure), the results clearly showed that nano-droplets significantly decrease the ablation threshold. Moreover, we compared PFP encapsulated micelles and empty micelles to investigate PFP's contribution to decrease the threshold. As can be seen in FIG. 25, PFP lowers cavitation threshold significantly by forming mechanically active nano-bubbles which can expands very quickly and eventually bursts by causing tissue damaged.

The Following List of References are Cited in Examples 3 to 10

1. Maxwell, A. D.; Wang, T. Y.; Yuan, L. Q.; Duryea, A. P.; Xu, Z.; Cain, C. A., A Tissue Phantom For Visualization And Measurement Of Ultrasound-Induced Cavitation Damage. *Ultrasound in Medicine and Biology* 2010, 36 (12), 2132-2143.
2. Haddleton, D. M.; Crossman, M. C.; Dana, B. H.; Duncalf, D. J.; Heming, A. M.; Kukulj, D.; Shooter, A. J., Atom transfer polymerization of methyl methacrylate mediated by alkylpyridylmethanimine type ligands, copper(I) bromide, and alkyl halides in hydrocarbon solution. *Macromolecules* 1999, 32 (7), 2110-2119.
3. Durmaz, H.; Dag, A.; Altintas, O.; Erdogan, T.; Hizal, G.; Tunca, U., One-pot synthesis of ABC type triblock copolymers via in situ click 3+2 and Diels-Alder 4+2 reactions. *Macromolecules* 2007, 40 (2), 191-198.
4. Mantovani, G.; Lecolley, F.; Tao, L.; Haddleton, D. M.; Clerx, J.; Cornelissen, J.; Velonia, K., Design and synthesis of N-maleimido-functionalized hydrophilic polymers via copper-mediated living radical polymerization: A suitable alternative to PEGylation chemistry. *Journal of the American Chemical Society* 2005, 127 (9), 2966-2973.

The Following List of References are Cited Throughout The Background and Examples 1 and 2.

1 Howlader, N. et al. (National Cancer Institute, Bethesda, 2011).
2 Hugosson, J., Stranne, J. & Carlsson, S. V. Radical retropubic prostatectomy: A review of outcomes and side-effects. *Acta Oncologica* 50 Suppl 1, 92-97, doi:doi:10.3109/0284186X.2010.535848 (2011).
3 Underwood, W. et al. Racial treatment trends in localized/regional prostate carcinoma: 1992-1999. *Cancer* 103, 538-545, doi:10.1002/cncr.20796 (2005).
4 Bill-Axelson, A. et al. Radical prostatectomy versus watchful waiting in early prostate cancer. *N Engl J Med* 352, 1977-1984, doi:10.1056/NEJMoa043739 (2005).
5 Cooperberg, M. R. et al. The contemporary management of prostate cancer in the United States: lessons from the cancer of the prostate strategic urologic research endeavor (CapSURE), a national disease registry. *The Journal of urology* 171, 1393-1401, doi:10.1097/01.ju.0000107247.81471.06 (2004).

6 Klein, E. A. et al. Surgeon Experience is Strongly Associated With Biochemical Recurrence After Radical Prostatectomy for All Preoperative Risk Categories. *The Journal of urology* 179, 2212-2217, doi:10.1016/j.juro.2008.01.107 (2008).

7 Cookson, M. S. et al. Variation in the Definition of Biochemical Recurrence in Patients Treated for Localized Prostate Cancer: The American Urological Association Prostate Guidelines for Localized Prostate Cancer Update Panel Report and Recommendations for a Standard in the Reporting of Surgical Outcomes. *The Journal of Urology* 177, 540-545, doi:10.1016/j.juro.2006.10.097 (2007).

8 Swanson, G. P., Riggs, M. & Hermans, M. Pathologic findings at radical prostatectomy: Risk factors for failure and death. *Urol Oncol* 25, 110-114 (2007).

9 Vis, A. N., Schroder, F. H. & Kwast, T. H. v. d. The actual value of the surgical margin status as a predictor of disease progression in men with early prostate cancer. *European Urology* 50, 258-265 (2006).

10 Dahl, D. M., He, W., Lazarus, R., McDougal, W. S. & Wu, C.-L. Pathologic outcome of laparoscopic and open radical prostatectomy. *Urology* 68, 1253-1256, doi:10.1016/j.urology.2006.08.1054 (2006).

11 Katz, M. S. et al. Predictors of biochemical outcome with salvage conformal radiotherapy after radical prostatectomy for prostate cancer. *Journal of Clinical Oncology* 21, 483-489 (2003).

12 Roehl, K. A., Han, M., Ramos, C. G., Antenor, J. A. & Catalona, W. J. Cancer progression and survival rates following anatomical radical retropubic prostatectomy in 3,478 consecutive patients: long-term results. The Journal of urology 172, 910-914, doi:10.1097/01.ju.0000134888.22332.bb (2004).

13 Freedland, S. J. et al. Risk of prostate cancer-specific mortality following biochemical recurrence after radical prostatectomy. *The Journal of the American Medical Association* 294, 433-439, doi:10.1001/jama.294.4.433 (2005).

14 Raldow, A., Hamstra, D. A., Kim, S. & Yu, J. B. Salvage external beam radiotherapy for prostate cancer after radical prostatectomy: current status and controversy. *Oncology (Williston Park)* 24, 692-700, 702 (2010).

15 Stephenson, A. J. et al. Predicting the outcome of salvage radiation therapy for recurrent prostate cancer after radical prostatectomy. *Journal of clinical oncology* 25, 2035-2041, doi:10.1200/JCO.2006.08.9607 (2007).

16 Trock, B. J. et al. Prostate cancer-specific survival following salvage radiotherapy vs. observation in men with biochemical recurrence after radical prostatectomy. *The journal of the American Medical Association* 299, 2760-2769, doi:10.1001/jama.299.23.2760 (2008).

17 Pound, C. R. et al. Natural history of progression after PSA elevation following radical prostatectomy. *The Journal of the American Medical Association* 281, 1591-1597 (1999).

18 Poortmans, P. et al. Guidelines for target volume definition in post-operative radiotherapy for prostate cancer, on behalf of the EORTC Radiation Oncology Group. *Radiotherapy and oncology: journal of the European Society for Therapeutic Radiology and Oncology* 84, 121-127, doi:10.1016/j.radonc.2007.07.017 (2007).

19 Michalski, J. M. et al. Development of RTOG consensus guidelines for the definition of the clinical target volume for postoperative conformal radiation therapy for prostate cancer. *International journal of radiation oncology, biology, physics* 76, 361-368, doi:10.1016/j.ijrobp.2009.02.006 (2010).

20 Wiltshire, K. L. et al. Anatomic boundaries of the clinical target volume (prostate bed) after radical prostatectomy. *International journal of radiation oncology, biology, physics* 69, 1090-1099, doi:10.1016/j.ijrobp.2007.04.068 (2007).

21 Bolla, M. et al. Postoperative radiotherapy after radical prostatectomy: a randomised controlled trial (EORTC trial 22911). *Lancet* 366, 572-578, doi:10.1016/S0140-6736(05)67101-2 (2005).

22 Thompson, I. M. et al. Adjuvant radiotherapy for pathological T3N0M0 prostate cancer significantly reduces risk of metastases and improves survival: long-term follow up of a randomized clinical trial. *The Journal of urology* 181, 956-962, doi:10.1016/j.juro.2008.11.032 (2009).

23 Wiegel, T. et al. Phase III postoperative adjuvant radiotherapy after radical prostatectomy compared with radical prostatectomy alone in pT3 prostate cancer with postoperative undetectable prostate-specific antigen: ARO 96-02/AUO AP 09/95. *Journal of Clinical Oncology* 27, 2924-2930, doi:10.1200/JCO.2008.18.9563 (2009).

24 Moinpour, C. M. et al. Health-Related Quality of Life Results in Pathologic Stage C Prostate Cancer From a Southwest Oncology Group Trial Comparing Radical Prostatectomy Alone With Radical Prostatectomy Plus Radiation Therapy. *Journal of Clinical Oncology* 26, 112-120, doi:10.1200/jco.2006.10.4505 (2008).

25 Bolla, M. et al. Postoperative radiotherapy after radical prostatectomy: a randomised controlled trial (EORTC trial 22911). *The Lancet* 366, 572-578, doi:10.1016/s0140-6736(05)67101-2 (2005).

26 Miller, D. C. et al. Long-Term Outcomes Among Localized Prostate Cancer Survivors: Health-Related Quality-of-Life Changes After Radical Prostatectomy, External Radiation, and Brachytherapy. *Journal of Clinical Oncology* 23, 2772-2780, doi:10.1200/jco.2005.07.116 (2005).

27 van der Wielen, G. J., Mulhall, J. P. & Incrocci, L. Erectile dysfunction after radiotherapy for prostate cancer and radiation dose to the penile structures: A critical review. *Radiotherapy and Oncology* 84, 107-113, doi:10.1016/j.radonc.2007.07.018 (2007).

28 Hu, J. C., Elkin, E. P., Krupski, T. L., Gore, J. & Litwin, M. S. The effect of postprostatectomy external beam radiotherapy on quality of life. *Cancer* 107, 281-288, doi:10.1002/cncr.21980 (2006).

29 Kripfgans, O. D., Fowlkes, J. B., Miller, D. L., Eldevik, O. P. & Carson, P. L. Acoustic droplet vaporization for therapeutic and diagnostic applications. *Ultrasound in Med. & Biol.* 26 (2000).

30 Forsberg, F., Merton, D. A., Liu, J. B., Needleman, L. & Goldberg, B. B. Clinical applications of ultrasound contrast agents. *Ultrasonics* 36, [d]695-701 (1998).

31 Deshpande, N., Needles, A. & Willmann, J. K. Molecular ultrasound imaging: current status and future directions. *Clin Radiol.* 65, 567-581. (2010).

32 Balogh, L. et al. Significant effect of size on the in vivo biodistribution of gold composite nanodevices in mouse tumor models. *Nanomedicine: Nanotechnology, Biology and Medicine* 3, 281-296, doi:10.1016/j.nano.2007.09.001 (2007).

33 Danquah, M., Li, F., Duke, C., Miller, D. & Mahato, R. Micellar Delivery of Bicalutamide and Embelin for Treating Prostate Cancer. *Pharmaceutical Research* 26, 2081-2092, doi:10.1007/s11095-009-9903-5 (2009).

34 Gebhart, C. L. et al. Design and Formulation of Polyplexes Based on Pluronic-Polyethyleneimine Conjugates for Gene Transfer. *Bioconjugate Chemistry* 13, 937-944, doi: 10.1021/bc025504w (2002).

35 Fang, J., Sawa, T. & Maeda, H. Factors and mechanism of "EPR" effect and the enhanced antitumor effects of macromolecular drugs including SMANCS. *Advances in Experimental Medicine and Biology* 519, 29-49 (2003).
36. Greish, K., Fang, J., Inutsuka, T., Nagamitsu, A. & Maeda, H. Macromolecular therapeutics: advantages and prospects with special emphasis on solid tumour targeting. *Clinical Pharmacokinetics* 42, 1089-1105 (2003).
37. Iyer, A. K., Khaled, G., Fang, J. & Maeda, H. Exploiting the enhanced permeability and retention effect for tumor targeting. *Drug Discovery Today* 11, 812-818 (2006).
38. Maeda, H. & Matsumura, Y. Tumoritropic and lymphotropic principles of macromolecular drugs. *Critical Reviews in Therapeutic Drug Carrier Systems* 6, 193-210 (1989).
39. Maeda, H., Noguchi, Y., Sato, K. & Akaike, T. Enhanced vascular permeability in solid tumor is mediated by nitric oxide and inhibited by both new nitric oxide scavenger and nitric oxide synthase inhibitor. *Japanese Journal of Cancer Research* 85, 331-334 (1994).
40. Okuda, T. et al. PEGylated lysine dendrimers for tumor-selective targeting after intravenous injection in tumor-bearing mice. *Journal of Controlled Release* 116, 330-336 (2006).
41. Yu, J. J. et al. Bio-distribution and anti-tumor efficacy of PEG/PLA nano particles loaded doxorubicin. *Journal of Drug Targeting* 15, 279-284 (2007).
42. Casciani, E. et al. Endorectal and Dynamic Contrast-Enhanced MRI for Detection of Local Recurrence After Radical Prostatectomy. *American Journal of Roentgenology* 190, 1187-1192, doi:10.2214/ajr.07.3032 (2008).
43. Haider, M. A. et al. Dynamic Contrast-Enhanced Magnetic Resonance Imaging for Localization of Recurrent Prostate Cancer After External Beam Radiotherapy. *International Journal of Radiation Oncology*Biology*Physics* 70, 425-430, doi:10.1016/j.ijrobp.2007.06.029 (2008).
44. Rouvière, O. et al. Recurrent prostate cancer after external beam radiotherapy: value of contrast-enhanced dynamic MRI in localizing intraprostatic tumor—correlation with biopsy findings. *Urology* 63, 922-927, doi:10.1016/j.urology.2003.12.017 (2004).
45. Yakar, D. et al. Feasibility of 3T Dynamic Contrast-Enhanced Magnetic Resonance-Guided Biopsy in Localizing Local Recurrence of Prostate Cancer After External Beam Radiation Therapy. *Investigative Radiology* 45, 121-125 (2010).
46. Moman, M. R. et al. Focal Salvage Guided by T2-Weighted and Dynamic Contrast-Enhanced Magnetic Resonance Imaging for Prostate Cancer Recurrences. *International Journal of Radiation Oncology*Biology*Physics* 76, 741-746, doi:10.1016/j.ijrobp.2009.02.055 (2010).
47. Akhtar, N. H., Pail, O., Saran, A., Tyrell, L. & Tagawa, S. T. Prostate-specific membrane antigen-based therapeutics. *Advances in Urology* 2012 (2011).
48. Nakajima, T. et al. Targeted, Activatable, In Vivo Fluorescence Imaging of Prostate-Specific Membrane Antigen (PSMA) Positive Tumors Using the Quenched Humanized J591 Antibody-Indocyanine Green (ICG) Conjugate. *Bioconjugate Chemistry* 22, 1700-1705, doi:10.1021/bc2002715 (2011).
49. Li, Y., Tian, Z., Rizvi, S. M. A., Bander, N. H. & Allen, B. J. In vitro and preclinical targeted alpha therapy of human prostate cancer with Bi-213 labeled J591 antibody against the prostate specific membrane antigen. *Prostate Cancer and Prostatic Diseases* 5, 36-46 (2002).
50. Xu, Z., Fowlkes, J. B., Rothman, E. D., Levin, A. M. & Cain, C. A. Controlled ultrasound tissue erosion: the role of dynamic interaction between insonation and microbubble activity. *J. Acoust. Soc. Am.* 117, 424-435 (2005).
51. Xu, Z., Fowlkes, J. B. & Cain, C. A. A new strategy to enhance cavitational tissue erosion by using a high intensity initiating sequence. *IEEE Trans Ultrasonics Ferroelectrics Freq Control* 53, 1412-1424 (2006).
52. Kieran, K. et al. Refining histotripsy: defining the parameter space for the creation of nonthermal lesions with high intensity, pulsed focused ultrasound of the in vitro kidney. *J Urol* 178, 672-676 (2007).
53. Xu, Z., Hall, T. L., Fowlkes, J. B. & Cain, C. A. Optical and acoustic monitoring of bubble cloud dynamics at a tissue-fluid interface in ultrasound tissue erosion. *J. Acoust. Soc. Am.* 121, 2421-2430 (2007).
54. Xu, Z. et al. Evolution of bubble clouds produced in pulsed cavitational ultrasound therapy—histotripsy. *IEEE Trans Ultrason Ferroelectr Freq Control.* 55, 1122-1132 (2008).
55. Xu, Z. et al. High Speed Imaging of Bubble Clouds Generated in Pulsed Ultrasound Cavitational Therapy—Histotripsy. *IEEE Trans Ultrasonics Ferroelectrics Freq Control* 54, 2091-2101 (2007).
56. Parsons, J. E., Cain, C. A., Abrams, G. D. & Fowlkes, J. B. Pulsed cavitational ultrasound therapy for controlled tissue homogenization. *Ultrasound Med. Biol.* 32, 115-129 (2006).
57. Roberts, W. W. et al. Pulsed cavitational ultrasound: a noninvasive technology for controlled tissue ablation (histotripsy) in the rabbit kidney. *Journal of Urology* 175, 734-738 (2006).
58. Lake, A. M. et al. Histotripsy: minimally invasive technology for prostatic tissue ablation in an in vivo canine model. *Urology.* 72, 682-686. (2008).
59. Trevena, D. H. Cavitation and the generation of tension in liquids. *Journal of Physics D (Applied Physics)* 17, 2139-2164 (1984).
60. Rapoport, N., Gao, Z. & Kennedy, A. Multifunctional nanoparticles for combining ultrasonic tumor imaging and targeted chemotherapy. *J Natl Cancer Inst.* 99, 1095-1106. Epub 2007 July 1010. (2007).
61. Ferrara, K. W., Borden, M. A. & Zhang, H. Lipid-shelled vehicles: engineering for ultrasound molecular imaging and drug delivery. *Acc Chem. Res.* 42, 881-892. (2009).
62. Phillips, D. et al. Acoustic backscatter properties of the particle/bubble ultrasound contrast agent. *Ultrasonics* 36, 883-892. (1998).
63. Wheatley, M. A. & Lewandowski, J. Nano-sized ultrasound contrast agent: salting-out method. *Mol. Imaging.* 9, 96-107. (2010).
64. Uesugi, Y., Kawata, H., Jo, J., Saito, Y. & Tabata, Y. An ultrasound-responsive nano delivery system of tissue-type plasminogen activator for thrombolytic therapy. *J Control Release.* 147, 269-277. Epub 2010 August 2016. (2010).
65. Oeffinger, B. E. & Wheatley, M. A. Development and characterization of a nano-scale contrast agent. *Ultrasonics* 42, 343-347. (2004).
66. Hadinoto, K. Mechanical stability of hollow spherical nano-aggregates as ultrasound contrast agent. *Int J. Pharm.* 374, 153-161. Epub 2009 March 2024. (2009).
67. Néstor, M.-M. et al. Preparation and in vitro evaluation of poly(d,l-lactide-co-glycolide) air-filled nanocapsules as a contrast agent for ultrasound imaging. *Ultrasonics* 51, 839-845, doi:10.1016/j.ultras.2011.04.003 (2011).
68. Marmottant, P., Bouakaz, A., Jong, N. d. & Quilliet, C. Buckling resistance of solid shell bubbles under ultrasound. *Journal of the Acoustical Society of America* 129, 1231-1239 (2011).
69. Grishenkov, D., Kari, L., Brodin, L.-A., Brismar, T. B. & Paradossi, G. In vitro contrast-enhanced ultrasound measurements of capillary microcirculation: Comparison between polymer- and phospholipid-shelled microbubbles. *Ultrasonics* 51, 40-48, doi:10.1016/j.ultras.2010.05.006 (2011).
70 Xing, Z. et al. Novel ultrasound contrast agent based on microbubbles generated from surfactant mixtures of Span 60 and polyoxyethylene 40 stearate. *Acta Biomaterialia* 6, 3542-3549, doi:10.1016/j.actbio.2010.03.007 (2010).
71 Eisenbrey, J. R. et al. Development and optimization of a doxorubicin loaded poly(lactic acid) contrast agent for ultrasound directed drug delivery. *Journal of Controlled Release* 143, 38-44, doi:10.1016/j.jconrel.2009.12.021 (2010).
72 Krupka, T. M. et al. Formulation and Characterization of Echogenic Lipid-Pluronic Nanobubbles. *Molecular Pharmaceutics* 7, 49-59, doi:10.1021/mp9001816 (2009).
73 Díaz-López, R. et al. The performance of PEGylated nanocapsules of perfluorooctyl bromide as an ultrasound contrast agent. *Biomaterials* 31, 1723-1731, doi:10.1016/j.biomaterials.2009.11.044 (2010).
74 Hadinoto, K. & Cheow, W. S. Hollow spherical nanoparticulate aggregates as potential ultrasound contrast agent: shell thickness characterization. *Drug Development and Industrial Pharmacy* 35, 1167-1179, doi:doi:10.1080/03639040902824845 (2009).
75 Hadinoto, K. Mechanical stability of hollow spherical nano-aggregates as ultrasound contrast agent. *Int J Pharm* 374, 153-161, doi:10.1016/j.ijpharm.2009.03.017 (2009).
76 Grishenkov, D., Pecorari, C., Brismar, T. B. & Paradossi, G. Characterization of Acoustic Properties of PVA-Shelled Ultrasound Contrast Agents: Ultrasound-Induced Fracture (Part II). *Ultrasound Med Biol* 35, 1139-1147, doi:10.1016/j.ultrasmedbio.2009.03.006 (2009).
77 Grishenkov, D., Pecorari, C., Brismar, T. B. & Paradossi, G. Characterization of Acoustic Properties of PVA-Shelled Ultrasound Contrast Agents: Linear Properties (Part I). *Ultrasound Med Biol* 35, 1127-1138, doi:10.1016/j.ultrasmedbio.2009.02.002 (2009).
78 Pisani, E. et al. Surfactant dependent morphology of polymeric capsules of perfluorooctyl bromide: Influence of polymer adsorption at the dichloromethane-water interface. *Journal of Colloid and Interface Science* 326, 66-71, doi:10.1016/j.jcis.2008.07.013 (2008).
79 Díaz-López, R. et al. Phospholipid decoration of microcapsules containing perfluorooctyl bromide used as ultrasound contrast agents. *Biomaterials* 30, 1462-1472, doi:10.1016/j.biomaterials.2008.11.032 (2009).
80 Liu, Y., Miyoshi, H. & Nakamura, M. Encapsulated ultrasound microbubbles: Therapeutic application in drug/gene delivery. *Journal of Controlled Release* 114, 89-99 (2006).
81 Soman, N. R., Lanza, G. M., Heuser, J. M., Schlesinger, P. H. & Wickline, S. A. Synthesis and characterization of stable fluorocarbon nanostructures as drug delivery vehicles for cytolytic peptides. *Nano Letters* 8, 1131-1136 (2008).
82 Rapoport, N., Gao, Z. & Kennedy, A. Multifunctional nanoparticles for combining ultrasonic tumor imaging and targeted chemotherapy. *J Natl Cancer Inst* 99, 1095-1106, doi:10.1093/jnci/djm043 (2007).
83 Kandadai, M. A. et al. Comparison of Surfactants Used to Prepare Aqueous Perfluoropentane Emulsions for Pharmaceutical Applications. *Langmuir* 26, 4655-4660, doi:10.1021/la100307r (2010).
84 Du, L., Jin, Y., Zhou, W. & Zhao, J. Ultrasound-Triggered Drug Release and Enhanced Anticancer Effect of Doxorubicin-Loaded Poly(D,L-Lactide-Co-Glycolide)-Methoxy-Poly(Ethylene Glycol) Nanodroplets. *Ultrasound Med Biol* 37, 1252-1258, doi:10.1016/j.ultrasmedbio.2011.05.012 (2011).
85 Ferrara, K. W., Borden, M. A. & Zhang, H. Lipid-shelled vehicles: engineering for ultrasound molecular imaging and drug delivery. *Acc Chem Res* 42, 881-892, doi:10.1021/ar8002442 (2009).
86 Dindyal, S. & Kyriakides, C. Ultrasound microbubble contrast and current clinical applications. *Recent Pat Cardiovasc Drug Discov* 6, 27-41 (2011).
87 Forsberg, F., Merton, D. A., Liu, J. B., Needleman, L. & Goldberg, B. B. Clinical applications of ultrasound contrast agents. *Ultrasonics* 36, 695-701 (1998).
88 Lindner, J. R. Evolving applications for contrast ultrasound. *Am J Cardiol* 90, 72J-80J (2002).
89 Platts, D. G. & Fraser, J. F. Contrast echocardiography in critical care: echoes of the future? A review of the role of microsphere contrast echocardiography. *Crit. Care Resusc* 13, 44-55 (2011).
90 Bartczak, D. & Kanaras, A. G. Preparation of Peptide-Functionalized Gold Nanoparticles Using One Pot EDC/Sulfo-NHS Coupling. *Langmuir* 27, 10119-10123, doi:10.1021/la2022177 (2011).
91 Wildling, L. et al. Linking of Sensor Molecules with Amino Groups to Amino-Functionalized AFM Tips. *Bioconjugate Chemistry* 22, 1239-1248, doi:10.1021/bc200099t (2011).
92 Nam, K., Kimura, T. & Kishida, A. Controlling Coupling Reaction of EDC and NHS for Preparation of Collagen Gels Using Ethanol/Water Co-Solvents. *Macromolecular Bioscience* 8, 32-37, doi:10.1002/mabi.200700206 (2008).
93 Zheng, J. N. et al. Chitosan-g-MPEG-Modified Alginate/Chitosan Hydrogel Microcapsules: A Quantitative Study of the Effect of Polymer Architecture on the Resistance to Protein Adsorption. *Langmuir* 26, 17156-17164, doi:10.1021/la1030203 (2010).
94 Gref, R. et al. "Stealth" corona-core nanoparticles surface modified by polyethylene glycol (PEG): influences of the corona (PEG chain length and surface density) and of the core composition on phagocytic uptake and plasma protein adsorption. *Colloids and Surfaces B: Biointerfaces* 18, 301-313, doi:10.1016/s0927-7765(99)00156-3 (2000).
95 Dhar, S., Kolishetti, N., Lippard, S. J. & Farokhzad, O. C. Targeted delivery of a cisplatin prodrug for safer and more effective prostate cancer therapy in vivo. *Proceedings of the National Academy of Sciences* 108, 1850-1855, doi:10.1073/pnas.1011379108 (2011).
96 Li, F., Danquah, M. & Mahato, R. I. Synthesis and Characterization of Amphiphilic Lipopolymers for Micellar Drug Delivery. *Biomacromolecules* 11, 2610-2620, doi:10.1021/bm100561v (2010).
97 Guo, J. et al. Aptamer-functionalized PEG-PLGA nanoparticles for enhanced anti-glioma drug delivery. *Biomaterials* 32, 8010-8020, doi:10.1016/j.biomaterials.2011.07.004 (2011).
98 Yu, H., Nie, Y., Dohmen, C., Li, Y. & Wagner, E. Epidermal Growth Factor-PEG Functionalized PAMAM-Pentaethylenehexamine Dendron for Targeted Gene Delivery Produced by Click Chemistry. *Biomacromolecules* 12, 2039-2047, doi:10.1021/bm101464n (2011).
99 Rajender Reddy, K., Modi, M. W. & Pedder, S. Use of peginterferon alfa-2a (40 KD) (Pegasys®) for the treatment of hepatitis C. *Advanced Drug Delivery Reviews* 54, 571-586, doi:10.1016/s0169-409x(02)00028-5 (2002).

100 Abuchowski, A. et al. Cancer therapy with chemically modified enzymes. I. Antitumor properties of polyethylene glycol-asparaginase conjugates. *Cancer Biochem Biophys.* 7, 175-186 (1984).

101 Chen, Y.-X., Triola, G. & Waldmann, H. Bioorthogonal Chemistry for Site-Specific Labeling and Surface Immobilization of Proteins. *Acc Chem Res*, null-null, doi:10.1021/ar200046h (2011).

102 Nimmo, C. M., Owen, S. C. & Shoichet, M. S. Diels-Alder Click Cross-Linked Hyaluronic Acid Hydrogels for Tissue Engineering. *Biomacromolecules* 12, 824-830, doi:10.1021/bm101446k (2011).

103 Franc, G. & Kakkar, A. K. Diels-Alder "Click" Chemistry in Designing Dendritic Macromolecules. *Chemistry—A European Journal* 15, 5630-5639, doi:10.1002/chem.200900252 (2009).

104 Sletten, E. M. & Bertozzi, C. R. From Mechanism to Mouse: A Tale of Two Bioorthogonal Reactions. *Acc Chem Res*, null-null, doi:10.1021/ar200148z (2011).

105 Qi, J., Han, M.-S., Chang, Y.-C. & Tung, C.-H. Developing Visible Fluorogenic 'Click-On' Dyes for Cellular Imaging. *Bioconjugate Chemistry*, null-null, doi:10.1021/bc200282t (2011).

106 Chen, J., Liu, M., Chen, C., Gong, H. & Gao, C. Synthesis and Characterization of Silica Nanoparticles with Well-Defined Thermoresponsive PNIPAM via a Combination of RAFT and Click Chemistry. *ACS Applied Materials & Interfaces*, null-null, doi:10.1021/am2007189 (2011).

107 Grabski, B. et al. Computerized transrectal ultrasound of the prostate in a multicenter setup (C-TRUS-MS): detection of cancer after multiple negative systematic random and in primary biopsies. *World Journal of Urology*, 1-7, doi:10.1007/s00345-011-0713-0.

108 Wang, T. Y. et al. Active focal zone sharpening for high-precision treatment using histotripsy. *IEEE Trans Ultrason Ferroelectr Freq Control.* 58, 305-315. (2011).

109 Lin, Y.-L., Jiang, G., Birrell, L. & El-Sayed, M. E. H. Degradable, pH-sensitive, membrane-destabilizing, comb-like polymers for intracellular delivery of nucleic acids. *Biomaterials* 31, 7150-7166 (2010).

110 AIUM. Acoustic Output Labeling Standard for Diagnostic Ultrasound Equipment: A Standard for How Manufacturers Should Specify Acoustic Output Data, Revision 1. (Laurel, Md., American Institute of Ultrasound in Medicine, 2008).

111 Bander, N. H. et al. Targeted systemic therapy of prostate cancer With a monoclonal antibody to prostate-specific membrane antigen. *Seminars in Oncology* 30, 667-677 (2003).

112 O'Donoghue, J. A., Bardies, M. & Wheldon, T. E. Relationships between tumor size and curablity for uniformly targeted therapy with beta-emitting radionuclides. *Journal Name Journal of Nuclear Medicine; Journal Volume:* 36; *Journal Issue:* 10; *Other Information: PBD: October* 1995, Medium: X; Size: pp. 1902-1909 (1995).

113 DeNardo, G. L., Schlom, J., Buchsbaum, D. J. & al., e. Rationales, evidence, and design considerations for fractionated radioimmunotherapy. *Cancer* 94, 1332-1348 (2002).

114 Tagawa, S. T., Milowsky, M. I. & al., M. M. e. Phase II trial of 177Lutetium radiolabeled anti-prostate-specific membrane antigen (PSMA) monoclonal antibody J591 (177Lu-J591) in patients (pts) with metastatic castrate-resistant prostate cancer (metCRPC). *Journal of Clinical Oncology* 26, 284s (2008).

115 Tagawa, S. T., Vallabhajosula, S. & Osborne, J. Phase I trial of fractionated-dose 177lutetium radiolabeled anti-prostate specific membrane antigen (PSMA) monoclonal antibody J591 (177Lu-J591) in patients (pts) with metastatic castration resistant prostate cancer (metCRPC). *Journal of Clinical Oncology* 28, Abstract no. 4667 (2010).

116 Gao, X., Cui, Y., Levenson, R. M., Chung, L. W. K. & Nie, S. In vivo cancer targeting and imaging with semiconductor quantum dots. *Nat Biotech* 22, 969-976, doi:http//www.nature.com/nbt/journal/v22/n8/suppinfo/nbl994S1.htm; (2004).

117 Min, K. et al. Dual-aptamer-based delivery vehicle of doxorubicin to both PSMA (+) and PSMA (−) prostate cancers. *Biomaterials* 32, 2124-2132, doi:10.1016/j.biomaterials.2010.11.035 (2011).

118 Teesalua, T., Sugaharaa, K. N., Kotamrajua, V. R. & Ruoslahtia, E. C-end rule peptides mediate neuropilin-1-dependent cell, vascular, and tissue penetration. *Proceedings of the National Academy of Science* 106, 16157-16162.

119 Grainger, S. J. et al. Pulsed Ultrasound Enhances Nanoparticle Penetration into Breast Cancer Spheroids. *Molecular Pharmaceutics* 7, 2006-2019, doi:10.1021/mp100280b (2010).

120 Borcard, F. o. et al. Covalent Cell Surface Functionalization of Human Fetal Osteoblasts for Tissue Engineering. *Bioconjugate Chemistry* 22, 1422-1432, doi:10.1021/bc200147m (2011).

121 Hsiao, A. Y. et al. Microfluidic system for formation of PC-3 prostate cancer co-culture spheroids. *Biomaterials* 30, 3020-3027, doi:10.1016/j.biomaterials.2009.02.047 (2009).

122 Fu, Z. et al. Metastasis suppressor gene Raf kinase inhibitor protein (RKIP) is a novel prognostic marker in prostate cancer. *Prostate* 66, 248-256 (2006).

123 COMSTOCK, K. E. et al. A Bioluminescent Orthotopic Mouse Model of Human Osteosarcoma that Allows Sensitive and Rapid Evaluation of New Therapeutic Agents In Vivo. *In Vivo* 23, 661-668 (2009).

124 Zhang, J. et al. In vivo real-time imaging of TGF-beta-induced transcriptional activation of the RANK ligand gene promoter in intraosseous prostate cancer. *Prostate* 59, 360-369 (2004).

125 Heneweer, C., Holland, J. P., Divilov, V., Carlin, S. & Lewis, J. S. Magnitude of Enhanced Permeability and Retention Effect in Tumors with Different Phenotypes: 89Zr-Albumin as a Model System. *Journal of Nuclear Medicine* 52, 625-633, doi:10.2967/jnumed.110.083998 (2011).

126 Saar, M. et al. Experimental orthotopic prostate tumor in nude mice: Techniques for local cell inoculation and three-dimensional ultrasound monitoring[star, open]. *Urologic Oncology Seminars and Original Investigations* In Press, Corrected Proof, doi:10.1016/j.urolonc.2010.02.014.

127 Hall, T. L. et al. Histotripsy of the prostate: dose effects in a chronic canine model. *Urology.* 74, 932-937. (2009).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A nanobubble comprising an amphiphilic ABC triblock copolymer, wherein:
   block A comprises a hydrophilic polymer,
   block B comprises a crosslinking polymer, and
   block C comprises a hydrophobic copolymer comprising methyl methacrylate (MMA) and
   a fluorinated monomer,
      wherein the fluorinated monomer is present in the hydrophobic copolymer of block C at 25 mole percent or less, wherein the hydrophobic copolymer has a number average molecular weight of about 3 kDa to about 12.5 kDa,
      or a nanobubble produced from micellization of the amphiphillic ABC triblock copolymer.

2. The nanobubble of claim 1, wherein the hydrophilic polymer of block A (a) comprises an amphiphilic group selected from the group consisting of: ethylene oxide, carboxylic acid, hydroxyl, and a quaternized amine group, optionally, wherein the hydrophilic polymer of block A is selected from the group consisting of: polyethylene glycol (PEG), poly(trimethyl ethyl methacrylate), poly(acrylic acid), and poly (N-2-hydroxy propyl)methacrylamide (PHPMA), and/or (c) has a number average molecular weight of about 1 kDa to about 6 kDa or about 1 kDa to about 5 kDa or about 2 kDa or 5 kDa, (b) has a number average molecular weight of about 1 kDa to about 6 kDa, optionally, about 1 kDa to about 5 kDa or about 2 kDa or 5 kDa.

3. The nanobubble of claim 1, wherein the crosslinking polymer of block B is polyacrylic acid (PAA), poly(hydroxyl ethyl acrylate) (PHEA), or polypentafluoropheyl acrylate (PPFPA), optionally, wherein the crosslinking polymer has a number average molecular weight of about 1 kDa to about 5 kDa or about 0.5 kDa to about 3 kDa.

4. The nanobubble of claim 1, wherein the fluorinated monomer comprises a fluorinated alkyl chain or a fluorinated lipid chain, optionally, wherein (a) the fluorinated alkyl chain comprises a chain of n carbon atoms, wherein n is 8 to 20, and wherein up to m carbon atoms are completely fluorinated, wherein m=n−2 or (b) the number of fluorine atoms per unit of hydrophobic copolymer is between about 60 and about 255.

5. The nanobubble of claim 1, wherein the fluorinated monomer is hexadecafluorodecylmethacrylate (HDFMA), 3,3,4,4,5,5,6,6,7,7,8,8,9,9,10,10,10-Heptadecafluorodecyl methacrylate, 1H,1H,2H,2H-perfluorooctyl methacrylate, or 2,2,2-Trifluoroethyl methacrylate, optionally, wherein the fluorinated monomer is HDFMA and the block C comprises a hydrophobic random copolymer comprising MMA and HDFMA.

6. The nanobubble of claim 1, wherein the hydrophilic polymer of block A is PEG, the crosslinking polymer of block B is PAA, and the hydrophobic copolymer of block C is a hydrophobic random copolymer comprising MMA and HDFMA, optionally, wherein the amphiphilic ABC triblock copolymer has a number average molecular weight of about 6.7 kDa to about 19.1 kDa.

7. The nanobubble of claim 1, wherein a targeting ligand is attached to a tip of the hydrophilic polymer of block A, optionally, wherein (a) at least 10% of the hydrophilic polymer of block A is attached at its tip to a targeting ligand, (b) the targeting ligand is a cancer cell-targeting ligand, and/or (c) the targeting ligand is an aptamer or an antibody, or an antigen binding fragment thereof.

8. The nanobubble of claim 1 comprising a hydrophilic brush, a shell, and a core, wherein the hydrophilic brush comprises block A of the triblock copolymer, shell comprises block B of the triblock copolymer and the core comprises block C of the triblock copolymer, optionally, wherein the shell is cross-linked.

9. The nanobubble of claim 1, comprising a core comprising an ultrasound contrast agent, optionally, wherein the ultrasound contrast agent (a) has a boiling point which is greater than about 25° C., (b) is selected from the group consisting of: perfluorocarbon (PFC), perfluoropentane (PFP), perfluoropropane, perfluorobutane, and perfluorohexane, and/or (c) is present in the nanobubble at a loaded % between about 0.5% and about 3%.

10. The nanobubble of claim 1, comprising a core coated with an oil, optionally, wherein the oil comprises a therapeutic agent.

11. The nanobubble of claim 1, wherein the nanobubble (i) has an average diameter less than 700 nm at about 37° C., (ii) is toxic to not more than 10% of a population of cells when incubated with the population of cells in an MTT assay, in the absence of ultrasound pulses, and/or (iii) undergoes cavitation when exposed to ultrasound pulses with peak negative pressures of 7 MPa to 25 MPa.

12. A method of treating cancer in a subject, comprising the steps of administering to the subject a nanobubble of claim 1 and ultrasound, in an amount effective to treat the cancer in the subject.

13. A method of determining the presence of a cancer cell in a subject, comprising the steps of administering to the subject (i) a nanobubble of claim 1, wherein the nanobubble comprises (a) a cancer cell-targeting ligand which binds to a marker of the cancer cell and (b) an ultrasound contrast agent, and (ii) ultrasound.

14. A nanobubble of claim 1, comprising an ultrasound contrast agent, a targeting ligand, a therapeutic agent, or a combination thereof.

15. A kit comprising a nanobubble of claim 1, optionally, comprising a source of ultrasound.

16. A pharmaceutical composition comprising a nanobubble of claim 1, and a pharmaceutically acceptable carrier.

* * * * *